(12) United States Patent
Zhuang et al.

(10) Patent No.: US 11,959,075 B2
(45) Date of Patent: *Apr. 16, 2024

(54) SYSTEMS AND METHODS FOR DETERMINING NUCLEIC ACIDS

(71) Applicant: President and Fellows of Harvard College, Cambridge, MA (US)

(72) Inventors: Xiaowei Zhuang, Cambridge, MA (US); Kok-Hao Chen, Cambridge, MA (US); Alistair Boettiger, Cambridge, MA (US); Jeffrey R. Moffitt, Cambridge, MA (US); Siyuan Wang, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/184,967

(22) Filed: Mar. 16, 2023

(65) Prior Publication Data

US 2023/0323338 A1  Oct. 12, 2023

Related U.S. Application Data

(60) Continuation of application No. 18/046,409, filed on Oct. 13, 2022, which is a continuation of application No. 17/374,000, filed on Jul. 13, 2021, which is a division of application No. 15/329,683, filed as application No. PCT/US2015/042556 on Jul. 29, 2015, now Pat. No. 11,098,303.

(60) Provisional application No. 62/142,653, filed on Apr. 3, 2015, provisional application No. 62/050,636, filed on Sep. 15, 2014, provisional application No. 62/031,062, filed on Jul. 30, 2014.

(51) Int. Cl.
| | | |
|---|---|---|
| C12N 15/10 | (2006.01) | |
| C07H 21/02 | (2006.01) | |
| C07H 21/04 | (2006.01) | |
| C12Q 1/6806 | (2018.01) | |
| C12Q 1/6837 | (2018.01) | |
| C12Q 1/6841 | (2018.01) | |
| C12Q 1/6869 | (2018.01) | |
| G06N 7/01 | (2023.01) | |
| G16B 25/00 | (2019.01) | |
| G16B 25/20 | (2019.01) | |
| G16B 40/10 | (2019.01) | |
| G16C 20/10 | (2019.01) | |
| C12Q 1/6816 | (2018.01) | |
| G16B 30/00 | (2019.01) | |
| G16B 40/00 | (2019.01) | |

(52) U.S. Cl.
CPC ......... *C12N 15/1065* (2013.01); *C07H 21/02* (2013.01); *C07H 21/04* (2013.01); *C12N 15/10* (2013.01); *C12N 15/1093* (2013.01); *C12Q 1/6806* (2013.01); *C12Q 1/6837* (2013.01); *G16B 25/00* (2019.02); *G16B 25/20* (2019.02); *G16B 40/10* (2019.02); *G16C 20/10* (2019.02); *C12Q 1/6816* (2013.01); *C12Q 1/6841* (2013.01); *C12Q 1/6869* (2013.01); *G06N 7/01* (2023.01); *G16B 30/00* (2019.02); *G16B 40/00* (2019.02)

(58) Field of Classification Search
None
See application file for complete search history.

(56) References Cited

U.S. PATENT DOCUMENTS

| | | |
|---|---|---|
| 4,888,278 A | 12/1989 | Singer et al. |
| 5,382,511 A | 1/1995 | Stapleton |
| 5,501,954 A | 3/1996 | Mahr et al. |
| 5,563,033 A | 10/1996 | Lawrence et al. |
| 5,563,056 A | 10/1996 | Swan et al. |
| 6,001,568 A | 12/1999 | Chetverin et al. |
| 6,150,516 A | 11/2000 | Brenner et al. |

(Continued)

FOREIGN PATENT DOCUMENTS

| | | |
|---|---|---|
| CN | 1570140 A | 1/2005 |
| CN | 1898397 A | 1/2007 |

(Continued)

OTHER PUBLICATIONS

Lubek et al Single-cell in situ RNA profiling by sequential hybridization Nature methods vol. 11 No. 4 Apr. 2014.*

(Continued)

*Primary Examiner* — Joseph Woitach
(74) *Attorney, Agent, or Firm* — Wolf, Greenfield & Sacks, P.C.

(57) ABSTRACT

The present invention generally relates to systems and methods for imaging or determining nucleic acids, for instance, within cells. In some embodiments, the transcriptome of a cell may be determined. Certain embodiments are directed to determining nucleic acids, such as mRNA, within cells at relatively high resolutions. In some embodiments, a plurality of nucleic acid probes may be applied to a sample, and their binding within the sample determined, e.g., using fluorescence, to determine locations of the nucleic acid probes within the sample. In some embodiments, codewords may be based on the binding of the plurality of nucleic acid probes, and in some cases, the codewords may define an error-correcting code to reduce or prevent misidentification of the nucleic acids. In certain cases, a relatively large number of different targets may be identified using a relatively small number of labels, e.g., by using various combinatorial approaches.

22 Claims, 48 Drawing Sheets

Specification includes a Sequence Listing.

(56) References Cited

U.S. PATENT DOCUMENTS

| | | |
|---|---|---|
| 6,232,067 B1 | 5/2001 | Hunkapiller et al. |
| 6,444,421 B1 | 9/2002 | Chung et al. |
| 6,524,798 B1 | 2/2003 | Goldbard et al. |
| 6,620,584 B1 | 9/2003 | Chee et al. |
| 6,654,696 B1 | 11/2003 | Davies |
| 7,033,754 B2 | 4/2006 | Chee et al. |
| 7,122,319 B2 | 10/2006 | Liu et al. |
| 7,226,734 B2 | 6/2007 | Chee et al. |
| 7,368,265 B2 | 5/2008 | Brenner et al. |
| 7,455,971 B2 | 11/2008 | Chee et al. |
| 7,473,767 B2 | 1/2009 | Dimitrov |
| 7,499,806 B2 | 3/2009 | Kermani et al. |
| 7,629,125 B2 | 12/2009 | Sood et al. |
| 7,727,721 B2 | 6/2010 | Pierce et al. |
| 7,776,613 B2 | 8/2010 | Zhuang et al. |
| 7,785,790 B1 | 8/2010 | Church et al. |
| 7,807,447 B1 | 10/2010 | Shoemaker et al. |
| 7,838,302 B2 | 11/2010 | Zhuang et al. |
| 7,906,285 B2 | 3/2011 | Drmanac |
| 7,910,304 B2 | 3/2011 | Drmanac |
| 7,981,604 B2 | 7/2011 | Quake |
| 8,460,865 B2 | 6/2013 | Chee et al. |
| 8,564,792 B2 | 10/2013 | Zhuang et al. |
| 8,741,566 B2 | 6/2014 | Winther et al. |
| 8,765,642 B2 | 7/2014 | Curry |
| 9,163,283 B2 | 10/2015 | Chee et al. |
| 9,201,063 B2 | 12/2015 | Sood et al. |
| 9,359,636 B2 | 6/2016 | Tuschl et al. |
| 9,371,598 B2 | 6/2016 | Chee |
| 9,518,982 B2 | 12/2016 | Sood et al. |
| 9,556,473 B2 | 1/2017 | Bernitz et al. |
| 9,677,125 B2 | 6/2017 | Sood et al. |
| 9,712,805 B2 | 7/2017 | Zhuang et al. |
| 9,778,154 B2 | 10/2017 | Gradinaru et al. |
| 9,850,536 B2 | 12/2017 | Oliphant et al. |
| 9,896,720 B2 | 2/2018 | Raj et al. |
| 9,944,972 B2 | 4/2018 | Yin et al. |
| 10,073,035 B2 | 9/2018 | Zhuang et al. |
| 10,190,151 B2 | 1/2019 | Yin et al. |
| 10,227,639 B2 | 3/2019 | Levner et al. |
| 10,240,146 B2 | 3/2019 | Zhuang et al. |
| 10,266,876 B2 | 4/2019 | Cai et al. |
| 10,267,808 B2 | 4/2019 | Cai |
| 10,457,980 B2 | 10/2019 | Cai et al. |
| 10,501,791 B2 | 12/2019 | Church et al. |
| 10,510,435 B2 | 12/2019 | Cai et al. |
| 10,526,649 B2 | 1/2020 | Chen et al. |
| 10,545,075 B2 | 1/2020 | Deisseroth et al. |
| 10,563,257 B2 | 2/2020 | Boyden et al. |
| 10,829,814 B2 | 11/2020 | Fan et al. |
| 10,870,846 B2 | 12/2020 | Scott et al. |
| 10,961,566 B2 | 3/2021 | Chee |
| 11,021,737 B2 | 6/2021 | Church et al. |
| 11,078,520 B2 | 8/2021 | Church et al. |
| 11,098,303 B2 | 8/2021 | Zhuang et al. |
| 11,788,123 B2 | 10/2023 | Zhuang et al. |
| 2002/0058248 A1 | 5/2002 | Kolanko et al. |
| 2002/0094116 A1 | 7/2002 | Frost et al. |
| 2003/0064395 A1 | 4/2003 | Chung |
| 2003/0104428 A1 | 6/2003 | Branton et al. |
| 2003/0148335 A1 | 8/2003 | Shen et al. |
| 2004/0002095 A1 | 1/2004 | Liu et al. |
| 2004/0053300 A1 | 3/2004 | Soderlund et al. |
| 2004/0081979 A1 | 4/2004 | Knezevic et al. |
| 2004/0091880 A1 | 5/2004 | Wiebusch et al. |
| 2004/0137488 A1 | 7/2004 | Kenten et al. |
| 2004/0248144 A1 | 12/2004 | Mir |
| 2005/0042612 A1 | 2/2005 | Hubbard et al. |
| 2005/0064435 A1 | 3/2005 | Su et al. |
| 2005/0106594 A1 | 5/2005 | Ellington et al. |
| 2005/0123959 A1 | 6/2005 | Williams et al. |
| 2005/0176023 A1 | 8/2005 | Ramon et al. |
| 2005/0233318 A1 | 10/2005 | Chee et al. |
| 2006/0024711 A1 | 2/2006 | Lapidus et al. |
| 2006/0051798 A1 | 3/2006 | Mirken et al. |
| 2006/0141502 A1 | 6/2006 | Capodieci et al. |
| 2006/0177833 A1 | 8/2006 | Brenner |
| 2006/0228733 A1 | 10/2006 | Pierce et al. |
| 2006/0275782 A1 | 12/2006 | Gunderson et al. |
| 2006/0292559 A1 | 12/2006 | Reddy et al. |
| 2007/0020650 A1 | 1/2007 | Kahvejian |
| 2007/0048759 A1 | 3/2007 | Luo et al. |
| 2007/0190543 A1 | 8/2007 | Livak |
| 2007/0231824 A1 | 10/2007 | Chee et al. |
| 2008/0050731 A1 | 2/2008 | Agnew et al. |
| 2008/0269068 A1 | 10/2008 | Church et al. |
| 2008/0299565 A1 | 12/2008 | Schneider et al. |
| 2009/0105082 A1 | 4/2009 | Chetverin et al. |
| 2009/0131269 A1 | 5/2009 | Martin et al. |
| 2010/0323348 A1 | 1/2010 | Hamady et al. |
| 2010/0216146 A1 | 8/2010 | Williams et al. |
| 2010/0291557 A1 | 11/2010 | Livak et al. |
| 2010/0304994 A1 | 12/2010 | Wu et al. |
| 2011/0002530 A1 | 1/2011 | Zhuang et al. |
| 2011/0086774 A1 | 4/2011 | Dunaway |
| 2011/0092381 A1 | 4/2011 | Sood et al. |
| 2011/0245111 A1 | 10/2011 | Chee |
| 2011/0257031 A1 | 10/2011 | Bodeau et al. |
| 2011/0294135 A1 | 12/2011 | Carlson |
| 2012/0035065 A1 | 2/2012 | Smolke et al. |
| 2012/0040397 A1 | 2/2012 | Luo et al. |
| 2012/0088235 A1 | 4/2012 | Kokoris et al. |
| 2012/0100540 A1 | 4/2012 | Wu et al. |
| 2012/0129165 A1 | 5/2012 | Raj et al. |
| 2012/0208724 A1 | 8/2012 | Steemers et al. |
| 2012/0270214 A1 | 10/2012 | Bernitz et al. |
| 2013/0053256 A1 | 2/2013 | Hubbell |
| 2013/0096014 A1 | 4/2013 | Anderson et al. |
| 2013/0190196 A1 | 7/2013 | Onderdonk et al. |
| 2013/0261019 A1 | 10/2013 | Lin et al. |
| 2014/0024024 A1 | 1/2014 | Sood et al. |
| 2014/0031243 A1 | 1/2014 | Cai et al. |
| 2014/0073520 A1 | 3/2014 | Cai et al. |
| 2015/0087001 A1 | 3/2015 | Gradinaru et al. |
| 2015/0105298 A1 | 4/2015 | Czaplinski |
| 2015/0144490 A1 | 5/2015 | Deisseroth et al. |
| 2015/0211023 A1 | 7/2015 | Shiboleth et al. |
| 2015/0267251 A1 | 9/2015 | Cai et al. |
| 2016/0010054 A1 | 1/2016 | Gartner et al. |
| 2016/0116384 A1 | 4/2016 | Chen et al. |
| 2016/0153005 A1 | 6/2016 | Cong et al. |
| 2016/0161472 A1 | 6/2016 | Jungmann et al. |
| 2016/0194701 A1 | 7/2016 | Beechem et al. |
| 2016/0257997 A1 | 9/2016 | Stender et al. |
| 2016/0304952 A1 | 10/2016 | Boyden et al. |
| 2016/0305856 A1 | 10/2016 | Stuart et al. |
| 2016/0369329 A1 | 12/2016 | Cai et al. |
| 2016/0370295 A1 | 12/2016 | Zhuang et al. |
| 2017/0212986 A1 | 7/2017 | Zhuang et al. |
| 2017/0220733 A1 | 8/2017 | Zhuang et al. |
| 2017/0327876 A1 | 11/2017 | Khafizov et al. |
| 2018/0142286 A1 | 5/2018 | Dunaway et al. |
| 2018/0230226 A1 | 8/2018 | Podack et al. |
| 2019/0233812 A1 | 8/2019 | Zhuang et al. |
| 2019/0264270 A1 | 8/2019 | Zhuang et al. |
| 2019/0276881 A1 | 9/2019 | Zhuang et al. |
| 2020/0064340 A1 | 2/2020 | Jungmann et al. |
| 2020/0095630 A1 | 3/2020 | Zhuang et al. |
| 2020/0399689 A1 | 12/2020 | Luo et al. |
| 2021/0087625 A1 | 3/2021 | Fan et al. |
| 2022/0025442 A1 | 1/2022 | Zhuang et al. |
| 2022/0064697 A1 | 3/2022 | Zhuang et al. |
| 2022/0205983 A1 | 6/2022 | Zhuang et al. |
| 2023/0279383 A1 | 9/2023 | Zhuang et al. |
| 2023/0279387 A1 | 9/2023 | Zhuang et al. |
| 2023/0323339 A1 | 10/2023 | Zhuang et al. |
| 2023/0348958 A1 | 11/2023 | Zhuang et al. |

FOREIGN PATENT DOCUMENTS

| | | |
|---|---|---|
| CN | 1950516 A | 4/2007 |
| CN | 102149829 A | 8/2011 |
| CN | 102171234 A | 8/2011 |
| CN | 103649331 A | 3/2014 |

(56) References Cited

FOREIGN PATENT DOCUMENTS

| | | |
|---|---|---|
| CN | 103703143 A | 4/2014 |
| CN | 103890586 A | 6/2014 |
| CN | 104350372 A | 2/2015 |
| CN | 105164279 A | 12/2015 |
| CN | 105274144 A | 1/2016 |
| CN | 105531377 A | 4/2016 |
| CN | 105556309 A | 5/2016 |
| CN | 107075546 A | 8/2017 |
| EP | 1064399 A2 | 1/2001 |
| EP | 1 196 630 B1 | 11/2008 |
| EP | 2 082 226 B1 | 8/2011 |
| WO | WO 1999/031277 A1 | 6/1999 |
| WO | WO 01/23614 A1 | 4/2001 |
| WO | WO 02/00336 A2 | 1/2002 |
| WO | WO 03/02979 A2 | 1/2003 |
| WO | WO 03/003810 A2 | 1/2003 |
| WO | WO 03/003810 A3 | 1/2003 |
| WO | WO 2005/047535 A1 | 5/2005 |
| WO | WO 2005/066368 A2 | 7/2005 |
| WO | WO 2006/003423 A2 | 1/2006 |
| WO | WO 2007/001986 A2 | 1/2007 |
| WO | WO 2008/064067 A2 | 5/2008 |
| WO | WO 2008/091296 A2 | 7/2008 |
| WO | WO 2008/108843 A2 | 9/2008 |
| WO | WO 2009/085218 A | 7/2009 |
| WO | WO 2010/091107 A1 | 8/2010 |
| WO | WO 2011/038403 A1 | 3/2011 |
| WO | WO 2011/094669 A1 | 8/2011 |
| WO | WO 2011/112634 A2 | 9/2011 |
| WO | WO 2011/143583 A1 | 11/2011 |
| WO | WO 2012/049316 A1 | 4/2012 |
| WO | WO 2012/110899 A2 | 8/2012 |
| WO | WO 2013/090360 A2 | 6/2013 |
| WO | WO 2013/096851 A1 | 6/2013 |
| WO | WO 2014/028538 A2 | 2/2014 |
| WO | WO 2014/182528 A2 | 11/2014 |
| WO | WO 2015/127183 A2 | 8/2015 |
| WO | WO 2015/160690 A1 | 10/2015 |
| WO | WO 2016/018960 A1 | 2/2016 |
| WO | WO 2016/018963 A9 | 2/2016 |
| WO | WO 2016/028843 A2 | 2/2016 |
| WO | WO 2017/143155 A2 | 8/2017 |
| WO | WO 2018/026873 A1 | 2/2018 |
| WO | WO 2018/089438 A1 | 5/2018 |
| WO | WO 2018/089445 A1 | 5/2018 |
| WO | WO 2018/218150 A1 | 11/2018 |

OTHER PUBLICATIONS

Femino et al Visualization of Single RNA Transcripts in Situ Science vol. 280 Apr. 24, 1998.*
Cai Turning single cells into microarrays by super-resolution barcoding Briefings in Functional Genomics. vol 12. No. 2. 75 doi:10.1093/bfgp/els054.*
Lubek et al Single-cell systems biology by super-resolution imaging and combinatorial labeling Nature methods vol. 9 No. 7 Jul. 2012.*
Fortina et al Digital mRNA profiling Nature Biotechnology vol. 26 No. 3 Mar. 2008.*
Babcock, Multiplane and Spectrally-Resolved Single Molecule Localization Microscopy with Industrial Grade CMOS cameras. Scientific Reports. Jan. 2018;8:1726. 8 pages.
Baeissa et al., DNA-Functionalized Monolithic Hydrogels and Gold Nanoparticles for Colorimetric DNA Detection. Applied Materials & Interfaces. Nov. 2010; 2(12):3594-3600. doi:10.1021/am100780d.
Beliveau et al., Versatile design and synthesis platform for visualizing genomes with Oligopaint FISH probes. Proc Natl Acad Sci U S A. Dec. 26, 2012;109(52):21301-6. doi: 10.1073/pnas.1213818110. Epub Dec. 11, 2012.
Binladen et al., The use of coded PCR primers enables high-throughput sequencing of multiple homolog amplification products by 454 parallel sequencing. PLoS One. Feb. 14, 2007;2(2):e197.

Chen et al., Expansion microscopy. Science. Jan. 2015; 347(6221):543-548.
Chen et al., Nanoscale imaging of RNA with expansion microscopy. Nature Methods. 2016; 13:679-684.
Chen et al., RNA imaging. Spatially resolved, highly multiplexed RNA profiling in single cells. Science. 2015;348(6233):aaa6090.
Chen et al., Spatially resolved, highly multiplexed RNA profiling in single cells. Science. Apr. 24, 2015;348(6233):aaa6090. doi: 10.1126/science.aaa6090. Epub Apr. 9, 2015.
Chen et al., Supplemental Material for Expansion microscopy. Science. Jan. 2015; 347(6221):1-18.
Chung et al., Clarity for mapping the nervous system [published correction appears in Nat Methods. Oct. 2013;10(10):1035]. Nat Methods. 2013;10(6):508-513.
Cui et al., Beyond quantification: in situ analysis of transcriptome and pre-mRNA alternative splicing at the nanoscale. Wiley Interdiscip Rev Nanomed Nanobiotechnol. Jul. 2017;9(4). doi: 10.1002/wnan.1443. Epub Nov. 4, 2016.
Darouich et al., Use of DOP-PCR for amplification and labeling of BAC DNA for FISH. Biotech Histochem. Feb. 2012;87(2):117-21. doi: 10.3109/10520295.2011.559175.
Datlinger et al., Pooled CRISPR screening with single-cell transcriptome readout. Nat Methods. Mar. 2017;14(3):297-301. doi: 10.1038/nmeth.4177. Epub Jan. 18, 2017.
Dixit et al., Perturb-Seq: Dissecting Molecular Circuits with Scalable Single-Cell RNA Profiling of Pooled Genetic Screens. Cell. Dec. 15, 2016;167(7):1853-1866.e17. doi: 10.1016/j.cell.2016.11.038.
Epstein et al., Reutilization of Previously Hybridized Slides for Flourescence In Situ Hybridization. Cytometry. 1995;21:378-381.
Fakruddin et al., Nucleic acid sequence based amplification (NASBA)-prospects and applications. Int. J. Life Sci. Pharm. Res. Mar. 2012; 2(1): L106-L121.
Gunderson et al., Decoding Randomly Ordered DNA Arrays. Methods. 2004;14:870-877.
Kanagawa, Bias and artifacts in multitemplate polymerase chain reactions (PCR). J Biosci Bioeng. 2003;96(4):317-23. doi: 10.1016/S1389-1723(03)90130-7.
Koshkin et al., LNA (locked nucleic acids: Synthesis, of the adenine, cytosine, guanine, 5-methylcytosine, thymine and uracil bicyclonucleside monomers, oligomerization and unprecedented nucleic acid recognition. Tetrahedron. 1998;54:3607-30.
Kuhn et al., Poly(A) Tail Length is Controlled by the Nuclear Poly(A)-binding Protein Regulating the Interaction between Poly(A) Polymerase and the Cleavage and Polyadenylation Specificity Factor. The Journal of Biological Chemistry. Aug. 21, 2009;284(34):22803-22814.
Levsky et al., Single-cell gene expression profiling. Science. Aug. 2, 2002; 297:836-840.
Libus et al., Quantification of cDNA generated by reverse transcription of total RNA provides a simple alternative tool for quantitative RT-PCR normalization. Biotechniques. Aug. 2006;41(2):156, 158, 160 passim. doi: 10.2144/000112232.
Lubeck et al., Single-cell in situ RNA profiling by sequential hybridization. Nature Methods. Apr. 2014; 11(4): 360-1.
Lubeck et al., Single-cell in situ RNA profiling by sequential hybridization. Nature Methods. Apr. 2014; 11(4): 360-1. Supplementary Information.
May, How many species are there on Earth? Science. Sep. 16, 1988;241(4872):1441-9. doi: 10.1126/science.241.4872.1441.
Moffitt et al., High-performance multiplexed fluorescence in situ hybridization in culture and tissue with matrix imprinting and clearing. Proc Natl Acad Sci U S A. Dec. 13, 2016;113(50):14456-14461. Epub Nov. 22, 2016.
Moffitt et al., High-throughput single-cell gene-expression profiling with multiplexed error- robust fluorescence in situ hybridization. Proc Natl Acad Sci U S A. Sep. 27, 2016;113(39):11046-51. doi: 10.1073/pnas.1612826113. Epub Sep. 13, 2016.
Moffitt et al., RNA Imaging with Multiplexed Error-Robust Fluorescence In Situ Hybridization (MERFISH). Methods Enzymol. 2016;572:1-49. doi: 10.1016/bs.mie.2016.03.020. Epub Apr. 27, 2016.

(56) References Cited

OTHER PUBLICATIONS

Murgha et al., Large-Scale Generation of Synthetic DNA Libraries: Sequence-Specific Priming of ReverseTranscription, PhD Dissertation. University of Michigan. 2012.

Nilsson et al. Comparison of fungal 80 S ribosomes by cryo-EM reveals diversity in structure and conformation of rRNA expansion segments. J Mol Biol. Jun. 1, 2007;369(2):429-38. doi: 10.1016/j.jmb.2007.03.035. Epub Mar. 20, 2007.

Philippova et al., Polymer Gels. In: Polymer Science: A Comprehensive Reference (vol. 1). 2012. Chapter 1.13: 339-366.

Player et al., Single-copy gene detection using branched DNA (bDNA) in situ hybridization. The Journal of Histochemistry & Cytochemistry. 2001; 49(5): 603-611.

Polz et al., Bias in template-to-product ratios in multitemplate PCR. Appl Environ Microbiol. Oct. 1998;64(10):3724-30. doi: 10.1128/AEM.64.10.3724-3730.1998.

Prabhat et al., Simultaneous imaging of different focal planes in fluorescence microscopy for the study of cellular dynamics in three dimensions. IEEE Trans Nanobioscience. Dec. 2004;3(4):237-42. doi: 10.1109/tnb.2004.837899.

Shiels et al., RNA-DNA hybrids containing damaged DNA are substrates for RNase H. Bioorg Med Chem Lett. Oct. 8, 2001;11(19):2623-6.

Thomsen et al., Dramatically improved RNA in situ hybridization signals using LNA-modified probes.RNA. Nov. 2005;11(11):1745-8. doi: 10.1261/rna.2139705. Epub Sep. 21, 2005.

Tillberg et al., Protein-retention expansion microscopy of cells and tissues labeled using standard fluorescent proteins and antibodies. Nat. Biotechnol. 2016; 34(9):987-992.

Tsanov et al., smiFISH and FISH-quant—a flexible single RNA detection approach with super-resolution capability. Nucleic Acids Res. 2016;44(22):e165.

Valoczi et al., Sensitive and specific detection of microRNAs by northern blot analysis using LNA-modified oligonucleotide probes. Nucleic Acids Res. Dec. 14, 2004;32(22):e175. doi: 10.1093/nar/gnh171.

Wang et al., Imaging-based pooled CRISPR screening reveals regulators of lncRNA localization. Proc Natl Acad Sci U S A. May 28, 2019;116(22):10842-10851. doi: 10.1073/pnas.1903808116. Epub May 13, 2019.

Ward, The Human Cell Atlas; An International Effort. AltTox.org. Oct. 31, 2016. Available at: http://alttox.org/the-human-cell-atlas-an-international-effort/ [Last accessed Jan. 21, 2022].

Wenming, Application of in situ Nucleic Acid Hybridization in Molecular Pathology of Tumor. Pathology Department, Institute of Hepatobiliary Surgery, The Second Military Medical University. Jul. 12, 1992: 182-184.

Wienholds et al., MicroRNA expression in zebrafish embryonic development. Science. Jul. 8, 2005;309(5732):310-1. doi: 10.1126/science.1114519. Epub May 26, 2005.

Xiaojun et al., Imaging of Single Molecules by Wide-Fiel Optical Microscopy. Progress in Chemistry. Mar. 2013; 25(2/3):371-379.

Yang et al., Single-cell phenotyping within transparent intact tissue through whole-body clearing. Cell. 2014;158(4):945-958.

Yujiao et al., Application of Fluorescence In Situ Hybridization In Analysis Of Environmental Microbial Ecology. Techniques and Equipment for Environmental Pollution Control. Nov. 2004;5(11):14-20.

Zhang et al., Tandem Spinach Array for mRNA Imaging in Living Bacterial Cells. Sci Rep. 2015;5:17295.

Zhen et al., Poly-fish: A technique of repeated hybridizations that improves cytogenetic analysis of fetal cells in maternal blood. Prenatal Diagnosis. Mar. 21, 1998; 18: 1181-1185.

Albrecht et al., Photo-and electropatterning of hydrogel-encapsulated living cell arrays. Lab Chip. Jan. 2005;5(1):111-8. doi: 10.1039/b406953f. Epub Nov. 24, 2004.

Bintu et al., Super-resolution chromatin tracing reveals domains and cooperative interactions in single cells. Science. Oct. 26, 2018;362(6413):eaau1783. doi: 10.1126/science.aau1783.

Cai, Turning single cells into microarrays by super-resolution barcoding. Brief Funct Genomics. Mar. 2013;12(2):75-80. doi: 10.1093/bfgp/els054. Epub Nov. 22, 2012.

Carmona et al., LncRNA Jpx induces Xist expression in mice using both trans and cis mechanisms. PLoS Genet. May 7, 2018;14(5):e1007378. doi: 10.1371/journal.pgen.1007378. eCollection May 2018.

Chung et al., Structural and molecular interrogation of intact biological systems. Nature. May 16, 2013;497(7449):332-7. doi: 10.1038/nature12107. Epub Apr. 10, 2013.

Church, Proposal for a Center for the determination of the Causal Transcriptional Consequences of Human Genetic Variation (CTCHGV). Department of Genetics, Harvard Medical School. May 25, 2009. 64 pages.

Cremer et al., Multicolor 3D Fluorescence In Situ Hybridization for Imagin Interphase Chromosomes. Methods Mol Biol. The Nucleus: vol. 1: Nuclei and Subnuclear Components. 2008;463:205-39. doi: 10.1007/978-1-59745-406-3_15.

Fan et al., Highly parallel genomic assays. Review. Nat Rev Genet. Aug. 2006;7(8):632-44. doi: 10.1038/nrg1901.

Femino et al., Visualization of Single RNA Transcripts in Situ. Science. Apr. 24, 1998;280(5363):585-90. doi: 10.1126/science.280.5363.585.

Goransson, Readout Strategies for Biomolecular Analyses. Digital Comprehensive Summaries of Uppsala Dissertations from the Faculty of Science and Technology 563, Uppsala Universitet. 2008:42 pages.

Ke et al., In situ sequencing for RNA analysis in preserved tissue and cells. Nat Methods. Sep. 2013;10(9):857-60. doi: 10.1038/nmeth.2563. Epub Jul. 14, 2013.

Larsson et al., In situ genotyping individual DNA molecules by target-primed rolling-circle amplification of padlock probes. Nat Methods. Dec. 2004;1(3):227-32. doi: 10.1038/nmeth723. Epub Nov. 18, 2004.

Lubeck et al., Single cell in situ RNA profiling by sequential hybridization. Nat Methods. Apr. 2014;11(4):360-361. doi:10.1038/nmeth.2892. Author manuscript provided. 3 pages.

Lubeck et al., Single Cell Systems Biology by Super-resolution imaging and combinatorial Labeling. Nat Methods. Jun. 3, 2012;9(7):743-8. doi: 10.1038/nmeth.2069. Author manuscript provided. 18 pages.

Mali et al., Barcoding cells using cell-surface programmable DNA-binding domains. Nat Methods. May 2013;10(5):403-6. doi: 10.1038/nmeth.2407. Epub Mar. 17, 2013. Author manuscript provided. 12 pages.

Mitra et al., In situ localized amplification and contact replication of Many individual DNA Molecules, Nucleic Acids Res. Dec. 15, 1999;27(24):e34. doi: 10.1093/nar/27.24.e34.

Müller et al., A Nonredundant Multicolor Bar Code as a Screening Tool for Rearrangements in Neoplasia, Genes, Chromosomes & Cancer. Jan. 1, 2004;39(1):59-70.

Namekawa et al., Detection of nascent RNA, single-copy DNA and protein localization by ImmunoFISH in mouse germ cells and preimplantation embryos. Nat Protoc. Mar. 2011;6(3):270-84. doi: 10.1038/nprot.2010.195. Epub Feb. 10, 2011. Author manuscript provided. 36 pages.

Reinartz et al., Technique Review: Massively parallel signature sequencing (MPSS) as a tool for in-depth quantitaive gene expression profiling in all organisms. Brief Funct Genomic Proteomic. Feb. 2002;1(1):95-104. doi: 10.1093/bfgp/1.1.95.

Steemers et al., Whole genome genotyping technologies on the BeadArray TM Platform. Biotechnol J. Jan. 2007;2(1):41-9. doi: 10.1002/biot.200600213.

Su et al., Genome-Scale Imaging of the 3D Organization and Transcriptional Activity of Chromatin. Cell. Sep. 17, 2020;182(6):1641-1659.e26. doi: 10.1016/j.cell.2020.07.032. Epub Aug. 20, 2020.

Torgersen et al., Localization of mRNAs and Proteins in Methyl Methacrylate-embedded Tissues. Journal of Histochemistry & Cytochemistry. 2009;57(9):825-830. Epub May 11, 2009.

Volpi et al., FISH glossary: an overview of the fluorescence in situ hybridization technique. Biotechniques. Oct. 2008;45(4):385-6, 388, 390, 392, 394, 396, 398, 400, 402, 404, 406, 408-9. doi: 10.2144/000112811.

(56) References Cited

OTHER PUBLICATIONS

Weibrecht et al., Simultaneous Visualization of Both Signaling Cascade Activity and End-Point Gene Expression in Single Cells. PLoS One. 2011;6(5):e20148. doi: 10.1371/journal.pone.0020148. Epub May 25, 2011.
Xia et al., Spatial transcriptome profiling by MERFISH reveals subcellular RNA compartmentalization and cell cycle-dependent gene expression. Proc Natl Acad Sci U S A. Sep. 24, 2019;116(39):19490-19499. doi: 10.1073/pnas.1912459116. Epub Sep. 9, 2019.
U.S. Appl. No. 17/374,000, filed Jul. 13, 2021, Zhuang et al.
U.S. Appl. No. 18/046,409, filed Oct. 13, 2022, Zhuang et al.
U.S. Appl. No. 16/253,919, filed Jan. 22, 2019, Zhuang et al.
U.S. Appl. No. 16/347,874, filed May 7, 2019, Zhuang et al.
U.S. Appl. No. 16/616,833, filed Nov. 25, 2019, Zhuang et al.
U.S. Appl. No. 16/348,071, filed May 7, 2019, Zhuang et al.
U.S. Appl. No. 17/413,148, filed Jun. 11, 2021, Zhuang et al.
U.S. Appl. No. 17/604,646, filed Oct. 18, 2021, Zhuang et al.
U.S. Appl. No. 17/769,536, filed Apr. 15, 2022, Zhuang et al.
U.S. Appl. No. 17/770,943, filed Apr. 21, 2022, Zhuang et al.
[No Author Listed] Digital CCD Camera C4742-95-12HR Instruction Manual. Hamamatsu Photonics K.K. Version 1.4. Apr. 2007. pp. 1-45.
Angell et al., Silicon micromechanical devices. Scientific American. Apr. 1983;248(4):44-55.
Arhel et al., Quantitative four-dimensional tracking of cytoplasmic and nuclear HIV-1 complexes. Nat Methods. Oct. 2006;3(10):817-24. doi: 10.1038/nmeth928.
Bates et al., Stochastic optical reconstruction microscopy (STORM): a method for superresolution fluorescence imaging. Cold Spring Harb Protoc. Jun. 1, 2013;2013(6):498-520. doi: 10.1101/pdb.top075143.
Bystrykh et al., Generalized DNA barcode design based on Hamming codes. PLoS One. 2012;7(5):e36852. doi: 10.1371/journal.pone.0036852. Epub May 17, 2012.
Camacho et al., BLAST+: architecture and applications. BMC Bioinformatics. Dec. 15, 2009:10:421. doi: 10.1186/1471-2105-10-421.
Chen et al., Gene editing technology and its research progress in China. Yi Chuan. Oct. 20, 2018;40(10):900-915. Chinese. doi: 10.16288/j.yczz.18-195.
Chi et al., Super-resolution microscopy: breaking the limits. Nature Methods. Jan. 2009;6(1):15-18.
Deng et al., Targeted bisulfite sequencing reveals changes in DNA methylation associated with nuclear reprogramming. Nat Biotechnol. Apr. 2009;27(4):353-60. doi: 10.1038/nbt.1530. Epub Mar. 29, 2009.
Duffy et al., Rapid prototyping of microfluidic systems and polydimethylsiloxane. Anal Chem. 1998;70:474-80.
Goransson et al., A single molecule array for digital targeted molecular analyses. Nucleic Acids Res. Jan. 2009;37(1):e7. doi: 10.1093/nar/gkn921. Epub Nov. 25, 2008. PMID: 19033366; PMCID: PMC2615615.
Gozzetti et al., Fluorescence in situ hybridization: uses and limitations. Semin Hematol. Oct. 2000;37(4):320-33. doi: 10.1016/s0037-1963(00)90013-1.
Hamming et al., Coding and Information Theory. Second Edition; Chapters 1-3. 1980; pp. 1-50.

Henriques et al., Palm and Storm: unlocking live-cell super-resolution. Biopolymers. May 2011;95(5):322-31. doi: 10.1002/bip.21586. Epub Jan. 19, 2011.
Jakt et al., A continuum of transcriptional identities visualized by combinatorial fluorescent in situ hybridization. Development. Jan. 1, 2013;140(1):216-25. doi: 10.1242/dev.086975. Epub Nov. 22, 2012.
Jensen et al., Technical review: In situ hybridization. Anat Rec (Hoboken). Aug. 2014;297(8):1349-53. doi: 10.1002/ar.22944. Epub May 9, 2014.
Jensen et al., Technical review: types of imaging-direct Storm. Anat Rec (Hoboken). Dec. 2014;297(12):2227-31. doi: 10.1002/ar.22960. Epub Jul. 4, 2014.
Kamiyama et al., Development in the Storm. Dev Cell. Dec. 11, 2012;23(6):1103-10. doi: 10.1016/j.devcel.2012.10.003.
Krishnan et al., Barcodes for DNA sequencing with guaranteed error correction capability. Electronics Letters. Feb. 17, 2011;47(4):1-2.
Kwon et al., Single-molecule fluorescence in situ hybridization: quantitative imaging of single RNA molecules. BMB Rep. Feb. 2013;46(2):65-72. doi: 10.5483/bmbrep.2013.46.2.016.
Larsson et al., In situ detection and genotyping of individual mRNA molecules. Nat Methods. May 2010;7(5):395-7. doi: 10.1038/nmeth.1448. Epub Apr. 11, 2010. Supplementary materials. 26 pages.
Leung et al., Review of super-resolution fluorescence microscopy for biology. Appl Spectrosc. Sep. 2011;65(9):967-80. doi: 10.1366/11-06398.
Levesque et al., Single-chromosome transcriptional profiling reveals chromosomal gene expression regulation. Nat Methods. Mar. 2013;10(3):246-8. doi: 10.1038/nmeth.2372. Epub Feb. 17, 2013. Erratum in: Nat Methods. May 2013;10(5):445.
Levsky et al., Fluorescence in situ hybridization: past, present and future. J Cell Sci. Jul. 15, 2003;116(Pt 14):2833-8. doi: 10.1242/jcs.00633.
Levsky et al., Single-cell gene expression profiling. Science. Aug. 2, 2002; 297:836-840. Supplementary material; 13 pages.
Mujumdar et al., Cyanine dye labeling reagents: sulfoindocyanine succinimidyl esters. Bioconjug Chem. Mar.-Apr. 1993;4(2):105-11. doi: 10.1021/bc00020a001.
Peters et al., Accurate whole-genome sequencing and haplotyping from 10 to 20 human cells. Nature. Jul. 11, 2012;487(7406):190-5. doi: 10.1038/nature11236.
Raj et al., Imaging individual mRNA molecules using multiple singly labeled probes. Nat Methods. Oct. 2008;5(10):877-9. doi: 10.1038/nmeth.1253. Epub Sep. 21, 2008.
Schermelleh et al., A guide to super-resolution fluorescence microscopy. J Cell Biol. Jul. 26, 2010;190(2):165-75. doi: 10.1083/jcb.201002018. Epub Jul. 19, 2010.
Shaffer et al., Turbo Fish: a method for rapid single molecule Rna Fish. Plos One. Sep. 16, 2013;8(9):e75120. doi: 10.1371/journal.pone.0075120.
Shannon, A Mathematical Theory of Communication. Bell System Technical Journal. Jul. 1948;27(3):379-423.
Shannon, A Mathematical Theory of Communication. Bell System Technical Journal. Jul. 1948;27(3):623-656.
Silverman et al., Oligonucleotide probes for RNA-targeted fluorescence in situ hybridization. Adv Clin Chem. 2007;43:79-115.
Moses et al., Museum of spatial transcriptomics. Nat Methods. May 2022;19(5):534-546. doi: 10.1038/s41592-022-01409-2. Epub Mar. 10, 2022.

* cited by examiner

[0 1 0 1 1 1 0 0]

| | Hybridization round | | | | | | | | | | | | | | | | Gene |
|---|---|---|---|---|---|---|---|---|---|---|---|---|---|---|---|---|---|
| Spot number | 1 | 2 | 3 | 4 | 5 | 6 | 7 | 8 | 9 | 10 | 11 | 12 | 13 | 14 | 15 | 16 | |
| 1 | 1 | 0 | 0 | 0 | 1 | 0 | 0 | 0 | 0 | 0 | 0 | 1 | 0 | 1 | 0 | 0 | DYNC1H1 |
| 2 | 0 | 0 | 0 | 1 | 0 | 0 | 1 | 0 | 0 | 1 | 0 | 1 | 0 | 0 | 0 | 0 | EGFR |
| 3 | 0 | 0 | 0 | 0 | 1 | 0 | 1 | 0 | 0 | 0 | 0 | 1 | 0 | 0 | 0 | 1 | FLNA |
| 4 | 0 | 0 | 0 | 0 | 1 | 0 | 0 | 0 | 0 | 0 | 1 | 0 | 0 | 1 | 1 | 0 | TLN1 |
| 5 | 0 | 0 | 0 | 0 | 1 | 0 | 0 | 0 | 0 | 0 | 1 | 0 | 0 | 1 | 1 | 0 | TLN1 |
| 6 | 0 | 0 | 0 | 0 | 0 | 1 | 1 | 0 | 0 | 0 | 1 | 0 | 0 | 1 | 0 | 0 | LRP1 |
| 7 | 0 | 0 | 0 | 0 | 0 | 0 | 0 | 0 | 0 | 0 | 0 | 0 | 0 | 0 | 1 | 0 | unidentiýed |

Hamming Distance 4

Single Error Correction

1 1 0 0 0 0 0 1 0 0 0 0 0 1 0
↓
1 0 0 0 0 0 0 1 0 0 0 0 0 1 0

3 errors → Other codewords

Fig. 12B

Double Error Correction

1 1 0 0 0 0 0 1 0 0 0 0 0 1 0
↓ ↓
0 0 0 0 0 0 0 1 0 0 0 0 0 1 0

2 errors → Other codewords

Fig. 12C

Codebook 1

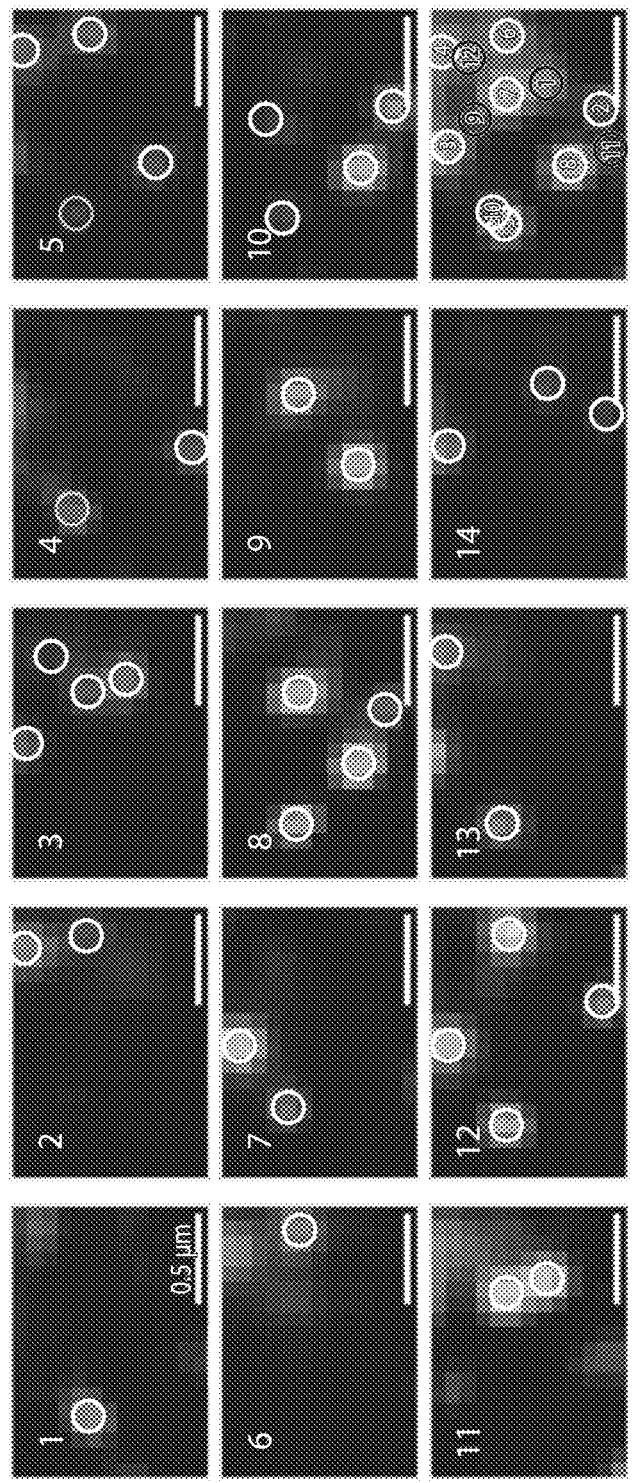

| Spot number | Gene | 1 | 2 | 3 | 4 | 5 | 6 | 7 | 8 | 9 | 10 | 11 | 12 | 13 | 14 |
|---|---|---|---|---|---|---|---|---|---|---|---|---|---|---|---|
| 1 | unidentiýed | 0 | 0 | 1 | 0 | 0 | 0 | 0 | 0 | 0 | 0 | 1 | 0 | 0 | 1 |
| 2 | FLNC | 0 | 0 | 0 | 0 | 0 | 0 | 0 | 1 | 0 | 1 | 0 | 1 | 0 | 1 |
| 3 | ZFPM2 | 0 | 0 | 1 | 0 | 0 | 0 | 1 | 0 | 0 | 0 | 0 | 1 | 0 | 1 |
| 4 | LTBP2 | 1 | 1 | 0 | 0 | 1 | 1 | 0 | 0 | 0 | 0 | 0 | 0 | 1 | 1 |
| 5 | TP53BP1 | 0 | 0 | 0 | 0 | 0 | 0 | 0 | 1 | 0 | 0 | 0 | 1 | 1 | 0 |
| 6 | INTS1 | 0 | 1 | 1 | 0 | 1 | 1 | 0 | 1 | 1 | 0 | 0 | 1 | 0 | 0 |
| 7 | PINK1-AS | 0 | 0 | 0 | 0 | 0 | 0 | 0 | 1 | 1 | 1 | 1 | 0 | 0 | 0 |
| 8 | MLLT4 | 0 | 0 | 0 | 1 | 1 | 0 | 1 | 1 | 0 | 1 | 0 | 0 | 0 | 0 |
| 9 | unidentiýed | 0 | 0 | 0 | 1 | 0 | 0 | 0 | 0 | 0 | 1 | 0 | 0 | 0 | 0 |
| 10 | TRIM14 | 0 | 0 | 0 | 1 | 1 | 0 | 1 | 0 | 0 | 0 | 0 | 0 | 0 | 0 |
| 11 | unidentiýed | 0 | 0 | 0 | 0 | 0 | 0 | 0 | 0 | 0 | 0 | 0 | 0 | 0 | 0 |
| 12 | unidentiýed | 0 | 0 | 1 | 0 | 0 | 0 | 0 | 0 | 0 | 0 | 0 | 0 | 0 | 0 |

Fig. 19B

Codebook 1 for the 140-gene experiments

| Genes | Codewords |
|---|---|
| THBS1 | 0 0 0 0 1 1 1 0 0 0 0 0 0 1 0 |
| FLNA | 0 0 0 0 1 0 1 0 0 0 0 1 0 0 0 1 |
| TNC | 1 0 0 0 1 0 1 0 0 0 0 0 1 0 0 0 |
| FBN2 | 0 0 1 0 1 0 1 1 0 0 0 0 0 0 0 0 |
| KIAA1199 | 0 0 0 0 1 1 0 1 0 0 0 1 0 0 0 0 |
| COL5A1 | 0 0 0 0 0 1 0 0 1 1 0 0 0 0 1 0 |
| MALAT1 | 0 0 0 0 0 1 1 0 1 0 0 0 1 0 0 0 |
| TLN1 | 0 0 0 0 1 0 0 0 0 0 1 0 0 1 1 0 |
| FBN1 | 0 0 1 0 0 1 0 1 0 0 0 0 0 0 1 0 |
| SRRM2 | 0 0 1 0 0 0 1 0 0 0 0 0 0 0 1 1 |
| TEAD1 | 0 0 1 0 0 1 1 0 0 0 0 1 0 0 0 0 |
| IQGAP1 | 0 0 0 0 0 0 1 1 0 0 0 1 0 0 1 0 |
| MYH10 | 0 0 1 0 1 0 0 0 0 0 0 1 0 0 1 0 |
| PAPPA | 0 0 0 1 0 1 0 0 0 0 1 0 0 0 1 0 |
| NR4A1 | 0 0 0 1 1 0 1 0 0 0 1 0 0 0 0 0 |
| LRP1 | 0 0 0 0 0 1 1 0 0 0 1 0 0 1 0 0 |
| SLC38A1 | 1 0 0 0 1 0 0 0 0 1 0 0 0 0 1 0 |
| SMARCA5 | 0 0 0 0 0 1 1 1 0 0 0 0 0 0 0 1 |
| CKAP5 | 0 1 0 0 0 0 1 0 0 0 1 0 0 0 1 0 |
| PIEZO1 | 1 0 0 0 1 1 0 0 1 0 0 0 0 0 0 0 |
| VCAN | 0 0 0 0 1 0 1 0 1 1 0 0 0 0 0 0 |
| PRRC2B | 0 1 0 1 0 1 1 0 0 0 0 0 0 0 0 0 |
| SON | 1 0 0 0 0 1 0 0 0 0 0 0 1 0 1 0 |
| SLC7A11 | 1 0 0 0 0 0 1 0 1 0 0 0 0 0 1 0 |
| GPR107 | 0 1 0 0 0 1 0 0 0 0 0 0 0 1 1 0 |
| KIAA1462 | 0 1 0 1 1 0 0 0 0 0 0 0 0 0 1 0 |
| notarget001 | 0 0 0 0 1 0 0 0 1 0 0 0 1 0 1 0 |
| blank001 | 0 1 0 0 1 1 0 0 0 0 1 0 0 0 0 0 |
| ROCK2 | 0 1 0 0 1 0 1 0 0 0 0 0 0 1 0 0 |
| SPTBN1 | 0 0 0 1 1 1 0 0 0 0 0 0 0 1 0 0 |
| FLNC | 0 0 0 1 0 0 1 0 0 0 0 0 0 1 1 0 |
| PRPF8 | 0 0 0 0 0 1 0 0 0 0 0 1 0 0 1 1 |
| IGF2R | 0 0 0 0 1 1 0 0 1 0 0 1 0 0 0 0 |
| FOSB | 1 0 0 0 0 1 1 0 0 1 0 0 0 0 0 0 |
| UBR5 | 0 0 0 0 1 0 0 1 0 0 0 0 0 0 1 1 |
| SVEP1 | 0 0 0 0 0 0 1 0 0 1 0 0 1 0 1 0 |
| CBX5 | 0 0 1 0 1 1 0 0 0 0 0 0 0 0 0 1 |
| PDS5A | 1 1 0 0 1 0 0 0 0 0 0 0 0 0 0 1 |
| NUMA1 | 0 0 0 0 0 0 1 0 0 1 1 0 0 0 0 1 |
| PLXNA1 | 0 0 0 1 0 0 0 0 0 0 0 0 1 1 0 1 0 |

Fig. 20A

Codebook 1 for the 140-gene experiments

| Genes | Codewords |
|---|---|
| ALPK2 | 0 1 0 0 0 1 0 0 0 1 0 1 0 0 0 0 |
| AFAP1 | 0 0 0 0 0 0 1 0 1 0 1 1 0 0 0 0 |
| SPTAN1 | 0 0 1 1 1 0 0 0 0 0 0 0 1 0 0 0 |
| DOCK7 | 0 1 1 0 0 0 0 0 0 0 0 1 0 1 0 |
| NOTCH2 | 0 0 0 0 0 0 0 1 0 0 0 0 1 1 1 |
| DYNC1H1 | 1 0 0 0 1 0 0 0 0 0 0 1 0 1 0 0 |
| ITGA2 | 1 0 1 0 0 0 0 0 0 0 0 0 0 1 1 0 |
| PRKDC | 0 0 0 1 1 0 0 0 1 0 0 0 0 0 0 1 |
| GTF3C1 | 0 0 1 0 0 1 0 0 0 0 0 0 1 1 0 0 |
| THSD4 | 0 0 0 0 0 1 0 0 0 1 0 0 0 1 0 1 |
| PTPN14 | 0 1 0 0 1 0 0 1 0 1 0 0 0 0 0 0 |
| LUZP1 | 0 0 0 0 1 0 0 0 1 0 1 0 0 0 0 1 |
| AMOTL1 | 1 0 0 0 0 0 1 1 0 0 1 0 0 0 0 0 |
| MAN1A2 | 1 0 1 0 1 0 0 0 0 0 1 0 0 0 0 0 |
| notarget002 | 1 0 0 1 1 0 0 1 0 0 0 0 0 0 0 0 |
| blank002 | 1 1 0 0 0 0 0 1 0 0 0 0 0 0 1 0 |
| USP9X | 0 0 0 0 1 0 0 0 0 1 1 1 0 0 0 0 |
| CREBBP | 0 1 0 0 0 0 1 0 0 0 0 0 0 1 0 0 1 |
| KPNA4 | 0 1 1 0 0 0 1 0 0 1 0 0 0 0 0 0 |
| EGFR | 0 0 0 1 0 0 1 0 0 1 0 1 0 0 0 0 |
| ZC3H13 | 0 0 0 1 0 0 1 1 0 0 0 0 1 0 0 0 |
| TNRC6A | 0 0 0 1 0 1 0 1 1 0 0 0 0 0 0 0 |
| TPR | 0 0 0 0 0 1 0 0 1 0 0 1 0 1 0 0 |
| COL7A1 | 0 0 0 1 0 1 0 0 0 0 0 0 1 0 0 1 |
| ASCC3 | 0 1 0 0 0 0 1 1 1 0 0 0 0 0 0 0 |
| USP34 | 0 0 0 0 0 0 0 0 0 1 0 1 0 1 1 |
| CENPF | 0 0 1 0 0 0 1 0 1 0 0 0 0 1 0 0 |
| KIDINS220 | 0 0 0 0 0 1 0 0 0 0 1 1 1 0 0 0 |
| SCUBE3 | 1 0 0 0 0 1 0 1 0 0 0 0 0 1 0 0 |
| NRIP1 | 0 0 0 0 0 0 0 0 0 1 0 1 0 1 1 0 |
| NUP98 | 1 0 0 1 0 0 0 0 0 0 0 0 0 0 1 1 |
| ZFC3H1 | 0 0 0 0 0 0 0 1 1 0 1 0 0 0 1 0 |
| FAM208B | 0 1 0 0 0 0 0 0 0 1 0 0 0 0 1 1 |
| RAB3B | 0 0 0 1 0 0 0 1 0 1 0 0 0 0 1 0 |
| AFF4 | 1 0 0 0 0 0 0 0 0 0 1 1 0 0 1 0 |
| PRKCA | 0 0 1 0 0 0 1 0 0 0 1 0 1 0 0 0 |
| FLNB | 1 0 0 0 0 0 1 0 0 0 0 0 0 1 0 1 |
| CHD8 | 1 0 0 0 0 1 0 0 0 0 1 0 0 0 0 1 |
| ANKRD52 | 0 1 0 0 1 0 0 0 0 0 0 0 1 1 0 0 0 |
| MKI67 | 0 0 0 0 0 0 1 0 0 0 0 1 1 1 0 0 |

Fig. 20B

Codebook 1 for the 140-gene experiments

| Genes | Codewords |
|---|---|
| DIP2C | 0 1 1 0 1 0 0 0 1 0 0 0 0 0 0 |
| SSH1 | 0 0 0 0 1 0 0 0 0 0 0 1 1 0 1 |
| notarget003 | 0 0 1 0 0 1 0 0 1 0 1 0 0 0 0 |
| blank003 | 1 1 1 0 0 1 0 0 0 0 0 0 0 0 0 |
| DNAJC13 | 0 0 0 0 1 0 0 1 1 0 0 0 0 1 0 0 |
| DSEL | 0 1 0 0 0 0 0 1 0 0 1 0 0 1 0 |
| PIK3CA | 0 0 0 0 1 0 1 0 1 1 0 0 0 0 0 |
| MED14 | 1 0 0 1 0 1 0 0 0 0 0 1 0 0 0 0 |
| HERC2 | 0 1 0 0 0 1 0 0 1 0 0 0 0 0 1 |
| H6PD | 0 0 1 1 0 0 0 0 1 0 0 0 0 0 1 0 |
| C14orf132 | 0 0 0 0 0 0 0 1 0 0 0 0 1 1 1 0 |
| SIPA1L3 | 0 0 0 0 0 0 1 1 0 1 0 0 0 1 0 0 |
| C17orf51 | 0 0 1 1 0 1 0 0 0 1 0 0 0 0 0 0 |
| NF1 | 0 0 0 1 0 0 1 0 1 0 0 0 0 0 0 1 |
| VPS13A | 1 1 0 0 0 0 1 0 0 0 0 1 0 0 0 0 |
| ABCA2 | 1 0 1 1 0 0 1 0 0 0 0 0 0 0 0 |
| PCNX | 0 1 0 0 0 1 0 1 0 0 0 0 1 0 0 0 |
| NKTR | 0 0 1 0 1 0 0 0 0 1 0 0 0 1 0 0 |
| FYCO1 | 0 0 0 1 1 0 0 0 1 0 0 1 0 0 0 0 |
| ATP11A | 0 0 1 0 0 0 0 0 0 1 1 0 0 0 1 0 |
| REV3L | 0 0 0 0 1 0 0 1 0 0 1 0 1 0 0 0 |
| CASC5 | 0 1 0 0 0 0 0 1 0 0 1 1 0 0 0 0 |
| AKAP11 | 0 1 0 1 0 0 0 0 0 0 0 1 0 0 1 0 0 |
| CEP250 | 0 0 1 0 0 0 0 0 0 1 0 0 1 0 0 1 |
| USP24 | 0 0 0 0 0 0 0 0 1 0 1 0 1 1 0 0 |
| AGPS | 1 0 0 0 0 0 0 0 0 0 1 1 0 0 1 |
| CBL | 1 0 1 0 0 0 0 0 0 1 0 1 0 0 0 0 |
| RNF169 | 0 0 0 1 0 0 0 0 0 0 1 1 0 0 0 1 |
| TMOD2 | 0 0 0 1 0 0 0 0 0 1 0 0 1 1 0 0 |
| FASN | 0 0 0 0 0 0 0 0 1 1 0 1 0 0 0 1 |
| notarget004 | 1 0 0 1 0 0 0 0 1 0 0 0 0 1 0 0 |
| blank004 | 0 0 1 0 0 0 0 0 1 0 0 1 1 0 0 0 |
| UBR2 | 0 1 1 0 0 0 0 0 0 0 1 0 0 0 0 1 |
| PHIP | 1 0 0 0 0 0 0 1 0 1 0 0 0 0 0 1 |
| GTF3C4 | 0 0 0 0 0 0 0 1 0 1 0 1 1 0 0 0 |
| QSER1 | 1 0 0 1 0 0 0 0 0 0 1 0 1 0 0 0 |
| VPS13D | 0 0 1 0 0 0 0 1 1 1 0 0 0 0 0 0 |
| FRY | 0 0 0 1 0 0 0 0 1 1 1 0 0 0 0 0 |
| DIP2B | 0 1 0 1 0 0 0 0 1 0 0 0 1 0 0 0 |
| HIVEP2 | 1 1 0 1 0 0 0 0 0 1 0 0 0 0 0 0 |

Fig. 20C

Codebook 1 for the 140-gene experiments

| Genes | Codewords |
|---|---|
| DOPEY1 | 1 0 0 0 0 0 0 1 1 0 0 1 0 0 0 |
| ALMS1 | 0 1 1 0 0 0 0 1 0 0 0 0 0 1 0 0 |
| HEATR5B | 0 0 1 1 0 0 0 1 0 0 1 0 0 0 0 0 |
| HIVEP1 | 0 0 1 0 0 0 0 1 0 0 0 1 0 0 0 1 |
| ARL10 | 0 1 0 1 0 0 0 1 0 0 0 0 0 0 0 1 |
| HELZ2 | 0 0 0 0 0 0 0 1 1 0 0 0 1 0 0 1 |
| POLQ | 1 0 1 0 0 0 0 0 1 0 0 0 0 0 0 1 |
| CACNA1A | 1 1 0 0 0 0 0 0 0 0 0 0 1 1 0 0 |
| KIAA2018 | 0 1 0 0 0 0 0 0 0 0 0 1 0 1 0 1 |
| LYST | 1 0 0 0 0 0 0 1 1 0 0 1 0 0 0 0 |
| ZKSCAN2 | 0 0 1 1 0 0 0 0 0 0 0 0 0 1 0 1 |
| DIEXF | 0 0 0 1 0 0 0 1 0 0 0 1 0 1 0 0 |
| FZD4 | 1 0 1 0 0 0 0 1 0 0 0 0 1 0 0 0 |
| SLC5A3 | 0 1 1 1 0 0 0 0 0 0 0 1 0 0 0 0 |
| KIAA1147 | 1 1 0 0 0 0 0 0 1 0 1 0 0 0 0 0 |
| LMTK2 | 0 1 0 0 0 0 0 0 0 1 1 0 1 0 0 0 |
| STARD9 | 0 0 1 0 0 0 0 0 0 0 1 1 0 1 0 0 |
| BRCA2 | 0 0 0 0 0 0 0 1 0 0 1 0 0 1 0 1 |
| notarget005 | 1 0 0 0 0 0 0 0 1 1 0 0 1 0 0 |
| blank005 | 1 1 0 0 0 0 0 0 1 0 1 0 0 0 0 0 |

Fig. 20D

Codebook 2 (shu"ed) for the 140-gene experiments

| Genes | Codewords |
|---|---|
| THBS1 | 0 0 0 0 1 0 0 0 0 0 0 1 1 0 1 |
| FLNA | 0 0 0 0 1 1 0 0 0 1 0 0 1 0 0 0 |
| TNC | 1 0 0 0 0 0 1 0 0 0 0 0 0 1 0 1 |
| FBN2 | 0 1 0 0 0 0 0 0 0 0 0 1 0 1 0 1 |
| KIAA1199 | 0 0 0 0 0 0 0 0 0 1 0 1 0 1 1 |
| COL5A1 | 0 0 0 0 0 0 0 1 0 0 0 0 1 1 1 0 |
| MALAT1 | 0 0 0 0 0 0 0 0 1 0 0 0 0 1 1 1 |
| TLN1 | 0 0 0 1 0 0 0 0 0 1 0 0 1 1 0 0 |
| FBN1 | 1 0 0 0 1 0 0 0 0 0 0 0 1 0 1 0 0 |
| SRRM2 | 0 0 0 0 1 0 0 1 0 0 0 0 0 0 1 1 |
| TEAD1 | 1 1 0 0 0 0 0 0 0 0 0 0 1 1 0 0 |
| IQGAP1 | 0 0 1 0 1 1 0 0 0 0 0 0 0 0 0 1 |
| MYH10 | 0 0 0 1 1 0 0 0 0 1 0 0 0 0 0 1 |
| PAPPA | 0 0 0 0 1 0 0 1 0 0 1 0 1 0 0 0 |
| NR4A1 | 0 0 0 0 1 0 0 0 1 0 1 0 0 0 0 1 |
| LRP1 | 0 0 0 0 0 0 0 1 0 1 0 1 1 0 0 |
| SLC38A1 | 0 0 0 0 0 1 0 0 0 1 0 0 0 1 0 1 |
| SMARCA5 | 0 0 1 0 0 0 0 0 0 1 0 0 1 0 0 1 |
| CKAP5 | 0 0 1 0 0 1 0 0 0 0 0 0 1 1 0 0 |
| PIEZO1 | 0 0 0 0 0 0 0 1 0 0 1 0 0 1 0 1 |
| VCAN | 0 0 0 0 0 0 1 0 0 0 0 1 1 1 0 0 |
| PRRC2B | 1 0 0 0 0 0 0 0 0 0 0 1 1 0 0 1 |
| SON | 0 0 1 0 1 0 0 0 1 0 0 0 1 0 0 |
| SLC7A11 | 0 1 0 0 1 0 1 0 0 0 0 0 0 1 0 0 |
| GPR107 | 0 0 0 0 1 0 1 0 0 0 0 1 0 0 0 1 |
| KIAA1462 | 0 0 1 1 1 0 0 0 0 0 0 0 1 0 0 0 |
| notarget001 | 1 1 0 0 1 0 0 0 0 0 0 0 0 0 0 1 |
| blank001 | 1 0 0 0 1 0 1 0 0 0 0 0 1 0 0 0 |
| ROCK2 | 0 1 0 0 0 0 1 0 0 0 0 0 1 0 0 1 |
| SPTBN1 | 0 0 0 0 1 0 0 0 0 0 1 0 0 1 1 0 |
| FLNC | 0 0 0 0 1 0 0 0 1 0 0 0 1 0 1 0 |
| PRPF8 | 0 0 0 0 0 0 1 1 0 0 0 1 0 0 1 |
| IGF2R | 0 0 0 1 1 1 0 0 0 0 0 0 0 1 0 0 |
| FOSB | 0 0 1 1 0 0 0 0 0 0 0 0 0 1 0 1 |
| UBR5 | 0 1 0 0 1 0 0 0 0 0 0 1 1 0 0 0 |
| SVEP1 | 0 0 0 0 1 0 0 1 1 0 0 0 0 1 0 0 |
| CBX5 | 0 0 0 1 0 1 0 0 0 0 0 0 1 0 0 1 |
| PDS5A | 1 0 0 1 1 0 0 1 0 0 0 0 0 0 0 0 |
| NUMA1 | 0 1 0 0 0 1 0 1 0 0 0 0 1 0 0 0 |
| PLXNA1 | 0 1 0 1 0 0 0 0 0 0 1 0 0 1 0 0 |

Fig. 20E

Codebook 2 (shuffled) for the 140-gene experiments

| Genes | Codewords |
|---|---|
| ALPK2 | 0 1 1 0 0 0 0 0 0 0 0 1 0 1 0 |
| AFAP1 | 1 0 0 0 0 0 0 0 1 1 0 0 1 0 0 |
| SPTAN1 | 0 0 0 0 0 0 0 0 1 0 1 0 1 1 0 |
| DOCK7 | 0 0 1 0 0 0 0 0 0 1 1 0 1 0 0 |
| NOTCH2 | 0 0 0 0 1 1 0 1 0 0 0 1 0 0 0 |
| DYNC1H1 | 0 1 1 0 1 0 0 0 1 0 0 0 0 0 0 |
| ITGA2 | 0 0 0 1 1 0 0 0 1 0 0 1 0 0 0 0 |
| PRKDC | 0 0 0 0 0 0 0 0 1 1 0 1 0 0 0 1 |
| GTF3C1 | 0 0 1 0 1 0 0 0 0 0 0 1 0 0 1 0 |
| THSD4 | 1 0 0 0 0 0 0 1 0 1 0 0 0 0 0 1 |
| PTPN14 | 0 0 0 0 0 0 1 1 0 1 0 0 0 1 0 0 |
| LUZP1 | 1 0 1 0 0 0 0 0 0 0 0 0 1 1 0 |
| AMOTL1 | 0 0 0 0 1 0 1 0 1 1 0 0 0 0 0 0 |
| MAN1A2 | 0 1 0 1 0 0 0 1 0 0 0 0 0 0 0 1 |
| notarget002 | 1 0 0 0 0 1 0 0 0 0 0 0 1 0 1 0 |
| blank002 | 1 0 0 1 0 0 0 0 1 0 0 0 0 1 0 0 |
| USP9X | 0 0 0 0 0 0 1 0 1 0 1 1 0 0 0 |
| CREBBP | 0 1 0 0 0 1 0 0 1 0 0 0 0 0 0 1 |
| KPNA4 | 1 0 0 1 0 0 0 0 0 0 0 0 0 0 1 1 |
| EGFR | 1 0 0 0 0 1 0 0 0 0 1 0 0 0 0 1 |
| ZC3H13 | 1 0 0 0 1 1 0 0 1 0 0 0 0 0 0 0 |
| TNRC6A | 0 0 0 0 1 0 0 0 0 1 1 1 0 0 0 0 |
| TPR | 1 0 1 0 0 0 0 1 0 0 0 0 1 0 0 0 |
| COL7A1 | 0 0 1 0 0 0 0 1 0 0 0 1 0 0 0 1 |
| ASCC3 | 0 1 0 0 1 0 0 1 0 1 0 0 0 0 0 0 |
| USP34 | 0 0 1 0 0 0 1 0 0 0 1 0 1 0 0 0 |
| CENPF | 0 0 1 0 0 0 0 0 1 0 0 1 1 0 0 0 |
| KIDINS220 | 0 0 0 1 0 0 0 0 0 0 1 1 0 0 0 1 |
| SCUBE3 | 0 0 0 0 0 0 1 0 0 1 1 0 0 0 0 1 |
| NRIP1 | 0 0 0 1 1 0 1 0 0 0 1 0 0 0 0 0 |
| NUP98 | 0 0 0 0 0 1 0 0 0 0 1 1 1 0 0 0 |
| ZFC3H1 | 0 0 0 1 0 0 1 0 1 0 0 0 0 0 0 1 |
| FAM208B | 0 1 0 1 1 0 0 0 0 0 0 0 0 0 1 0 |
| RAB3B | 0 0 0 1 0 0 0 0 0 0 0 1 1 0 1 0 |
| AFF4 | 0 1 0 0 0 0 0 0 0 1 0 0 0 0 1 1 |
| PRKCA | 0 1 0 0 0 1 0 0 0 0 0 0 0 1 1 0 |
| FLNB | 0 1 0 0 0 0 0 0 1 1 0 0 0 1 0 0 |
| CHD8 | 0 0 0 0 0 1 0 0 0 0 0 1 0 0 1 1 |
| ANKRD52 | 0 0 1 0 0 0 1 0 0 0 0 0 0 0 1 1 |
| MKI67 | 0 1 0 0 1 1 0 0 0 0 1 0 0 0 0 0 |

Fig. 20F

Codebook 2 (shu"ed) for the 140-gene experiments

| Genes | Codewords |
|---|---|
| DIP2C | 1 0 1 0 1 0 0 0 0 0 1 0 0 0 0 0 |
| SSH1 | 0 1 0 1 0 0 0 0 1 0 0 0 1 0 0 0 |
| notarget003 | 0 1 1 0 0 0 0 0 0 1 0 0 0 0 0 1 |
| blank003 | 0 0 0 0 1 1 1 0 0 0 0 0 0 0 1 0 |
| DNAJC13 | 0 0 0 1 0 0 1 1 0 0 0 0 1 0 0 0 |
| DSEL | 0 0 0 1 0 0 0 1 0 0 0 1 0 1 0 0 |
| PIK3CA | 0 0 0 0 0 1 1 0 0 0 1 0 0 1 0 0 |
| MED14 | 0 0 0 0 0 1 1 1 0 0 0 0 0 0 0 1 |
| HERC2 | 1 0 0 0 1 0 0 0 0 1 0 0 0 0 1 0 |
| H6PD | 0 0 1 0 0 0 1 0 1 0 0 0 0 1 0 0 |
| C14orf132 | 0 0 0 0 0 1 0 0 1 0 0 1 0 1 0 0 |
| SIPA1L3 | 1 0 1 0 0 0 0 0 1 0 0 0 0 0 0 1 |
| C17orf51 | 0 1 0 0 0 0 0 0 0 1 1 0 1 0 0 0 |
| NF1 | 1 0 0 0 0 0 0 0 1 1 0 0 1 0 0 0 |
| VPS13A | 0 0 1 0 1 0 1 1 0 0 0 0 0 0 0 0 |
| ABCA2 | 0 0 0 0 0 0 1 0 0 1 0 0 1 0 1 0 |
| PCNX | 0 0 0 1 0 0 1 0 0 0 0 0 0 1 1 0 |
| NKTR | 0 1 1 0 0 0 0 1 0 0 0 0 0 1 0 0 |
| FYCO1 | 0 0 0 0 1 1 0 1 0 0 0 1 0 0 0 0 |
| ATP11A | 1 0 0 1 0 0 0 0 0 0 1 0 1 0 0 0 |
| REV3L | 1 0 0 0 0 1 0 1 0 0 0 0 0 1 0 0 |
| CASC5 | 0 0 0 0 0 1 0 1 0 1 1 0 0 0 0 0 |
| AKAP11 | 0 0 1 0 0 1 0 0 1 0 1 0 0 0 0 0 |
| CEP250 | 1 0 1 0 0 0 0 0 0 1 0 1 0 0 0 0 |
| USP24 | 1 1 0 1 0 0 0 0 0 1 0 0 0 0 0 0 |
| AGPS | 1 0 0 0 0 0 0 0 0 0 1 1 0 0 1 0 |
| CBL | 0 1 0 0 0 0 1 1 1 0 0 0 0 0 0 0 |
| RNF169 | 0 0 1 1 0 0 0 1 0 0 1 0 0 0 0 0 |
| TMOD2 | 0 0 1 0 0 1 0 1 0 0 0 0 0 0 1 0 |
| FASN | 0 0 0 0 0 0 1 1 0 0 0 1 0 0 1 0 |
| notarget004 | 0 1 1 0 0 0 1 0 0 1 0 0 0 0 0 0 |
| blank004 | 1 1 0 0 0 0 0 1 0 0 0 0 0 0 1 0 |
| UBR2 | 0 1 0 0 0 0 0 0 1 0 0 1 0 0 1 0 |
| PHIP | 0 0 1 0 0 1 1 0 0 0 0 1 0 0 0 0 |
| GTF3C4 | 0 1 0 0 0 0 1 0 0 0 1 0 0 0 1 0 |
| QSER1 | 1 0 0 0 0 0 1 1 0 0 1 0 0 0 0 0 |
| VPS13D | 1 1 0 0 0 0 0 1 0 0 0 0 1 0 0 0 |
| FRY | 1 0 0 0 0 0 1 0 1 0 0 0 0 0 1 0 |
| DIP2B | 0 1 0 0 0 1 0 0 0 1 0 1 0 0 0 0 |
| HIVEP2 | 1 0 1 1 0 0 1 0 0 0 0 0 0 0 0 0 |

Fig. 20G

Codebook 2 (shuffled) for the 140-gene experiments

| Genes | Codewords |
|---|---|
| DOPEY1 | 0 0 1 1 0 0 0 0 1 0 0 0 0 0 1 0 |
| ALMS1 | 0 0 1 1 0 1 0 0 0 1 0 0 0 0 0 0 |
| HEATR5B | 0 0 1 0 0 0 0 1 1 1 0 0 0 0 0 0 |
| HIVEP1 | 0 0 0 1 0 1 0 0 0 0 1 0 0 0 1 0 |
| ARL10 | 0 0 0 0 0 1 0 0 1 1 0 0 0 0 1 0 |
| HELZ2 | 0 0 0 1 0 0 0 1 0 1 0 0 0 0 1 0 |
| POLQ | 0 0 0 0 0 0 1 0 1 0 1 1 0 0 0 0 |
| CACNA1A | 1 0 0 0 0 1 1 0 0 1 0 0 0 0 0 0 |
| KIAA2018 | 0 0 0 0 0 0 0 1 1 0 1 0 0 0 1 0 |
| LYST | 0 0 0 1 0 1 0 1 1 0 0 0 0 0 0 0 |
| ZKSCAN2 | 0 1 0 1 0 1 1 0 0 0 0 0 0 0 0 0 |
| DIEXF | 0 1 0 0 0 0 0 1 0 0 1 1 0 0 0 0 |
| FZD4 | 0 0 0 1 0 0 1 0 0 1 0 1 0 0 0 0 |
| SLC5A3 | 1 0 0 0 0 0 0 1 1 0 0 1 0 0 0 0 |
| KIAA1147 | 0 0 1 0 0 0 0 0 0 1 1 0 0 0 1 0 |
| LMTK2 | 0 1 1 1 0 0 0 0 0 0 0 1 0 0 0 0 |
| STARD9 | 0 0 0 1 0 0 0 0 1 1 1 0 0 0 0 0 |
| BRCA2 | 1 0 0 1 0 1 0 0 0 0 0 1 0 0 0 0 |
| notarget005 | 1 1 1 0 0 1 0 0 0 0 0 0 0 0 0 0 |
| blank005 | 1 1 0 0 0 0 0 0 1 0 1 0 0 0 0 0 |

Fig. 20H

SYSTEMS AND METHODS FOR DETERMINING NUCLEIC ACIDS

RELATED APPLICATIONS

This application is a continuation of U.S. application Ser. No. 18/046,409, filed Oct. 13, 2022, entitled "Systems and Methods for Determining Nucleic Acids," which is a continuation of U.S. application Ser. No. 17/374,000, filed Jul. 13, 2021, entitled "Systems and Methods for Determining Nucleic Acids," which is a divisional of U.S. application Ser. No. 15/329,683, filed Jan. 27, 2017, entitled "Systems and Methods for Determining Nucleic Acids," which is a national stage filing of International Patent Application Serial No. PCT/US2015/042556, which claims the benefit of U.S. Provisional Patent Application Ser. No. 62/031,062, filed Jul. 30, 2014, entitled "Systems and Methods for Determining Nucleic Acids," by Zhuang, et al.; U.S. Provisional Patent Application Ser. No. 62/142,653, filed Apr. 3, 2015, entitled "Systems and Methods for Determining Nucleic Acids," by Zhuang, et al.; and U.S. Provisional Patent Application Ser. No. 62/050,636, filed Sep. 15, 2014, entitled "Probe Library Construction," by Zhuang, et al. Each of the above is incorporated herein by reference.

GOVERNMENT FUNDING

This invention was made with government support under Grant No. GM096450 awarded by National Institutes of Health. The government has certain rights in the invention.

REFERENCE TO AN ELECTRONIC SEQUENCE LISTING

The contents of the electronic sequence listing (H049870509US05-SUBSEQ-TC.xml; Size: 52,324 bytes; and Date of Creation: Jun. 5, 2023) is herein incorporated by reference in its entirety.

FIELD

The present invention generally relates to systems and methods for imaging or determining nucleic acids, for instance, within cells. In some embodiments, the transcriptome of a cell may be determined.

BACKGROUND

Single-molecule fluorescent in situ hybridization (smFISH) is a powerful method for detecting individual mRNA molecules in cells. The high detection efficiency and large dynamic range of this method provides exquisite detail into the expression state, spatial distribution within cells and intact tissues, and variation among cells of individual mRNAs. Such approaches have been essential to many recent insights into understanding gene regulation and expression. A fundamental limitation of smFISH, however, is its low throughput, typically only a few genes at a time. This low throughput is due to a lack of distinguishable probes with which to label cells and the cost of producing large amounts of labeled probe required for high efficiency staining. Thus, improvements in detecting mRNA molecules are needed.

SUMMARY

The present invention generally relates to systems and methods for imaging or determining nucleic acids, for instance, within cells. In some embodiments, the transcriptome of a cell may be determined. The subject matter of the present invention involves, in some cases, interrelated products, alternative solutions to a particular problem, and/or a plurality of different uses of one or more systems and/or articles.

In one aspect, the present invention is generally directed to a composition. According to one set of embodiments, the composition comprises a plurality of nucleic acid probes, at least some of which comprise a first portion comprising a target sequence and a plurality of read sequences. In some cases, each comprises a first portion comprising a target sequence and a plurality of read sequences. In some embodiments, the plurality of read sequences are distributed on the plurality of nucleic acid probes so as to define an error-correcting code.

In another aspect, the present invention is generally directed to a method. In one set of embodiments, the method includes acts of exposing a sample to a plurality of nucleic acid probes; for each of the nucleic acid probes, determining binding of the nucleic acid probes within the sample; creating codewords based on the binding of the nucleic acid probes; and for at least some of the codewords, matching the codeword to a valid codeword wherein, if no match is found, applying error correction to the codeword to form a valid codeword.

The method, in another set of embodiments, includes acts of exposing a sample to a plurality of nucleic acid probes, wherein the nucleic acid probes comprise a first portion comprising a target sequence and a second portion comprising one or more read sequences, and wherein at least some of the plurality of nucleic acid probes comprises distinguishable nucleic acid probes formed from combinatorial combination of one or more read sequences taken from a plurality of read sequences; and for each of the nucleic acid probes, determining binding of the target sequences of the nucleic acid probes within the sample.

In yet another set of embodiments, the method includes acts of exposing a sample to a plurality of primary nucleic acid probes (also called encoding probes); exposing the plurality of primary nucleic acid probes to a sequence of secondary nucleic acid probes (also called readout probes) and determining fluorescence of each of the secondary nucleic acid probes within the sample; creating codewords based on fluorescence of the secondary nucleic acid probes; and for at least some of the codewords, matching the codeword to a valid codeword wherein, if no match is found, applying error correction to the codeword to form a valid codeword.

In one set of embodiments, the method includes acts of exposing a plurality of primary nucleic acid probes to a sample; and exposing the plurality of nucleic acid probes to a sequence of secondary nucleic acid probes and determining fluorescence of each of the secondary probes within the sample. In some embodiments, at least some of the plurality of secondary nucleic acid probes comprises distinguishable secondary nucleic acid probes formed from combinatorial combination of one or more read sequences (or readout probe sequences) taken from a plurality of read sequences (or readout probe sequences).

In another set of embodiments, the method comprises acts of exposing a cell to a plurality of nucleic acid probes, exposing the plurality of nucleic acid probes to a first secondary probe comprising a first signaling entity, determining the first signaling entity at a precision better than 500 nm, inactivating the first signaling entity, exposing the plurality of nucleic acid probes to a second secondary probe comprising a second signaling entity, and determining the second signaling entity at a precision better than 500 nm.

In another set of embodiments, the method comprises acts of exposing a cell to a plurality of nucleic acid probes, exposing the plurality of nucleic acid probes to a first secondary probe comprising a first signaling entity, determining the first signaling entity at a resolution better than 100 nm, inactivating the first signaling entity, exposing the plurality of nucleic acid probes to a second secondary probe comprising a second signaling entity, and determining the second signaling entity at a resolution better than 100 nm.

The method, in yet another set of embodiments, includes acts of exposing a cell to a plurality of nucleic acid probes, exposing the plurality of nucleic acid probes to a first secondary probe comprising a first signaling entity, determining the first signaling entity using a super-resolution imaging technique, inactivating the first signaling entity, exposing the plurality of nucleic acid probes to a second secondary probe comprising a second signaling entity, and determining the second signaling entity using a super-resolution imaging technique.

In certain embodiments, the method comprises acts of associating a plurality of targets with a plurality of target sequences and a plurality of codewords, wherein the codewords comprise a number of positions and values for each position, and the codewords form an error-checking and/or error-correcting code space; associating a plurality of distinguishable read sequences with the plurality of codewords such that each distinguishable read sequence represents a value of a position within the codewords; and forming a plurality of nucleic acid probes, each comprising a target sequence and one or more read sequences.

In addition, in one set of embodiments, the method includes acts of associating a plurality of targets with a plurality of target sequences and a plurality of codewords, wherein the codewords comprise a number of positions and values for each position, and the codewords form an error-checking and/or error-correcting code space; forming a plurality of nucleic acid probes each comprising a target sequence; and forming groups comprising the plurality of nucleic acid probes such that each group of nucleic acid probes corresponds to at least one common value of a position within the codewords.

In another set of embodiments, the method includes acts of associating a plurality of targets with a plurality of target sequences and a plurality of codewords, wherein the codewords comprise a number of positions that is less than the number of targets, and wherein each codeword is associated with a single target, associating a plurality of distinguishable read sequences with the plurality of codewords such that each distinguishable read sequence represents a value of a position within the codewords, and forming a plurality of nucleic acid probes, each comprising a target sequence and one or more read sequences.

The method, in still another set of embodiments, includes acts of exposing a plurality of nucleic acid probes to a cell, exposing the plurality of nucleic acid probes to a sequence of secondary probes and determining fluorescence of each of the secondary probes within the cell, and based on the sequence of fluorescence of each of the secondary probes, determining nucleic acids within the cell.

In another set of embodiments, the method includes acts of associating a plurality of targets with a plurality of target sequences and a plurality of codewords, wherein the codewords comprise a number of positions and values for each position, and the codewords form an error-checking and/or error-correcting code space; forming a plurality of nucleic acid probes each comprising a target sequence; and forming groups comprising the plurality of nucleic acid probes such that each group of nucleic acid probes correspond to at least one common value of a position within the codewords.

In yet another set of embodiments, the method includes acts of exposing a cell to a plurality of nucleic acid probes, exposing the plurality of nucleic acid probes to a first secondary probe comprising a first signaling entity, determining the first signaling entity using a super-resolution imaging technique, inactivating the first signaling entity, exposing the plurality of nucleic acid probes to a second secondary probe comprising a second signaling entity, and determining the second signaling entity using a super-resolution imaging technique.

In still another set of embodiments, the method includes acts of exposing a cell to a plurality of nucleic acid probes, exposing the plurality of nucleic acid probes to a first secondary probe comprising a first signaling entity, determining the first signaling entity at a precision better than 500 nm, inactivating the first signaling entity, exposing the plurality of nucleic acid probes to a second secondary probe comprising a second signaling entity, and determining the second signaling entity at a precision better than 500 nm.

In still another set of embodiments, the method includes acts of exposing a cell to a plurality of nucleic acid probes, exposing the plurality of nucleic acid probes to a first secondary probe comprising a first signaling entity, determining the first signaling entity at a resolution better than 100 nm, inactivating the first signaling entity, exposing the plurality of nucleic acid probes to a second secondary probe comprising a second signaling entity, and determining the second signaling entity using a super-resolution imaging technique.

In still another set of embodiments, the method includes acts of associating a plurality of nucleic acid targets with a plurality of target sequences and a plurality of codewords, wherein the codewords comprise a number of positions and values for each position, and the codewords form an error-checking and/or error-correcting code; associating unique read sequences with each possible value of each position in the codewords, wherein the read sequences are taken from a set of orthogonal sequences, which have limited homology with one another and with the nucleic acid species in a sample; forming a plurality of primary nucleic acid probes each comprising a target sequence that uniquely binds to a nucleic acid target and one or more read sequences; forming a plurality of secondary nucleic acid probes comprising a signaling entity and a sequence that is complementary to one of the read sequences; exposing a sample to the primary nucleic acid probes such that the nucleic acid probes hybridize to the nucleic acid targets in the sample; exposing the primary nucleic acid probes in the sample to a secondary nucleic acid probe such that the secondary nucleic acid probe hybridizes to the read sequence on at least some of the primary nucleic acid probes; imaging the sample; and repeating the exposing and imaging steps one or more times, using a different secondary nucleic acid probe for at least some of the repetitions.

The method, according to yet another set of embodiments, includes acts of associating a plurality of nucleic acid targets with a plurality of target sequences and a plurality of codewords wherein the codewords comprise a number of positions and values for each position, and the codewords form an error-checking and/or error-correcting code space; forming a plurality of nucleic acid probes comprising a signaling entity and a target sequence that uniquely binds to one of the nucleic acid targets; grouping the nucleic acid probes into a plurality of probe pools, wherein each of the probe pools corresponds to a specific value of a unique position within the codewords; exposing a sample to one of the probe pools; imaging the sample; and repeating the exposing and imaging steps one or more times, using a different probe pool for at least some of the repetitions.

In another aspect, the present invention encompasses methods of making one or more of the embodiments described herein. In still another aspect, the present invention encompasses methods of using one or more of the embodiments described herein.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures:

FIGS. 12A-12C show schematic descriptions of Hamming distance, in another embodiment of the invention;

FIGS. 19A-19D illustrate decoding and error assessment, in another embodiment of the invention; and FIGS. 20A-20H show the codebooks for certain experiments in another embodiment.

BRIEF DESCRIPTION OF THE SEQUENCES

Figure 1A:
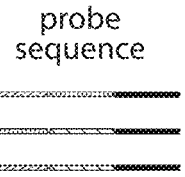
FIGS. 1A-1C illustrates an encoding scheme for nucleic acid probes, in certain embodiments of the invention.

```
SEQ ID NO: 1 is:
GTTGGCGACGAAAGCACTGCGATTGGAACCGTC

CCAAGCGTTGCGCTTAATGGA

TCATCAATTTTGTCTCACTACGACGGTCAATCG

CGCTGCATACTTGCGTCGGTCGGACAAACGAGG;

SEQ ID NO: 2 is
CGCAACGCTTGGGACGGTTCCAATCGGATC;

SEQ ID NO: 3 is
CGAATGCTCTGGCCTCGAACGAACGATAGC;

SEQ ID NO: 4 is
ACAAATCCGACCAGATCGGACGATCATGGG;

SEQ ID NO: 5 is
CAAGTATGCAGCGCGATTGACCGTCTCGTT;

SEQ ID NO: 6 is
TGCGTCGTCTGGCTAGCACGGCACGCAAAT;

SEQ ID NO: 7 is
AAGTCGTACGCCGATGCGCAGCAATTCACT;

SEQ ID NO: 8 is
CGAAACATCGGCCACGGTCCCGTTGAACTT;

SEQ ID NO: 9 is
ACGAATCCACCGTCCAGCGCGTCAAACAGA;

SEQ ID NO: 10 is
CGCGAAATCCCCGTAACGAGCGTCCCTTGC;

SEQ ID NO: 11 is
GCATGAGTTGCCTGGCGTTGCGACGACTAA;

SEQ ID NO: 12 is
CCGTCGTCTCCGGTCCACCGTTGCGCTTAC;

SEQ ID NO: 13 is
GGCCAATGGCCCAGGTCCGTCACGCAATTT;

SEQ ID NO: 14 is
TTGATCGAATCGGAGCGTAGCGGAATCTGC;

SEQ ID NO: 15 is
CGCGCGGATCCGCTTGTCGGGAACGGATAC;

SEQ ID NO: 16 is
GCCTCGATTACGACGGATGTAATTCGGCCG;
```

-continued

SEQ ID NO: 17 is
GCCCGTATTCCCGCTTGCGAGTAGGGCAAT

SEQ ID NO: 18 is
GTTGGTCGGCACTTGGGTGC;

SEQ ID NO: 19 is
CGATGCGCCAATTCCGGTTC;

SEQ ID NO: 20 is
CGCGGGCTATATGCGAACCG;

SEQ ID NO: 21 is
TAATACGACTCACTATAGGGAAAGCCGGTTCATCCGGTGG;

SEQ ID NO: 22 is
TAATACGACTCACTATAGGGTGATCATCGCTCGCGGGTTG;

SEQ ID NO: 23 is
TAATACGACTCACTATAGGGCGTGGAGGGCATACAACGC;

SEQ ID NO: 24 is
CGCAACGCTTGGGACGGTTCCAATCGGATC/3Cy5Sp/;

SEQ ID NO: 25 is
CGAATGCTCTGGCCTCGAACGAACGATAGC/3Cy5Sp/;

SEQ ID NO: 26 is
ACAAATCCGACCAGATCGGACGATCATGGG/3Cy5Sp/;

SEQ ID NO: 27 is
CAAGTATGCAGCGCGATTGACCGTCTCGTT/3Cy5Sp/;

SEQ ID NO: 28 is
GCGGGAAGCACGTGGATTAGGGCATCGACC/3Cy5Sp/;

SEQ ID NO: 29 is
AAGTCGTACGCCGATGCGCAGCAATTCACT/3Cy5Sp/;

SEQ ID NO: 30 is
CGAAACATCGGCCACGGTCCCGTTGAACTT/3Cy5Sp/;

SEQ ID NO: 31 is
ACGAATCCACCGTCCAGCGCGTCAAACAGA/3Cy5Sp/;

SEQ ID NO: 32 is
CGCGAAATCCCCGTAACGAGCGTCCCTTGC/3Cy5Sp/;

SEQ ID NO: 33 is
GCATGAGTTGCCTGGCGTTGCGACGACTAA/3Cy5Sp/;

SEQ ID NO: 34 is
CCGTCGTCTCCGGTCCACCGTTGCGCTTAC/3Cy5Sp/;

SEQ ID NO: 35 is
GGCCAATGGCCCAGGTCCGTCACGCAATTT/3Cy5Sp/;

SEQ ID NO: 36 is
TTGATCGAATCGGAGCGTAGCGGAATCTGC/3Cy5Sp/;

SEQ ID NO: 37 is
CGCGCGGATCCGCTTGTCGGGAACGGATAC/3Cy5Sp/;

SEQ ID NO: 38 is
GCCTCGATTACGACGGATGTAATTCGGCCG/3Cy5Sp/;
and

SEQ ID NO: 39 is
GCCCGTATTCCCGCTTGCGAGTAGGGCAAT/3Cy5Sp/.

DETAILED DESCRIPTION

The present invention generally relates to systems and methods for imaging or determining nucleic acids, for instance, within cells. In some embodiments, the transcriptome of a cell may be determined. Certain embodiments are directed to determining nucleic acids, such as mRNA, within cells at relatively high resolutions. In some embodiments, a plurality of nucleic acid probes may be applied to a sample, and their binding within the sample determined, e.g., using fluorescence, to determine locations of the nucleic acid probes within the sample. In some embodiments, codewords may be based on the binding of the plurality of nucleic acid probes, and in some cases, the codewords may define an error-correcting code to reduce or prevent misidentification of the nucleic acids. In certain cases, a relatively large number of different targets may be identified using a relatively small number of labels, e.g., by using various combinatorial approaches.

Two example approaches are now discussed. It should be understood, however, that these are presented by way of explanation and not limitation; other aspects and embodiments are discussed in further detail herein. In one example method, primary probes (also called encoding probes) and secondary probes (also called readout probes) are used, where the primary probes encode "codewords" and bind to target nucleic acids in the sample, and the secondary probes are used to read out the codewords from the primary probes. In another example method, a plurality of different primary probes containing codewords are divided into as many separate pools as there are positions in the codewords, such that each primary probe pool corresponds to a certain value in a certain position of the codewords (e.g., a "one" in the first position as in "1001").

Figure 3A:
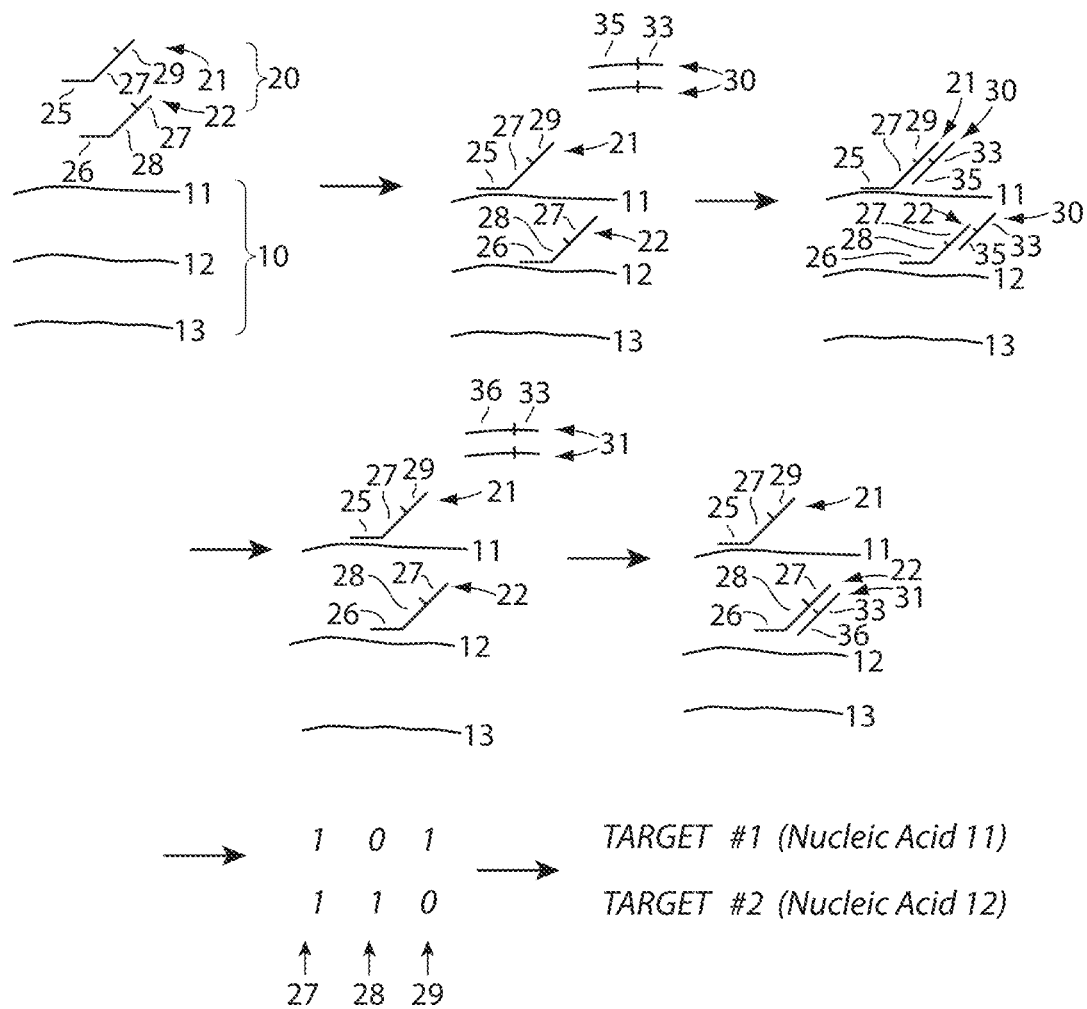
FIGS. 3A-3B illustrate the determination of nucleic acids, in accordance with various embodiments of the invention.

The first example is now described with respect to FIG. 3A. As will be discussed in more detail below, in other embodiments, other configurations may be used as well. In this first example, a series of nucleic acid probes are used to determine nucleic acids within a cell or other sample, e.g., qualitatively or quantitatively. For example, nucleic acids may be identified as being present or absent, and/or the numbers or concentrations of certain nucleic acids may be determined within the cell or other sample. In some cases, the positions of the probes within the cell or other sample may be determined at relatively high resolutions, and in some cases, at resolutions better than the wavelength of visible light.

This example is generally directed to spatially detecting nucleic acids within a cell or other sample, e.g., at relatively high resolutions. For example, the nucleic acids may be mRNAs, or other nucleic acids described herein. In one set of embodiments, the nucleic acids within the cell may be determined by delivering or applying nucleic acid probes to the cell. In some cases, by using combinatorial approaches, a relatively large number of nucleic acids may be determined using a relatively small number of different labels on the nucleic acid probes. Thus, for example, a relatively small number of experiments may be used to determine a relatively large number of nucleic acids in a sample, e.g., due to simultaneous binding of the nucleic acid probes to different nucleic acids in the sample.

In one set of embodiments, a population of primary nucleic acid probes are applied to the cell (or other sample) that is able to bind nucleic acids suspected of being present within the cell. Afterwards, sequentially, secondary nucleic acid probes that can bind to or otherwise interact with some of the primary nucleic acids are added and determined, e.g., using imaging techniques such as fluorescence microscopy (e.g., conventional fluorescence microscopy), STORM (stochastic optical reconstruction microscopy) or other imaging techniques. After imaging, the secondary nucleic acid probes are inactivated or removed, and a different secondary nucleic acid probe is added to the sample. This may be repeated multiple times with multiple different secondary nucleic acid probes. The pattern of binding of the various secondary nucleic acid probes may be used to determine the primary nucleic acid probes at locations within the cell or other sample, which can be used to determine mRNA or other nucleic acids that are present.

For instance, as is shown in FIG. 3A, a population of nucleic acids 10 within a cell (represented here by nucleic acids 11, 12, and 13) may be exposed to a population of primary nucleic acid probes 20, including probes 21 and 22. The primary nucleic acid probes may contain, for instance, a target sequence that can recognize a nucleic acid (e.g., a sequence within nucleic acid 11). Probes 21 and 22 may contain the same or different targeting sequences, which may bind to or hybridize with the same or different nucleic acids. As an example, as is shown in FIG. 3A, probe 21 contains a first targeting sequence 25 which targets the probe to nucleic acid 11, while probe 22 contains a second targeting sequence 26, not identical to the first targeting sequence 25 and which targets the probe to nucleic acid 12. The target sequence may be substantially complementary to at least a portion of a target nucleic acid, and enough of the target sequence may be present such that specific binding of the nucleic acid probe to the target nucleic acid can occur.

Primary nucleic acid probes 20 may also contain one or more "read" sequences. Two such read sequences are used in this example, although in other embodiments, there may be one, three, four, or more read sequences present within a primary nucleic acid probe. The read sequences may all independently be the same or different. In addition, in one set of embodiments, different nucleic acid probes may use one or more common read sequences. For example, more than one read sequence may be combinatorially combined on different nucleic acid probes, thereby producing a relatively large number of different nucleic acid probes that can be separately identified, even though only a relatively small number of read sequences are used. Thus, for example, in FIG. 3A, probe 21 contains read sequences 27 and 29, while probe 22 contains read sequences 27 and 28, where the two read sequences 27 are identical, and different from read sequences 28 and 29.

After primary nucleic acid probes 20 have been introduced to the sample and allowed to interact with nucleic acids 11, 12, and 13, one or more secondary nucleic acid probes 30 may be applied to the sample to determine the primary nucleic acid probes. The secondary nucleic acid probes may contain a recognition sequence able to recognize one of the read sequences present within the population of primary nucleic acid probes. For instance, the recognition sequence may be substantially complementary to at least a portion of the read sequence, such that the secondary nucleic acid probe is able to bind to or hybridize with corresponding primary nucleic acid probe. For instance, in this example, recognition sequence 35 is able to recognize read sequence 27. In addition, the secondary nucleic acid probes may contain one or more signaling entities 33. For example, a signaling entity may be a fluorescent entity attached to the probe, or a certain sequence of nucleic acids that can be determined in some fashion. More than one secondary sequence may be used, e.g., sequentially. For example, as shown in this figure, the initial secondary probe 30 may be removed (e.g., as discussed below) and a new secondary probe 31 may be added, containing recognition sequence 36 able to recognize read sequence 28 and one or more signaling entities 33. This may also be repeated multiple times, e.g., to determine read sequence 29 or other read sequences that may be present.

The location of the secondary nucleic acid probes 30, 31, etc. may be determined by determining signaling entity 33. For example, if the signaling entity is fluorescent, then fluorescence microscopy can be used to determine the signaling entity. In some embodiments, imaging of a sample to determine the signaling entity may be used at relatively high resolutions, and in some cases, super-resolution imaging techniques (e.g., resolutions better than the wavelength of visible light or the diffraction limit of light) may be used. Examples of super-resolution imaging techniques include STORM, or other techniques as discussed herein. In some cases, e.g., with certain super-resolution imaging techniques such as STORM, more than one image of the sample may be acquired.

More than one type of secondary nucleic acid probe may be applied to a cell or other sample. For example, a first secondary nucleic acid probe may be applied that can recognize a first read sequence, then it or its attached signaling entity may be inactivated or removed, and a second secondary nucleic acid probe may be applied that can recognize a second read sequence. This process may be repeated multiple times, each with a different secondary nucleic acid probe, e.g., to determine the read sequences that were present in the various primary nucleic acid probes. Thus, primary nucleic acids within the sample can be determined on the basis of the binding pattern of secondary nucleic acid probes.

For example, a first location within the cell or other sample may exhibit binding of a first secondary probe and a third secondary probe, but not the binding of a second or a fourth secondary probe, while a second location may exhibit a different pattern of binding of various secondary probes. The primary nucleic acid probe that the secondary probes are able to bind to or hybridize with may be determined by considering the pattern of binding of various secondary probes. For instance, referring to FIG. 3A, if a first secondary probe is able to determine read sequence 27, a second secondary probe is able to determine read sequence 28, and a third secondary probe is able to determine read sequence 29, then primary nucleic acid 25 may be determined through the binding of the first and third secondary probes (but not the second secondary probe), while primary nucleic acid 26 may be determined through the binding of the first and second secondary probes (but not the third secondary probe). Similarly, if it is known that first probe 21 contains target sequence 25 while second probe 22 contains target sequence 26, then nucleic acids 11 and 12 may also be determined within the sample, e.g., spatially, based on the binding pattern of the various secondary nucleic acid probes. In addition, it should be noted that due to the presence of more than one read sequence on the primary nucleic acid probes, even though first probe 21 and second probe 22 contains a common read sequence (read sequence 27), these probes may be distinguished in the sample due to the different binding patterns of the various secondary nucleic acid probes.

In certain embodiments, this pattern of binding or hybridization of the secondary nucleic acid probes may be converted into a "codeword." In this example, for instance, the codewords are "101" and "110" for first probe 21 and second probe 22, respectively, where a value of 1 represents binding and a value of 0 represents no binding. The codewords may also have longer lengths in other embodiments; only three probes are shown here for clarity purposes only. A codeword can be directly related to a specific target nucleic acid sequence of the primary nucleic acid probe. Accordingly, different primary nucleic acid probes may match certain codewords, which can then be used to identify the different targets of the primary nucleic acid probes based on the binding patterns of the secondary probes, even if in some cases, there is overlap in the read sequences of different secondary probes, e.g., as was shown in FIG. 3A. However, if no binding is evident (e.g., for nucleic acid 13), then the codeword would be "000" in this example.

The values in each codeword can also be assigned in different fashions in some embodiments. For example, a value of 0 could represent binding while a value of 1 represents no binding. Similarly, a value of 1 could represent binding of a secondary nucleic acid probe with one type of signaling entity while a value of 0 could represent binding of a secondary nucleic acid probe with another type of distinguishable signaling entity. These signaling entities could be distinguished, for example, via different colors of fluorescence. In some cases, values in codewords need not be confined to 0 and 1. The values could also be drawn from larger alphabets, such as ternary (e.g., 0, 1, and 2) or quaternary (e.g., 0, 1, 2, and 3) systems. Each different value could, for example, be represented by a different distinguishable signaling entity, including (in some cases) one value that may be represented by the absence of signal.

The codewords for each target may be assigned sequentially, or may be assigned at random. For instance, referring to FIG. 3A, a first nucleic acid target may be assigned to 101, while a second nucleic acid target may be assigned to 110. In addition, in some embodiments, the codewords may be assigned using an error-detection system or an error-correcting system, such as a Hamming system, a Golay code, or an extended Hamming system (or a SECDED system, i.e., single error correction, double error detection). Generally speaking, such systems can be used to identify where errors have occurred, and in some cases, such systems can also be used to correct the errors and determine what the correct codeword should have been. For example, a codeword such as 001 may be detected as invalid and corrected using such a system to 101, e.g., if 001 is not previously assigned to a different target sequence. A variety of different error-correcting codes can be used, many of which have previously been developed for use within the computer industry; however, such error-correcting systems have not typically been used within biological systems. Additional examples of such error-correcting codes are discussed in more detail below.

It should also be understood that all possible codewords in a code need not be used in some cases. For example, in some embodiments, codewords that are not used can serve as negative controls. Similarly, in some embodiments, some codewords can be left out because they are more prone to errors in measurement than other codewords. For example, in some implementations, reading a codeword with more values of '1' might be more error-prone that reading a codeword with fewer values of '1.'

It should be understood that the above description is an example of one embodiment of the invention, and that primary and secondary nucleic acid probes are not necessary in all embodiments. For example, in some embodiments, a series of nucleic acid probes containing signaling entities are used to determine nucleic acids within a cell or other sample, without necessarily requiring secondary probes.

Figure 3B:
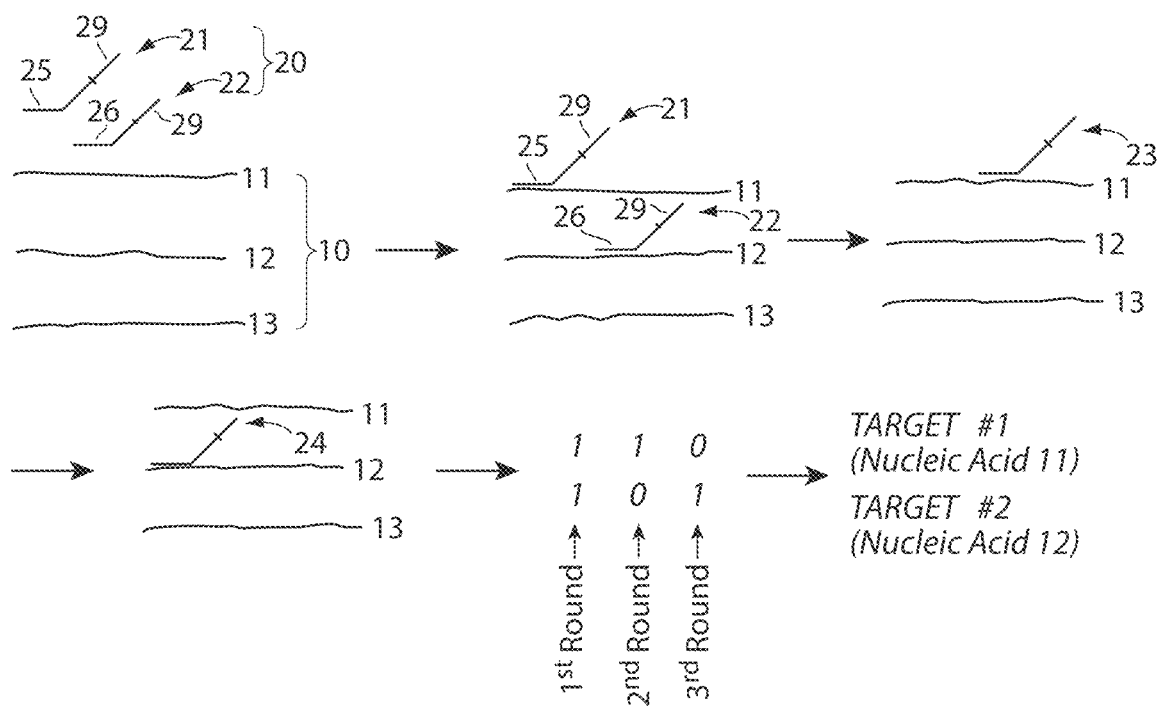

For example, turning now to FIG. 3B, nucleic acids 11, 12, and 13 are exposed to different rounds of probes 21, 22, 23, 24, etc. in this example. These probes may each contain a target sequence that can recognize a nucleic acid (e.g., a sequence within nucleic acid 11 or 12). These probes may each target the same nucleic acid, but different regions of the nucleic acid. In addition, some or all of the probes may contain one or more signaling entities, e.g., signaling entity 29 on probe 21. For example, the signaling entity may be a fluorescent entity attached to the probe, or a certain sequence of nucleic acids that can be determined in some fashion.

The first round of probes (e.g. probe 21 and probe 22) may be applied to the cell or other sample. Probe 21 may be allowed to bind to nucleic acid 11 via target sequence 25. Such binding can be determined by determining signaling entity 29. For example, if the signaling entity is fluorescent, then fluorescence microscopy can be used to determine the signaling entity, e.g., spatially within the cell or other sample. In some but not all embodiments, imaging of a sample to determine the signaling entity may be used at relatively high resolutions, and in some cases, super-resolution imaging techniques may be used. Other, different probes may be present as well; for instance, probe 22 containing target sequence 26 may bind to nucleic acid 12, and be determined via signaling entity 29 within probe 22. These may occur, e.g., sequentially or simultaneously. Optionally, probes 21 and 22 may also be removed or inactivated, e.g., between application of different rounds of probes.

Next, a second round of probes (e.g., probe 23) is applied to the sample. In this example, probe 23 is able to bind to nucleic acid 11 via a targeting region, although there is no probe in the second round that is able to bind to nucleic acid 12. Binding of the probes is allowed to occur as discussed above, and determination of binding may occur via signaling entities. These signaling entities may be the same or different as from the first round of probes. This process may be repeated any number of times with different probes. For example, as is shown in FIG. 3B, round 2 contains probes able to bind to nucleic acid 11, while round 3 contains probes able to bind to nucleic acid 12.

In certain embodiments, each round of binding or hybridization of nucleic acid probes may be converted into a "codeword." In this example, using probes 21, 22, 23, and 24, the codewords 101 or 110 could be formed, where 1 represents binding and 0 represents no binding and the first position corresponds to the binding of probes 21 or 22 while the second position corresponds to the binding of probes 22, and the third position corresponds to the binding of probe 24. A codeword of 000 would represent no binding, e.g., as shown with nucleic acid 13 in this example. A codeword can be directly related to a specific target nucleic acid sequence of the nucleic acid probes, by designing appropriate nucleic acid probes. Thus, for example, 110 may correspond to a first target nucleic acid 12 (e.g., the first and second round of nucleic acid probes containing probes able to target nucleic acid 11, and these probes may target the same or different regions of nucleic acid 11) while 101 may correspond to a second target nucleic acid (e.g., the first and third round of nucleic acid probes containing probes able to target nucleic acid 12, and these probes may target the same or different regions of nucleic acid 12). In addition, it should be noted that each round of probes may contain the same, or different signaling entities as other probes in the same round, and/or other probes in different rounds. For instance, in one set of embodiments, only one signaling entity is used in all of the rounds of probes.

Similar to the above, the codewords for each target may be assigned sequentially, or may be assigned at random. The codewords may be assigned within a code space in some embodiments using an error-detection or an error-correcting system, such as a Hamming system, a Golay code, or an extended Hamming system or a SECDED system (single error correction, double error detection). Generally speaking, such error-correction systems can be used to identify where errors have occurred, and in some cases, such systems can also be used to correct the errors and determine what the correct codeword should have been.

Similar to the above, the values at each position in the codeword can be arbitrarily assigned in certain embodiments to binding or non-binding of probes that contain more than one distinguishable signaling entity.

In some cases, the nucleic acid probes may be formed into "pools" or groups of nucleic acids that share a common feature. For example, probes to all targets with codewords that contain a 1 in the first position, e.g. 110 and 101 but not 011, may comprise one pool while probes to all targets that contain a 1 in the second position, e.g. 110 and 011 but not 101, may comprise another pool. See also FIG. 1C. In some cases, a nucleic acid probe may be a member of more than one group or pool. Members of a nucleic acid pool may also contain features in addition to target sequences, read sequences, and or signaling entities that allow them to be distinguished from other groups. These features may be short nucleic acid sequences that are used for the amplification, production, or separation of these sequences. The nucleic acid probes of each group may be applied to a sample, e.g., sequentially, as discussed herein.

Thus, in some aspects, the present invention is generally directed to systems and methods for determining nucleic acids within a cell or other sample. The sample may include a cell culture, a suspension of cells, a biological tissue, a biopsy, an organism, or the like. The sample may also be cell-free but nevertheless contain nucleic acids. If the sample contains a cell, the cell may be a human cell, or any other suitable cell, e.g., a mammalian cell, a fish cell, an insect cell, a plant cell, or the like. More than one cell may be present in some cases.

The nucleic acids to be determined may be, for example, DNA, RNA, or other nucleic acids that are present within a cell (or other sample). The nucleic acids may be endogenous to the cell, or added to the cell. For instance, the nucleic acid may be viral, or artificially created. In some cases, the nucleic acid to be determined may be expressed by the cell. The nucleic acid is RNA in some embodiments. The RNA may be coding and/or non-coding RNA. Non-limiting examples of RNA that may be studied within the cell include mRNA, siRNA, rRNA, miRNA, tRNA, lncRNA, snoRNAs, snRNAs, exRNAs, piRNAs, or the like.

In some cases, a significant portion of the nucleic acid within the cell may be studied. For instance, in some cases, enough of the RNA present within a cell may be determined so as to produce a partial or complete transcriptome of the cell. In some cases, at least 4 types of mRNAs are determined within a cell, and in some cases, at least 3, at least 4, at least 7, at least 8, at least 12, at least 14, at least 15, at least 16, at least 22, at least 30, at least 31, at least 32, at least 50, at least 63, at least 64, at least 72, at least 75, at least 100, at least 127, at least 128, at least 140, at least 255, at least 256, at least 500, at least 1,000, at least 1,500, at least 2,000, at least 2,500, at least 3,000, at least 4,000, at least 5,000, at least 7,500, at least 10,000, at least 12,000, at least 15,000, at least 20,000, at least 25,000, at least 30,000, at least 40,000, at least 50,000, at least 75,000, or at least 100,000 types of mRNAs may be determined within a cell.

In some cases, the transcriptome of a cell may be determined. It should be understood that the transcriptome generally encompasses all RNA molecules produced within a cell, not just mRNA. Thus, for instance, the transcriptome may also include rRNA, tRNA, siRNA, etc. In some embodiments, at least 5%, at least 10%, at least 15%, at least 20%, at least 25%, at least 30%, at least 40%, at least 50%, at least 60%, at least 70%, at least 80%, at least 90%, or 100% of the transcriptome of a cell may be determined.

The determination of one or more nucleic acids within the cell or other sample may be qualitative and/or quantitative. In addition, the determination may also be spatial, e.g., the position of the nucleic acid within the cell or other sample may be determined in two or three dimensions. In some embodiments, the positions, number, and/or concentrations of nucleic acids within the cell (or other sample) may be determined.

In some cases, a significant portion of the genome of a cell may be determined. The determined genomic segments may be continuous or interspersed on the genome. For example, in some cases, at least 4 genomic segments are determined within a cell, and in some cases, at least 3, at least 4, at least 7, at least 8, at least 12, at least 14, at least 15, at least 16, at least 22, at least 30, at least 31, at least 32, at least 50, at least 63, at least 64, at least 72, at least 75, at least 100, at least 127, at least 128, at least 140, at least 255, at least 256, at least 500, at least 1,000, at least 1,500, at least 2,000, at least 2,500, at least 3,000, at least 4,000, at least 5,000, at least 7,500, at least 10,000, at least 12,000, at least 15,000, at least 20,000, at least 25,000, at least 30,000, at least 40,000, at least 50,000, at least 75,000, or at least 100,000 genomic segments may be determined within a cell.

In some cases, the entire genome of a cell may be determined. It should be understood that the genome generally encompasses all DNA molecules produced within a cell, not just chromosome DNA. Thus, for instance, the genome may also include, in some cases, mitochondria DNA, chloroplast DNA, plasmid DNA, etc. In some embodiments, at least about 5%, at least about 10%, at least about 15%, at least about 20%, at least about 25%, at least about 30%, at least about 40%, at least about 50%, at least about 60%, at least about 70%, at least about 80%, at least about 90%, or 100% of the genome of a cell may be determined.

As discussed herein, a variety of nucleic acid probes may be used to determine one or more nucleic acids within a cell or other sample. The probes may comprise nucleic acids (or entities that can hybridize to a nucleic acid, e.g., specifically) such as DNA, RNA, LNA (locked nucleic acids), PNA (peptide nucleic acids), or combinations thereof. In some cases, additional components may also be present within the nucleic acid probes, e.g., as discussed below. Any suitable method may be used to introduce nucleic acid probes into a cell.

For example, in some embodiments, the cell is fixed prior to introducing the nucleic acid probes, e.g., to preserve the positions of the nucleic acids within the cell. Techniques for fixing cells are known to those of ordinary skill in the art. As non-limiting examples, a cell may be fixed using chemicals such as formaldehyde, paraformaldehyde, glutaraldehyde, ethanol, methanol, acetone, acetic acid, or the like. In one embodiment, a cell may be fixed using Hepes-glutamic acid buffer-mediated organic solvent (HOPE).

The nucleic acid probes may be introduced into the cell (or other sample) using any suitable method. In some cases, the cell may be sufficiently permeabilized such that the nucleic acid probes may be introduced into the cell by flowing a fluid containing the nucleic acid probes around the cells. In some cases, the cells may be sufficiently permeabilized as part of a fixation process; in other embodiments, cells may be permeabilized by exposure to certain chemicals such as ethanol, methanol, Triton, or the like. In addition, in some embodiments, techniques such as electroporation or microinjection may be used to introduce nucleic acid probes into a cell or other sample.

Certain aspects of the present invention are generally directed to nucleic acid probes that are introduced into a cell (or other sample). The probes may comprise any of a variety of entities that can hybridize to a nucleic acid, typically by Watson-Crick base pairing, such as DNA, RNA, LNA, PNA, etc., depending on the application. The nucleic acid probe typically contains a target sequence that is able to bind to at least a portion of a target nucleic acid, in some cases specifically. When introduced into a cell or other system, the target system may be able to bind to a specific target nucleic acid (e.g., an mRNA, or other nucleic acids as discussed herein). In some cases, the nucleic acid probes may be determined using signaling entities (e.g., as discussed below), and/or by using secondary nucleic acid probes able to bind to the nucleic acid probes (i.e., to primary nucleic acid probes). The determination of such nucleic acid probes is discussed in detail below.

In some cases, more than one type of (primary) nucleic acid probe may be applied to a sample, e.g., simultaneously. For example, there may be at least 2, at least 5, at least 10, at least 25, at least 50, at least 75, at least 100, at least 300, at least 1,000, at least 3,000, at least 10,000, or at least 30,000 distinguishable nucleic acid probes that are applied to a sample, e.g., simultaneously or sequentially.

The target sequence may be positioned anywhere within the nucleic acid probe (or primary nucleic acid probe or encoding nucleic acid probe). The target sequence may contain a region that is substantially complementary to a portion of a target nucleic acid. In some cases, the portions may be at least 50%, at least 60%, at least 70%, at least 75%, at least 80%, at least 85%, at least 90%, at least 92%, at least 94%, at least 95%, at least 96%, at least 97%, at least 98%, at least 99%, or 100% complementary. In some cases, the target sequence may be at least 5, at least 10, at least 15, at least 20, at least 25, at least 30, at least 35, at least 40, at least 50, at least 60, at least 65, at least 75, at least 100, at least 125, at least 150, at least 175, at least 200, at least 250, at least 300, at least 350, at least 400, or at least 450 nucleotides in length. In some cases, the target sequence may be no more than 500, no more than 450, no more than 400, no more than 350, no more than 300, no more than 250, no more than 200, no more than 175, no more than 150, no more than 125, no more than 100, be no more than 75, no more than 60, no more than 65, no more than 60, no more than 55, no more than 50, no more than 45, no more than 40, no more than 35, no more than 30, no more than 20, or no more than 10 nucleotides in length. Combinations of any of these are also possible, e.g., the target sequence may have a length of between 10 and 30 nucleotides, between 20 and 40 nucleotides, between 5 and 50 nucleotides, between 10 and 200 nucleotides, or between 25 and 35 nucleotides, between 10 and 300 nucleotides, etc. Typically, complementarity is determined on the basis of Watson-Crick nucleotide base pairing.

The target sequence of a (primary) nucleic acid probe may be determined with reference to a target nucleic acid suspected of being present within a cell or other sample. For example, a target nucleic acid to a protein may be determined using the protein's sequence, by determining the nucleic acids that are expressed to form the protein. In some cases, only a portion of the nucleic acids encoding the protein are used, e.g., having the lengths as discussed above. In addition, in some cases, more than one target sequence that can be used to identify a particular target may be used. For instance, multiple probes can be used, sequentially and/or simultaneously, that can bind to or hybridize to different regions of the same target. Hybridization typically refers to an annealing process by which complementary single-stranded nucleic acids associate through Watson-Crick nucleotide base pairing (e.g., hydrogen bonding, guanine-cytosine and adenine-thymine) to form double-stranded nucleic acid.

In some embodiments, a nucleic acid probe, such as a primary nucleic acid probe, may also comprise one or more "read" sequences. However, it should be understood that read sequences are not necessary in all cases. In some embodiments, the nucleic acid probe may comprise 1, 2, 3, 4, 5, 6, 7, 8, 9, 10, 11, 12, 13, 14, 15, 16 or more, 20 or more, 32 or more, 40 or more, 50 or more, 64 or more, 75 or more, 100 or more, 128 or more read sequences. The read sequences may be positioned anywhere within the nucleic acid probe. If more than one read sequence is present, the read sequences may be positioned next to each other, and/or interspersed with other sequences.

The read sequences, if present, may be of any length. If more than one read sequence is used, the read sequences may independently have the same or different lengths. For instance, the read sequence may be at least 5, at least 10, at least 15, at least 20, at least 25, at least 30, at least 35, at least 40, at least 50, at least 60, at least 65, at least 75, at least 100, at least 125, at least 150, at least 175, at least 200, at least 250, at least 300, at least 350, at least 400, or at least 450 nucleotides in length. In some cases, the read sequence may be no more than 500, no more than 450, no more than 400, no more than 350, no more than 300, no more than 250, no more than 200, no more than 175, no more than 150, no more than 125, no more than 100, be no more than 75, no more than 60, no more than 65, no more than 60, no more than 55, no more than 50, no more than 45, no more than 40, no more than 35, no more than 30, no more than 20, or no more than 10 nucleotides in length. Combinations of any of these are also possible, e.g., the read sequence may have a length of between 10 and 30 nucleotides, between 20 and 40 nucleotides, between 5 and 50 nucleotides, between 10 and 200 nucleotides, or between 25 and 35 nucleotides, between 10 and 300 nucleotides, etc.

The read sequence may be arbitrary or random in some embodiments. In certain cases, the read sequences are chosen so as to reduce or minimize homology with other components of the cell or other sample, e.g., such that the read sequences do not themselves bind to or hybridize with other nucleic acids suspected of being within the cell or other sample. In some cases, the homology may be less than 10%, less than 8%, less than 7%, less than 6%, less than 5%, less than 4%, less than 3%, less than 2%, or less than 1%. In some cases, there may be a homology of less than 20 basepairs, less than 18 basepairs, less than 15 basepairs, less than 14 basepairs, less than 13 basepairs, less than 12 basepairs, less than 11 basepairs, or less than 10 basepairs. In some cases, the basepairs are sequential.

In one set of embodiments, a population of nucleic acid probes may contain a certain number of read sequences, which may be less than the number of targets of the nucleic acid probes in some cases. Those of ordinary skill in the art will be aware that if there is one signaling entity and n read sequences, then in general $2^n-1$ different nucleic acid targets may be uniquely identified. However, not all possible combinations need be used. For instance, a population of nucleic acid probes may target 12 different nucleic acid sequences, yet contain no more than 8 read sequences. As another example, a population of nucleic acids may target 140 different nucleic acid species, yet contain no more than 16 read sequences. Different nucleic acid sequence targets may be separately identified by using different combinations of read sequences within each probe. For instance, each probe may contain 1, 2, 3, 4, 5, 6, 7, 8, 9, 10, 11, 12, 13, 14, 15, etc. or more read sequences. In some cases, a population of nucleic acid probes may each contain the same number of read sequences, although in other cases, there may be different numbers of read sequences present on the various probes.

As a non-limiting example, a first nucleic acid probe may contain a first target sequence, a first read sequence, and a second read sequence, while a second, different nucleic acid probe may contain a second target sequence, the same first read sequence, but a third read sequence instead of the second read sequence. Such probes may thereby be distinguished by determining the various read sequences present or associated with a given probe or location, as discussed herein.

In addition, the nucleic acid probes (and their corresponding, complimentary sites on the encoding probes), in certain embodiments, may be made using only 2 or only 3 of the 4 bases, such as leaving out all the "G"s or leaving out all of the "C"s within the probe. Sequences lacking either "G"s or "C"s may form very little secondary structure in certain embodiments, and can contribute to more uniform, faster hybridization.

In some embodiments, the nucleic acid probe may contain a signaling entity. It should be understood that signaling entities are not required in all cases, however; for instance, the nucleic acid probe may be determined using secondary nucleic acid probes in some embodiments, as is discussed in additional detail below. Examples of signaling entities that can be used are also discussed in more detail below.

Other components may also be present within a nucleic acid probe as well. For example, in one set of embodiments, one or more primer sequences may be present, e.g., to allow for enzymatic amplification of probes. Those of ordinary skill in the art will be aware of primer sequences suitable for applications such as amplification (e.g., using PCR or other suitable techniques). Many such primer sequences are available commercially. Other examples of sequences that may be present within a primary nucleic acid probe include, but are not limited to promoter sequences, operons, identification sequences, nonsense sequences, or the like.

Typically, a primer is a single-stranded or partially double-stranded nucleic acid (e.g., DNA) that serves as a starting point for nucleic acid synthesis, allowing polymerase enzymes such as nucleic acid polymerase to extend the primer and replicate the complementary strand. A primer is (e.g., is designed to be) complementary to and to hybridize to a target nucleic acid. In some embodiments, a primer is a synthetic primer. In some embodiments, a primer is a non-naturally-occurring primer. A primer typically has a length of 10 to 50 nucleotides. For example, a primer may have a length of 10 to 40, 10 to 30, 10 to 20, 25 to 50, 15 to 40, 15 to 30, 20 to 50, 20 to 40, or 20 to 30 nucleotides. In some embodiments, a primer has a length of 18 to 24 nucleotides.

In addition, the components of the nucleic acid probe may be arranged in any suitable order. For instance, in one embodiment, the components may be arranged in a nucleic acid probe as: primer—read sequences—targeting sequence—read sequences-reverse primer.

The "read sequences" in this structure may each contain any number (including 0) of read sequences, so long as at least one read sequence is present in the probe. Non-limiting example structures include primer—targeting sequence—read sequences—reverse primer, primer—read sequences—targeting sequence-reverse primer, targeting sequence—primer—targeting sequence—read sequences—reverse primer, targeting sequence—primer—read sequences—targeting sequence—reverse primer, primer—target sequence—read sequences—targeting sequence-reverse primer, targeting sequence—primer—read sequence—reverse primer, targeting sequence—read sequence—primer, read sequence—targeting sequence—primer, read sequence—primer—targeting sequence—reverse primer, etc. In addition, the reverse primer is optional in some embodiments, including in all of the above-described examples.

After introduction of the nucleic acid probes into a cell or other sample, the nucleic acid probes may be directly determined by determining signaling entities (if present), and/or the nucleic acid probes may be determined by using one or more secondary nucleic acid probes, in accordance with certain aspects of the invention. As mentioned, in some cases, the determination may be spatial, e.g., in two or three dimensions. In addition, in some cases, the determination may be quantitative, e.g., the amount or concentration of a primary nucleic acid probe (and of a target nucleic acid) may be determined. Additionally, the secondary probes may comprise any of a variety of entities able to hybridize a nucleic acid, e.g., DNA, RNA, LNA, and/or PNA, etc., depending on the application. Signaling entities are discussed in more detail below.

A secondary nucleic acid probe may contain a recognition sequence able to bind to or hybridize with a read sequence of a primary nucleic acid probe. In some cases, the binding is specific, or the binding may be such that a recognition sequence preferentially binds to or hybridizes with only one of the read sequences that are present. The secondary nucleic acid probe may also contain one or more signaling entities. If more than one secondary nucleic acid probe is used, the signaling entities may be the same or different.

The recognition sequences may be of any length, and multiple recognition sequences may be of the same or different lengths. If more than one recognition sequence is used, the recognition sequences may independently have the same or different lengths. For instance, the recognition sequence may be at least 5, at least 10, at least 15, at least 20, at least 25, at least 30, at least 35, at least 40, or at least 50 nucleotides in length. In some cases, the recognition sequence may be no more than 75, no more than 60, no more than 65, no more than 60, no more than 55, no more than 50, no more than 45, no more than 40, no more than 35, no more than 30, no more than 20, or no more than 10 nucleotides in length. Combinations of any of these are also possible, e.g., the recognition sequence may have a length of between 10 and 30, between 20 and 40, or between 25 and 35 nucleotides, etc. In one embodiment, the recognition sequence is of the same length as the read sequence. In addition, in some cases, the recognition sequence may be at least 50%, at least 60%, at least 70%, at least 75%, at least 80%, at least 85%, at least 90%, at least 92%, at least 94%, at least 95%, at least 96%, at least 97%, at least 98%, at least 99%, or at least 100% complementary to a read sequence of the primary nucleic acid probe.

As mentioned, in some cases, the secondary nucleic acid probe may comprise one or more signaling entities. Examples of signaling entities are discussed in more detail below.

As discussed, in certain aspects of the invention, nucleic acid probes are used that contain various "read sequences."

For example, a population of primary nucleic acid probes may contain certain "read sequences" which can bind certain of the secondary nucleic acid probes, and the locations of the primary nucleic acid probes are determined within the sample using secondary nucleic acid probes, e.g., which comprise a signaling entity. As mentioned, in some cases, a population of read sequences may be combined in various combinations to produce different nucleic acid probes, e.g., such that a relatively small number of read sequences may be used to produce a relatively large number of different nucleic acid probes.

Thus, in some cases, a population of primary nucleic acid probes (or other nucleic acid probes) may each contain a certain number of read sequences, some of which are shared between different primary nucleic acid probes such that the total population of primary nucleic acid probes may contain a certain number of read sequences. A population of nucleic acid probes may have any suitable number of read sequences. For example, a population of primary nucleic acid probes may have 1, 2, 3, 4, 5, 6, 7, 8, 9, 10, 11, 12, 13, 14, 15, 16, 17, 18, 19, 20 etc. read sequences. More than 20 are also possible in some embodiments. In addition, in some cases, a population of nucleic acid probes may, in total, have 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 20 or more, 24 or more, 32 or more, 40 or more, 50 or more, 60 or more, 64 or more, 100 or more, 128 or more, etc. of possible read sequences present, although some or all of the probes may each contain more than one read sequence, as discussed herein. In addition, in some embodiments, the population of nucleic acid probes may have no more than 100, no more than 80, no more than 64, no more than 60, no more than 50, no more than 40, no more than 32, no more than 24, no more than 20, no more than 16, no more than 15, no more than 14, no more than 13, no more than 12, no more than 11, no more than 10, no more than 9, no more than 8, no more than 7, no more than 6, no more than 5, no more than 4, no more than 3, or no more than two read sequences present. Combinations of any of these are also possible, e.g., a population of nucleic acid probes may comprise between 10 and 15 read sequences in total.

Figure 4A:
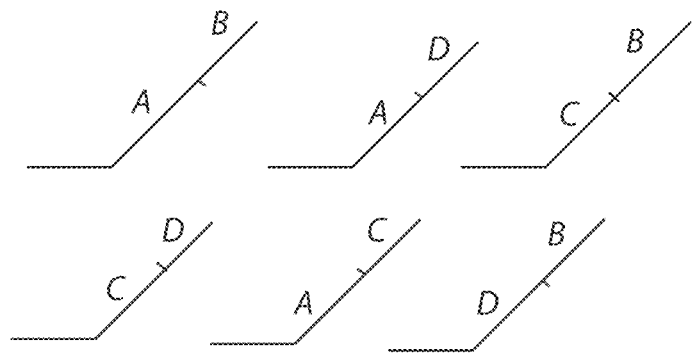
FIGS. 4A-4B is a non-limiting example of multiple read sequences distributed in a population of different nucleic acid probes, in accordance with certain embodiments of the invention.
Figure 4B:
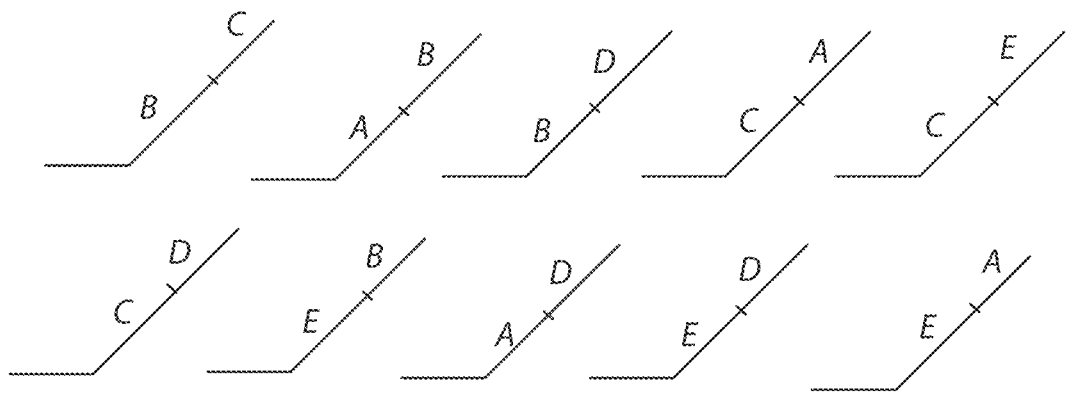

As a non-limiting example of an approach to combinatorially producing a relatively large number of nucleic acid probes from a relatively small number of read sequences, in a population of 6 different types of nucleic acid probes, each comprising one or more read sequences, the total number of read sequences within the population may be no greater than 4. It should be understood that although 4 read sequences are used in this example for ease of explanation, in other embodiments, larger numbers of nucleic acid probes may be realized, for example, using 5, 8, 10, 16, 32, etc. or more read sequences, or any other suitable number of read sequences described herein, depending on the application. Referring now to FIG. 4A, if each of the primary nucleic acid probes contains two different read sequences, then by using 4 such read sequences (A, B, C, and D), up to 6 probes may be separately identified. It should be noted that in this example, the ordering of read sequences on a nucleic acid probe is not essential, i.e., "AB" and "BA" may be treated as being synonymous (although in other embodiments, the ordering of read sequences may be essential and "AB" and "BA" may not necessarily be synonymous). Similarly, if 5 read sequences are used (A, B, C, D, and E) in the population of primary nucleic acid probes, up to 10 probes may be separately identified, as is shown in FIG. 4B. For example, one of ordinary skill in the art would understand that, for k read sequences in a population with n read sequences on each probe, up to $\binom{n}{k}$ different probes may be produced, assuming that the ordering of read sequences is not essential; because not all of the probes need to have the same number of read sequences and not all combinations of read sequences need to be used in every embodiment, either more or less than this number of different probes may also be used in certain embodiments. In addition, it should also be understood that the number of read sequences on each probe need not be identical in some embodiments. For instance example, some probes may contain 2 read sequences while other probes may contain 3 read sequences.

In some aspects, the read sequences and/or the pattern of binding of nucleic acid probes within a sample may be used to define an error-detecting and/or an error-correcting code, for example, to reduce or prevent misidentification or errors of the nucleic acids, e.g., as was discussed with reference to FIG. 3. Thus, for example, if binding is indicated (e.g., as determined using a signaling entity), then the location may be identified with a "1"; conversely, if no binding is indicated, then the location may be identified with a "0" (or vice versa, in some cases). Multiple rounds of binding determinations, e.g., using different nucleic acid probes, can then be used to create a "codeword," e.g., for that spatial location. In some embodiments, the codeword may be subjected to error detection and/or correction. For instance, the codewords may be organized such that, if no match is found for a given set of read sequences or binding pattern of nucleic acid probes, then the match may be identified as an error, and optionally, error correction may be applied sequences to determine the correct target for the nucleic acid probes. In some cases, the codewords may have fewer "letters" or positions that the total number of nucleic acids encoded by the codewords, e.g. where each codeword encodes a different nucleic acid.

Such error-detecting and/or the error-correction code may take a variety of forms. A variety of such codes have previously been developed in other contexts such as the telecommunications industry, such as Golay codes or Hamming codes. In one set of embodiments, the read sequences or binding patterns of the nucleic acid probes are assigned such that not every possible combination is assigned.

For example, if 4 read sequences are possible and a primary nucleic acid probe contains 2 read sequences, then up to 6 primary nucleic acid probes could be identified; but the number of primary nucleic acid probes used may be less than 6. Similarly, for k read sequences in a population with n read sequences on each primary nucleic acid probe, $\binom{n}{k}$ different probes may be produced, but the number of primary nucleic acid probes that are used may be any number more or less than $\binom{n}{k}$. In addition, these may be randomly assigned, or assigned in specific ways to increase the ability to detect and/or correct errors.

As another example, if multiple rounds of nucleic acid probes are used, the number of rounds may be arbitrarily chosen. If in each round, each target can give two possible outcomes, such as being detected or not being detected, up to $2^n$ different targets may be possible for n rounds of probes, but the number of nucleic acid targets that are actually used may be any number less than $2^n$. For example, if in each round, each target can give more than two possible outcomes, such as being detected in different color channels, more than $2^n$ (e.g. $3^n$, $4^n$ . . . ) different targets may be possible for n rounds of probes. In some cases, the number of nucleic acid targets that are actually used may be any number less than this number. In addition, these may be randomly assigned, or assigned in specific ways to increase the ability to detect and/or correct errors.

For example, in one set of embodiments, the codewords or nucleic acid probes may be assigned within a code space such that the assignments are separated by a Hamming distance, which measures the number of incorrect "reads" in a given pattern that cause the nucleic acid probe to be misinterpreted as a different valid nucleic acid probe. In certain cases, the Hamming distance may be at least 2, at least 3, at least 4, at least 5, at least 6, or the like. In addition, in one set of embodiments, the assignments may be formed as a Hamming code, for instance, a Hamming(7, 4) code, a Hamming(15, 11) code, a Hamming(31, 26) code, a Hamming(63, 57) code, a Hamming(127, 120) code, etc. In another set of embodiments, the assignments may form a SECDED code, e.g., a SECDED(8,4) code, a SECDED(16, 4) code, a SECDED(16, 11) code, a SECDED(22, 16) code, a SECDED(39, 32) code, a SECDED(72, 64) code, etc. In yet another set of embodiments, the assignments may form an extended binary Golay code, a perfect binary Golay code, or a ternary Golay code. In another set of embodiments, the assignments may represent a subset of the possible values taken from any of the codes described above.

For example, a code with the same error correcting properties of the SECDED code may be formed by using only binary words that contain a fixed number of '1' bits, such as 4, to encode the targets. In another set of embodiments, the assignments may represent a subset of the possible values taken from codes described above for the purpose of addressing asymmetric readout errors. For example, in some cases, a code in which the number of '1' bits may be fixed for all used binary words may eliminate the biased measurement of words with different numbers of '1's when the rate at which '0' bits are measured as '1's or '1' bits are measured as '0's are different.

Accordingly, in some embodiments, once the codeword is determined (e.g., as discussed herein), the codeword may be compared to the known nucleic acid codewords. If a match is found, then the nucleic acid target can be identified or determined. If no match is found, then an error in the reading of the codeword may be identified. In some cases, error correction can also be applied to determine the correct codeword, and thus resulting in the correct identity of the nucleic acid target. In some cases, the codewords may be selected such that, assuming that there is only one error present, only one possible correct codeword is available, and thus, only one correct identity of the nucleic acid target is possible. In some cases, this may also be generalized to larger codeword spacings or Hamming distances; for instance, the codewords may be selected such that if two, three, or four errors are present (or more in some cases), only one possible correct codeword is available, and thus, only one correct identity of the nucleic acid targets is possible.

The error-correcting code may be a binary error-correcting code, or it may be based on other numbering systems, e.g., ternary or quaternary error-correcting codes. For instance, in one set of embodiments, more than one type of signaling entity may be used and assigned to different numbers within the error-correcting code. Thus, as a non-limiting example, a first signaling entity (or more than one signaling entity, in some cases) may be assigned as "1" and a second signaling entity (or more than one signaling entity, in some cases) may be assigned as "2" (with "0" indicating no signaling entity present), and the codewords distributed to define a ternary error-correcting code. Similarly, a third signaling entity may additionally be assigned as "3" to make a quaternary error-correcting code, etc.

As discussed above, in certain aspects, signaling entities are determined, e.g., to determine nucleic acid probes and/or to create codewords. In some cases, signaling entities within a sample may be determined, e.g., spatially, using a variety of techniques. In some embodiments, the signaling entities may be fluorescent, and techniques for determining fluorescence within a sample, such as fluorescence microscopy or confocal microscopy, may be used to spatially identify the positions of signaling entities within a cell. In some cases, the positions of entities within the sample may be determined in two or even three dimensions. In addition, in some embodiments, more than one signaling entity may be determined at a time (e.g., signaling entities with different colors or emissions), and/or sequentially.

In addition, in some embodiments, a confidence level for the identified nucleic acid target may be determined. For example, the confidence level may be determined using a ratio of the number of exact matches to the number of matches having one or more one-bit errors. In some cases, only matches having a confidence ratio greater than a certain value may be used. For instance, in certain embodiments, matches may be accepted only if the confidence ratio for the match is greater than about 0.01, greater than about 0.03, greater than about 0.05, greater than about 0.1, greater than about 0.3, greater than about 0.5, greater than about 1, greater than about 3, greater than about 5, greater than about 10, greater than about 30, greater than about 50, greater than about 100, greater than about 300, greater than about 500, greater than about 1000, or any other suitable value. In addition, in some embodiments, matches may be accepted only if the confidence ratio for the identified nucleic acid target is greater than an internal standard or false positive control by about 0.01, about 0.03, about 0.05, about 0.1, about 0.3, about 0.5, about 1, about 3, about 5, about 10, about 30, about 50, about 100, about 300, about 500, about 1000, or any other suitable value In some embodiments, the spatial positions of the entities (and thus, nucleic acid probes that the entities may be associated with) may be determined at relatively high resolutions. For instance, the positions may be determined at spatial resolutions of better than about 100 micrometers, better than about 30 micrometers, better than about 10 micrometers, better than about 3 micrometers, better than about 1 micrometer, better than about 800 nm, better than about 600 nm, better than about 500 nm, better than about 400 nm, better than about 300 nm, better than about 200 nm, better than about 100 nm, better than about 90 nm, better than about 80 nm, better than about 70 nm, better than about 60 nm, better than about 50 nm, better than about 40 nm, better than about 30 nm, better than about 20 nm, or better than about 10 nm, etc.

There are a variety of techniques able to determine or image the spatial positions of entities optically, e.g., using fluorescence microscopy. In some cases, the spatial positions may be determined at super resolutions, or at resolutions better than the wavelength of light or the diffraction limit. Non-limiting examples include STORM (stochastic optical reconstruction microscopy), STED (stimulated emission depletion microscopy), NSOM (Near-field Scanning Optical Microscopy), 4Pi microscopy, SIM (Structured Illumination Microscopy), SMI (Spatially Modulated Illumination) microscopy, RESOLFT (Reversible Saturable Optically Linear Fluorescence Transition Microscopy), GSD (Ground State Depletion Microscopy), SSIM (Saturated Structured-Illumination Microscopy), SPDM (Spectral Precision Distance Microscopy), Photo-Activated Localization Microscopy (PALM), Fluorescence Photoactivation Localization Microscopy (FPALM), LIMON (3D Light Microscopical Nanosizing Microscopy), Super-resolution optical fluctuation imaging (SOFI), or the like. See, e.g., U.S. Pat. No. 7,838,302, issued Nov. 23, 2010, entitled "Sub-Diffraction Limit Image Resolution and Other Imaging Techniques," by Zhuang, et al.; U.S. Pat. No. 8,564,792, issued Oct. 22, 2013, entitled "Sub-diffraction Limit Image Resolution in Three Dimensions," by Zhuang, et al.; or Int. Pat. Apl. Pub. No. WO 2013/090360, published Jun. 20, 2013, entitled "High Resolution Dual-Objective Microscopy," by Zhuang, et al., each incorporated herein by reference in their entireties.

As an illustrative non-limiting example, in one set of embodiments, the sample may be imaged with a high numerical aperture, oil immersion objective with 100× magnification and light collected on an electron-multiplying CCD camera. In another example, the sample could be imaged with a high numerical aperture, oil immersion lens with 40× magnification and light collected with a wide-field scientific CMOS camera. With different combinations of objectives and cameras, a single field of view may correspond to no less than 40×40 microns, 80×80 microns, 120×120 microns, 240×240 microns, 340×340 microns, or 500×500 microns, etc. in various non-limiting embodiments. Similarly, a single camera pixel may correspond, in some embodiments, to regions of the sample of no less than 80×80 nm, 120×120 nm, 160×160 nm, 240×240 nm, or 300×300 nm, etc. In another example, the sample may be imaged with a low numerical aperture, air lens with 10× magnification and light collected with a sCMOS camera. In additional embodiments, the sample may be optically sectioned by illuminating it via a single or multiple scanned diffraction limited foci generated either by scanning mirrors or a spinning disk and the collected passed through a single or multiple pinholes. In another embodiment, the sample may also be illuminated via thin sheet of light generated via any one of multiple methods known to those versed in the art.

In one embodiment, the sample may be illuminated by single Gaussian mode laser lines. In some embodiments, the illumination profiled may be flattened by passing these laser lines through a multimode fiber that is vibrated via piezoelectric or other mechanical means. In some embodiments, the illumination profile may be flattened by passing single-mode, Gaussian beams through a variety of refractive beam shapers, such as the piShaper or a series of stacked Powell lenses. In yet another set of embodiments, the Gaussian beams may be passed through a variety of different diffusing elements, such as ground glass or engineered diffusers, which may be spun in some cases at high speeds to remove residual laser speckle. In yet another embodiment, laser illumination may be passed through a series of lenslet arrays to produce overlapping images of the illumination that approximate a flat illumination field.

In some embodiments, the centroids of the spatial positions of the entities may be determined. For example, a centroid of a signaling entity may be determined within an image or series of images using image analysis algorithms known to those of ordinary skill in the art. In some cases, the algorithms may be selected to determine non-overlapping single emitters and/or partially overlapping single emitters in a sample. Non-limiting examples of suitable techniques include a maximum likelihood algorithm, a least squares algorithm, a Bayesian algorithm, a compressed sensing algorithm, or the like. Combinations of these techniques may also be used in some cases.

In addition, the signaling entity may be inactivated in some cases. For example, in some embodiments, a first secondary nucleic acid probe containing a signaling entity may be applied to a sample that can recognize a first read sequence, then the first secondary nucleic acid probe can be inactivated before a second secondary nucleic acid probe is applied to the sample. If multiple signaling entities are used, the same or different techniques may be used to inactivate the signaling entities, and some or all of the multiple signaling entities may be inactivated, e.g., sequentially or simultaneously.

Inactivation may be caused by removal of the signaling entity (e.g., from the sample, or from the nucleic acid probe, etc.), and/or by chemically altering the signaling entity in some fashion, e.g., by photobleaching the signaling entity, bleaching or chemically altering the structure of the signaling entity, e.g., by reduction, etc.). For instance, in one set of embodiments, a fluorescent signaling entity may be inactivated by chemical or optical techniques such as oxidation, photobleaching, chemically bleaching, stringent washing or enzymatic digestion or reaction by exposure to an enzyme, dissociating the signaling entity from other components (e.g., a probe), chemical reaction of the signaling entity (e.g., to a reactant able to alter the structure of the signaling entity) or the like. For instance, bleaching may occur by exposure to oxygen, reducing agents, or the signaling entity could be chemically cleaved from the nucleic acid probe and washed away via fluid flow.

In some embodiments, various nucleic acid probes (including primary and/or secondary nucleic acid probes) may include one or more signaling entities. If more than one nucleic acid probe is used, the signaling entities may each by the same or different. In certain embodiments, a signaling entity is any entity able to emit light. For instance, in one embodiment, the signaling entity is fluorescent. In other embodiments, the signaling entity may be phosphorescent, radioactive, absorptive, etc. In some cases, the signaling entity is any entity that can be determined within a sample at relatively high resolutions, e.g., at resolutions better than the wavelength of visible light or the diffraction limit. The signaling entity may be, for example, a dye, a small molecule, a peptide or protein, or the like. The signaling entity may be a single molecule in some cases. If multiple secondary nucleic acid probes are used, the nucleic acid probes may comprise the same or different signaling entities.

Non-limiting examples of signaling entities include fluorescent entities (fluorophores) or phosphorescent entities, for example, cyanine dyes (e.g., Cy2, Cy3, Cy3B, Cy5, Cy5.5, Cy7, etc.), Alexa Fluor dyes, Atto dyes, photoswitchable dyes, photoactivatable dyes, fluorescent dyes, metal nanoparticles, semiconductor nanoparticles or "quantum dots", fluorescent proteins such as GFP (Green Fluorescent Protein), or photoactivatable fluorescent proteins, such as PAGFP, PSCFP, PSCFP2, Dendra, Dendra2, EosFP, tdEos, mEos2, mEos3, PAmCherry, PAtagRFP, mMaple, mMaple2, and mMaple3. Other suitable signaling entities are known to those of ordinary skill in the art. See, e.g., U.S. Pat. No. 7,838,302 or U.S. Pat. Apl. Ser. No. 61/979,436, each incorporated herein by reference in its entirety.

In one set of embodiments, the signaling entity may be attached to an oligonucleotide sequence via a bond that can be cleaved to release the signaling entity. In one set of embodiments, a fluorophore may be conjugated to an oligonucleotide via a cleavable bond, such as a photocleavable bond. Non-limiting examples of photocleavable bonds include, but are not limited to, 1-(2-nitrophenyl)ethyl, 2-nitrobenzyl, biotin phosphoramidite, acrylic phosphoramidite, diethylaminocoumarin, 1-(4,5-dimethoxy-2-nitrophenyl) ethyl, cyclo-dodecyl (dimethoxy-2-nitrophenyl)ethyl, 4-aminomethyl-3-nitrobenzyl, (4-nitro-3-(1-chlorocarbonyloxyethyl)phenyl)methyl-S-acetylthioic acid ester, (4-nitro-3-(1-thlorocarbonyloxyethyl)phenyl)methyl-3-(2-pyridyldithiopropionic acid) ester, 3-(4,4'-dimethoxytrityl)-1-(2-nitrophenyl)-propane-1,3-diol-[2-cyanoethyl-(N,N-diisopropyl)]-phosphoramidite, 1-[2-nitro-5-(6-trifluoroacetyl-caproamidomethyl)phenyl]-ethyl-[2-cyano-ethyl-(N,N-diisopropyl)]-phosphoramidite, 1-[2-nitro-5-(6-(4,4'-dimethoxytrityloxy)butyramidomethyl)phenyl]-ethyl-[2-cyano-ethyl-(N,N-diisopropyl)]-phosphoramidite, 1-[2-nitro-5-(6-(N-(4,4'-dimethoxytrityl))-biotinamidocaproamido-methyl) phenyl]-ethyl-[2-cyanoethyl-(N,N-diisopropyl)]-phosphoramidite, or similar linkers. In another set of embodiments, the fluorophore may be conjugated to an oligonucleotide via a disulfide bond. The disulfide bond may be cleaved by a variety of reducing agents such as, but not limited to, dithiothreitol, dithioerythritol, beta-mercaptoethanol, sodium borohydride, thioredoxin, glutaredoxin, trypsinogen, hydrazine, diisobutylaluminum hydride, oxalic acid, formic acid, ascorbic acid, phosphorous acid, tin chloride, glutathione, thioglycolate, 2,3-dimercaptopropanol, 2-mercaptoethylamine, 2-aminoethanol, tris(2-carboxyethyl)phosphine, bis(2-mercaptoethyl) sulfone, N,N'-dimethyl-N,N'-bis(mercaptoacetyl)hydrazine, 3-mercaptoproptionate, dimethylformamide, thiopropyl-agarose, tri-n-butylphosphine, cysteine, iron sulfate, sodium sulfite, phosphite, hypophosphite, phosphorothioate, or the like, and/or combinations of any of these. In another embodiment, the fluorophore may be conjugated to an oligonucleotide via one or more phosphorothioate modified nucleotides in which the sulfur modification replaces the bridging and/or non-bridging oxygen. The fluorophore may be cleaved from the oligonucleotide, in certain embodiments, via addition of compounds such as but not limited to iodoethanol, iodine mixed in ethanol, silver nitrate, or mercury chloride. In yet another set of embodiments, the signaling entity may be chemically inactivated through reduction or oxidation. For example, in one embodiment, a chromophore such as Cy5 or Cy7 may be reduced using sodium borohydride to a stable, non-fluorescence state. In still another set of embodiments, a fluorophore may be conjugated to an oligonucleotide via an azo bond, and the azo bond may be cleaved with 2-[(2-N-arylamino)phenylazo]pyridine. In yet another set of embodiments, a fluorophore may be conjugated to an oligonucleotide via a suitable nucleic acid segment that can be cleaved upon suitable exposure to DNAse, e.g., an exodeoxyribonuclease or an endodeoxyribonuclease. Examples include, but are not limited to, deoxyribonuclease I or deoxyribonuclease II. In one set of embodiments, the cleavage may occur via a restriction endonuclease. Non-limiting examples of potentially suitable restriction endonucleases include BamHI, BsrI, NotI, XmaI, PspAI, DpnI, MboI, MnlI, Eco57I, Ksp632I, DraIII, AhaII, SmaI, MluI, HpaI, ApaI, BelI, BstEII, TaqI, EcoRI, SacI, HindII, HaeII, DraII, Tsp509I, Sau3AI, PacI, etc. Over 3000 restriction enzymes have been studied in detail, and more than 600 of these are available commercially. In yet another set of embodiments, a fluorophore may be conjugated to biotin, and the oligonucleotide conjugated to avidin or streptavidin. An interaction between biotin and avidin or streptavidin allows the fluorophore to be conjugated to the oligonucleotide, while sufficient exposure to an excess of addition, free biotin could "outcompete" the linkage and thereby cause cleavage to occur. In addition, in another set of embodiments, the probes may be removed using corresponding "toe-hold-probes," which comprise the same sequence as the probe, as well as an extra number of bases of homology to the encoding probes (e.g., 1-20 extra bases, for example, 5 extra bases). These probes may remove the labeled readout probe through a strand-displacement interaction.

As used herein, the term "light" generally refers to electromagnetic radiation, having any suitable wavelength (or equivalently, frequency). For instance, in some embodiments, the light may include wavelengths in the optical or visual range (for example, having a wavelength of between about 400 nm and about 700 nm, i.e., "visible light"), infrared wavelengths (for example, having a wavelength of between about 300 micrometers and 700 nm), ultraviolet wavelengths (for example, having a wavelength of between about 400 nm and about 10 nm), or the like. In certain cases, as discussed in detail below, more than one entity may be used, i.e., entities that are chemically different or distinct, for example, structurally. However, in other cases, the entities may be chemically identical or at least substantially chemically identical.

In one set of embodiments, the signaling entity is "switchable," i.e., the entity can be switched between two or more states, at least one of which emits light having a desired wavelength. In the other state(s), the entity may emit no light, or emit light at a different wavelength. For instance, an entity may be "activated" to a first state able to produce light having a desired wavelength, and "deactivated" to a second state not able to emit light of the same wavelength. An entity is "photoactivatable" if it can be activated by incident light of a suitable wavelength. As a non-limiting example, Cy5, can be switched between a fluorescent and a dark state in a controlled and reversible manner by light of different wavelengths, i.e., 633 nm (or 642 nm, 647 nm, 656 nm) red light can switch or deactivate Cy5 to a stable dark state, while 405 nm green light can switch or activate the Cy5 back to the fluorescent state. In some cases, the entity can be reversibly switched between the two or more states, e.g., upon exposure to the proper stimuli. For example, a first stimuli (e.g., a first wavelength of light) may be used to activate the switchable entity, while a second stimuli (e.g., a second wavelength of light) may be used to deactivate the switchable entity, for instance, to a non-emitting state. Any suitable method may be used to activate the entity. For example, in one embodiment, incident light of a suitable wavelength may be used to activate the entity to emit light, i.e., the entity is "photoswitchable." Thus, the photoswitchable entity can be switched between different light-emitting or non-emitting states by incident light, e.g., of different wavelengths. The light may be monochromatic (e.g., produced using a laser) or polychromatic. In another embodiment, the entity may be activated upon stimulation by electric field and/or magnetic field. In other embodiments, the entity may be activated upon exposure to a suitable chemical environment, e.g., by adjusting the pH, or inducing a reversible chemical reaction involving the entity, etc. Similarly, any suitable method may be used to deactivate the entity, and the methods of activating and deactivating the entity need not be the same. For instance, the entity may be deactivated upon exposure to incident light of a suitable wavelength, or the entity may be deactivated by waiting a sufficient time.

Typically, a "switchable" entity can be identified by one of ordinary skill in the art by determining conditions under which an entity in a first state can emit light when exposed to an excitation wavelength, switching the entity from the first state to the second state, e.g., upon exposure to light of a switching wavelength, then showing that the entity, while in the second state can no longer emit light (or emits light at a much reduced intensity) when exposed to the excitation wavelength.

In one set of embodiments, as discussed, a switchable entity may be switched upon exposure to light. In some cases, the light used to activate the switchable entity may come from an external source, e.g., a light source such as a laser light source, another light-emitting entity proximate the switchable entity, etc. The second, light emitting entity, in some cases, may be a fluorescent entity, and in certain embodiments, the second, light-emitting entity may itself also be a switchable entity.

In some embodiments, the switchable entity includes a first, light-emitting portion (e.g., a fluorophore), and a second portion that activates or "switches" the first portion. For example, upon exposure to light, the second portion of the switchable entity may activate the first portion, causing the first portion to emit light. Examples of activator portions include, but are not limited to, Alexa Fluor 405 (Invitrogen), Alexa Fluor 488 (Invitrogen), Cy2 (GE Healthcare), Cy3 (GE Healthcare), Cy3B (GE Healthcare), Cy3.5 (GE Healthcare), or other suitable dyes. Examples of light-emitting portions include, but are not limited to, Cy5, Cy5.5 (GE Healthcare), Cy7 (GE Healthcare), Alexa Fluor 647 (Invitrogen), Alexa Fluor 680 (Invitrogen), Alexa Fluor 700 (Invitrogen), Alexa Fluor 750 (Invitrogen), Alexa Fluor 790 (Invitrogen), DiD, DiR, YOYO-3 (Invitrogen), YO-PRO-3 (Invitrogen), TOT-3 (Invitrogen), TO-PRO-3 (Invitrogen) or other suitable dyes. These may linked together, e.g., covalently, for example, directly, or through a linker, e.g., forming compounds such as, but not limited to, Cy5-Alexa Fluor 405, Cy5-Alexa Fluor 488, Cy5-Cy2, Cy5-Cy3, Cy5-Cy3.5, Cy5.5-Alexa Fluor 405, Cy5.5-Alexa Fluor 488, Cy5.5-Cy2, Cy5.5-Cy3, Cy5.5-Cy3.5, Cy7-Alexa Fluor 405, Cy7-Alexa Fluor 488, Cy7-Cy2, Cy7-Cy3, Cy7-Cy3.5, Alexa Fluor 647-Alexa Fluor 405, Alexa Fluor 647-Alexa Fluor 488, Alexa Fluor 647-Cy2, Alexa Fluor 647-Cy3, Alexa Fluor 647-Cy3.5, Alexa Fluor 750-Alexa Fluor 405, Alexa Fluor 750-Alexa Fluor 488, Alexa Fluor 750-Cy2, Alexa Fluor 750-Cy3, or Alexa Fluor 750-Cy3.5. Those of ordinary skill in the art will be aware of the structures of these and other compounds, many of which are available commercially. The portions may be linked via a covalent bond, or by a linker, such as those described in detail below. Other light-emitting or activator portions may include portions having two quaternized nitrogen atoms joined by a polymethine chain, where each nitrogen is independently part of a heteroaromatic moiety, such as pyrrole, imidazole, thiazole, pyridine, quinoline, indole, benzothiazole, etc., or part of a nonaromatic amine. In some cases, there may be 5, 6, 7, 8, 9, or more carbon atoms between the two nitrogen atoms.

In certain cases, the light-emitting portion and the activator portions, when isolated from each other, may each be fluorophores, i.e., entities that can emit light of a certain, emission wavelength when exposed to a stimulus, for example, an excitation wavelength. However, when a switchable entity is formed that comprises the first fluorophore and the second fluorophore, the first fluorophore forms a first, light-emitting portion and the second fluorophore forms an activator portion that switches that activates or "switches" the first portion in response to a stimulus. For example, the switchable entity may comprise a first fluorophore directly bonded to the second fluorophore, or the first and second entity may be connected via a linker or a common entity. Whether a pair of light-emitting portion and activator portion produces a suitable switchable entity can be tested by methods known to those of ordinary skills in the art. For example, light of various wavelength can be used to stimulate the pair and emission light from the light-emitting portion can be measured to determined wither the pair makes a suitable switch.

As a non-limiting example, Cy3 and Cy5 may be linked together to form such an entity. In this example, Cy3 is an activator portion that is able to activate Cy5, the light-emission portion. Thus, light at or near the absorption maximum (e.g., near 532 nm light for Cy3) of the activation or second portion of the entity may cause that portion to activate the first, light-emitting portion, thereby causing the first portion to emit light (e.g., near 647 nm for Cy5). See, e.g., U.S. Pat. No. 7,838,302, incorporated herein by reference in its entirety. In some cases, the first, light-emitting portion can subsequently be deactivated by any suitable technique (e.g., by directing 647 nm red light to the Cy5 portion of the molecule).

Other non-limiting examples of potentially suitable activator portions include 1,5 IAEDANS, 1,8-ANS, 4-Methylumbelliferone, 5-carboxy-2,7-dichlorofluorescein, 5-Carboxyfluorescein (5-FAM), 5-Carboxynapthofluorescein, 5-Carboxytetramethylrhodamine (5-TAMRA), 5-FAM (5-Carboxyfluorescein), 5-HAT (Hydroxy Tryptamine), 5-Hydroxy Tryptamine (HAT), 5-ROX (carboxy-X-rhodamine), 5-TAMRA (5-Carboxytetramethylrhodamine), 6-Carboxyrhodamine 6G, 6-CR 6G, 6-JOE, 7-Amino-4-methylcoumarin, 7-Aminoactinomycin D (7-AAD), 7-Hydroxy-4-methylcoumarin, 9-Amino-6-chloro-2-methoxyacridine, ABQ, Acid Fuchsin, ACMA (9-Amino-6-chloro-2-methoxyacridine), Acridine Orange, Acridine Red, Acridine Yellow, Acriflavin, Acriflavin Feulgen SITSA, Alexa Fluor 350, Alexa Fluor 405, Alexa Fluor 430, Alexa Fluor 488, Alexa Fluor 500, Alexa Fluor 514, Alexa Fluor 532, Alexa Fluor 546, Alexa Fluor 555, Alexa Fluor 568, Alexa Fluor 594, Alexa Fluor 610, Alexa Fluor 633, Alexa Fluor 635, Alizarin Complexon, Alizarin Red, AMC, AMCA-S, AMCA (Aminomethylcoumarin), AMCA-X, Aminoactinomycin D, Aminocoumarin, Aminomethylcoumarin (AMCA), Anilin Blue, Anthrocyl stearate, APTRA-BTC, APTS, Astrazon Brilliant Red 4G, Astrazon Orange R, Astrazon Red 6B, Astrazon Yellow 7 GLL, Atabrine, ATTO 390, ATTO 425, ATTO 465, ATTO 488, ATTO 495, ATTO 520, ATTO 532, ATTO 550, ATTO 565, ATTO 590, ATTO 594, ATTO 610, ATTO 611X, ATTO 620, ATTO 633, ATTO 635, ATTO 647, ATTO 647N, ATTO 655, ATTO 680, ATTO 700, ATTO 725, ATTO 740, ATTO-TAG CBQCA, ATTO-TAG FQ, Auramine, Aurophosphine G, Aurophosphine, BAO 9 (Bisaminophenyloxadiazole), BCECF (high pH), BCECF (low pH), Berberine Sulphate, Bimane, Bisbenzamide, Bisbenzimide (Hoechst), bis-BTC, Blancophor FFG, Blancophor SV, BOBO-1, BOBO-3, Bodipy 492/515, Bodipy 493/503, Bodipy 500/510, Bodipy 505/515, Bodipy 530/550, Bodipy 542/563, Bodipy 558/568, Bodipy 564/570, Bodipy 576/589, Bodipy 581/591, Bodipy 630/650-X, Bodipy 650/665-X, Bodipy 665/676, Bodipy Fl, Bodipy FL ATP, Bodipy Fl-Ceramide, Bodipy R6G, Bodipy TMR, Bodipy TMR-X conjugate, Bodipy TMR-X, SE, Bodipy TR, Bodipy TR ATP, Bodipy TR-X SE, BO-PRO-1, BO-PRO-3, Brilliant Sulphoflavin FF, BTC, BTC-5N, Calcein, Calcein Blue, Calcium Crimson, Calcium Green, Calcium Green-1 $Ca^{2+}$ Dye, Calcium Green-2 $Ca^{2+}$, Calcium Green-5N $Ca^{2+}$, Calcium Green-C18 $Ca^{2+}$, Calcium Orange, Calcofluor White, Carboxy-X-rhodamine (5-ROX), Cascade Blue, Cascade Yellow, Catecholamine, CCF2 (GeneBlazer), CFDA, Chromomycin A, Chromomycin A, CL-NERF, CMFDA, Coumarin Phalloidin, CPM Methylcoumarin, CTC, CTC Formazan, Cy2, Cy3.1 8, Cy3.5, Cy3, Cy5.1 8, cyclic AMP Fluorosensor (FiCRhR), Dabcyl, Dansyl, Dansyl Amine, Dansyl Cadaverine, Dansyl Chloride, Dansyl DHPE, Dansyl fluoride, DAPI, Dapoxyl, Dapoxyl 2, Dapoxyl 3' DCFDA, DCFH (Dichlorodihydrofluorescein Diacetate), DDAO, DHR (Dihydrorhodamine 123), Di-4-ANEPPS, Di-8-ANEPPS (non-ratio), DiA (4-Di-16-ASP), Dichlorodihydrofluorescein Diacetate (DCFH), DiD-Lipophilic Tracer, DiD (DiIC18(5)), DIDS, Dihydrorhodamine 123 (DHR), DiI (DiIC18(3)), Dinitrophenol, DiO (DiOC18(3)), DiR, DiR (DiIC18(7)), DM-NERF (high pH), DNP, Dopamine, DTAF, DY-630-NHS, DY-635-NHS, DyLight 405, DyLight 488, DyLight 549, DyLight 633, DyLight 649, DyLight 680, DyLight 800, ELF 97, Eosin, Erythrosin, Erythrosin ITC, Ethidium Bromide, Ethidium homodimer-1 (EthD-1), Euchrysin, EukoLight, Europium (III) chloride, Fast Blue, FDA, Feulgen (Pararosaniline), FIF (Formaldehyd Induced Fluorescence), FITC, Flazo Orange, Fluo-3, Fluo-4, Fluorescein (FITC), Fluorescein Diacetate, Fluoro-Emerald, Fluoro-Gold (Hydroxystilbamidine), Fluor-Ruby, FluorX, FM 1-43, FM 4-46, Fura Red (high pH), Fura Red/Fluo-3, Fura-2, Fura-2/BCECF, Genacryl Brilliant Red B, Genacryl Brilliant Yellow 10GF, Genacryl Pink 3G, Genacryl Yellow 5GF, GeneBlazer (CCF2), Gloxalic Acid, Granular blue, Haematoporphyrin, Hoechst 33258, Hoechst 33342, Hoechst 34580, HPTS, Hydroxycoumarin, Hydroxystilbamidine (FluoroGold), Hydroxytryptamine, Indo-1, high calcium, Indo-1, low calcium, Indodicarbocyanine (DiD), Indotricarbocyanine (DiR), Intrawhite Cf, JC-1, JO-JO-1, JO-PRO-1, LaserPro, Laurodan, LDS 751 (DNA), LDS 751 (RNA), Leucophor PAF, Leucophor SF, Leucophor WS, Lissamine Rhodamine, Lissamine Rhodamine B, Calcein/Ethidium homodimer, LOLO-1, LO-PRO-1, Lucifer Yellow, Lyso Tracker Blue, Lyso Tracker Blue-White, Lyso Tracker Green, Lyso Tracker Red, Lyso Tracker Yellow, LysoSensor Blue, LysoSensor Green, LysoSensor Yellow/Blue, Mag Green, Magdala Red (Phloxin B), Mag-Fura Red, Mag-Fura-2, Mag-Fura-5, Mag-Indo-1, Magnesium Green, Magnesium Orange, Malachite Green, Marina Blue, Maxilon Brilliant Flavin 10 GFF, Maxilon Brilliant Flavin 8 GFF, Merocyanin, Methoxycoumarin, Mitotracker Green FM, Mitotracker Orange, Mitotracker Red, Mitramycin, Monobromobimane, Monobromobimane (mBBr-GSH), Monochlorobimane, MPS (Methyl Green Pyronine Stilbene), NBD, NBD Amine, Nile Red, Nitrobenzoxadidole, Noradrenaline, Nuclear Fast Red, Nuclear Yellow, Nylosan Brilliant Iavin E8G, Oregon Green, Oregon Green 488-X, Oregon Green, Oregon Green 488, Oregon Green 500, Oregon Green 514, Pacific Blue, Pararosaniline (Feulgen), PBFI, Phloxin B (Magdala Red), Phorwite AR, Phorwite BKL, Phorwite Rev, Phorwite RPA, Phosphine 3R, PKH26 (Sigma), PKH67, PMIA, Pontochrome Blue Black, POPO-1, POPO-3, PO-PRO-1, PO-PRO-3, Primuline, Procion Yellow, Propidium Iodid (PI), PyMPO, Pyrene, Pyronine, Pyronine B, Pyrozal Brilliant Flavin 7GF, QSY 7, Quinacrine Mustard, Resorufin, RH 414, Rhod-2, Rhodamine, Rhodamine 110, Rhodamine 123, Rhodamine 5 GLD, Rhodamine 6G, Rhodamine B, Rhodamine B 200, Rhodamine B extra, Rhodamine BB, Rhodamine BG, Rhodamine Green, Rhodamine Phallicidine, Rhodamine Phalloidine, Rhodamine Red, Rhodamine WT, Rose Bengal, S65A, S65C, S65L, S65T, SBFI, Serotonin, Sevron Brilliant Red 2B, Sevron Brilliant Red 4G, Sevron Brilliant Red B, Sevron Orange, Sevron Yellow L, SITS, SITS (Primuline), SITS (Stilbene Isothiosulphonic Acid), SNAFL calcein, SNAFL-1, SNAFL-2, SNARF calcein, SNARF1, Sodium Green, SpectrumAqua, SpectrumGreen, SpectrumOrange, Spectrum Red, SPQ (6-methoxy-N-(3-sulfopropyl)quinolinium), Stilbene, Sulphorhodamine B can C, Sulphorhodamine Extra, SYTO 11, SYTO 12, SYTO 13, SYTO 14, SYTO 15, SYTO 16, SYTO 17, SYTO 18, SYTO 20, SYTO 21, SYTO 22, SYTO 23, SYTO 24, SYTO 25, SYTO 40, SYTO 41, SYTO 42, SYTO 43, SYTO 44, SYTO 45, SYTO 59, SYTO 60, SYTO 61, SYTO 62, SYTO 63, SYTO 64, SYTO 80, SYTO 81, SYTO 82, SYTO 83, SYTO 84, SYTO 85, SYTOX Blue, SYTOX Green, SYTOX Orange, Tetracycline, Tetramethylrhodamine (TAMRA), Texas Red, Texas Red-X conjugate, Thiadicarbocyanine (DiSC3), Thiazine Red R, Thiazole Orange, Thioflavin 5, Thioflavin S, Thioflavin TCN, Thiolyte, Thiozole Orange, Tinopol CBS (Calcofluor White), TMR, TO-PRO-1, TO-PRO-3, TO-PRO-5, TOTO-1, TOTO-3, TRITC (tetramethylrodamine isothiocyanate), True Blue, TruRed, Ultralite, Uranine B, Uvitex SFC, WW 781, X-Rhodamine, XRITC, Xylene Orange, Y66F, Y66H, Y66W, YO-PRO-1, YO-PRO-3, YOYO-1, YOYO-3, SYBR Green, Thiazole orange (interchelating dyes), or combinations thereof.

Another aspect of the invention is directed to a computer-implemented method. For instance, a computer and/or an automated system may be provided that is able to automatically and/or repetitively perform any of the methods described herein. As used herein, "automated" devices refer to devices that are able to operate without human direction, i.e., an automated device can perform a function during a period of time after any human has finished taking any action to promote the function, e.g. by entering instructions into a computer to start the process. Typically, automated equipment can perform repetitive functions after this point in time. The processing steps may also be recorded onto a machine-readable medium in some cases.

For example, in some cases, a computer may be used to control imaging of the sample, e.g., using fluorescence microscopy, STORM or other super-resolution techniques such as those described herein. In some cases, the computer may also control operations such as drift correction, physical registration, hybridization and cluster alignment in image analysis, cluster decoding (e.g., fluorescent cluster decoding), error detection or correction (e.g., as discussed herein), noise reduction, identification of foreground features from background features (such as noise or debris in images), or the like. As an example, the computer may be used to control activation and/or excitation of signaling entities within the sample, and/or the acquisition of images of the signaling entities. In one set of embodiments, a sample may be excited using light having various wavelengths and/or intensities, and the sequence of the wavelengths of light used to excite the sample may be correlated, using a computer, to the images acquired of the sample containing the signaling entities. For instance, the computer may apply light having various wavelengths and/or intensities to a sample to yield different average numbers of signaling entities in each region of interest (e.g., one activated entity per location, two activated entities per location, etc.). In some cases, this information may be used to construct an image and/or determine the locations of the signaling entities, in some cases at high resolutions, as noted above.

In some aspects, the sample is positioned on a microscope. In some cases, the microscope may contain one or more channels, such as microfluidic channels, to direct or control fluid to or from the sample. For instance, in one embodiment, nucleic acid probes such as those discussed herein may be introduced and/or removed from the sample by flowing fluid through one or more channels to or from the sample. In some cases, there may also be one or more chambers or reservoirs for holding fluid, e.g., in fluidic communication with the channel, and/or with the sample.

Those of ordinary skill in the art will be familiar with channels, including microfluidic channels, for moving fluid to or from a sample.

As used herein, "microfluidic," "microscopic," "microscale," the "micro-" prefix (for example, as in "microchannel"), and the like generally refers to elements or articles having widths or diameters of less than about 1 mm, and less than about 100 microns (micrometers) in some cases. In some embodiments, larger channels may be used instead of, or in conjunction with, microfluidic channels for any of the embodiments discussed herein. For examples, channels having widths or diameters of less than about 10 mm, less than about 9 mm, less than about 8 mm, less than about 7 mm, less than about 6 mm, less than about 5 mm, less than about 4 mm, less than about 3 mm, or less than about 2 mm may be used in certain instances. In some cases, the element or article includes a channel through which a fluid can flow. In all embodiments, specified widths can be a smallest width (i.e. a width as specified where, at that location, the article can have a larger width in a different dimension), or a largest width (i.e. where, at that location, the article has a width that is no wider than as specified, but can have a length that is greater). Thus, for instance, the microfluidic channel may have an average cross-sectional dimension (e.g., perpendicular to the direction of flow of fluid in the microfluidic channel) of less than about 1 mm, less than about 500 microns, less than about 300 microns, or less than about 100 microns. In some cases, the microfluidic channel may have an average diameter of less than about 60 microns, less than about 50 microns, less than about 40 microns, less than about 30 microns, less than about 25 microns, less than about 10 microns, less than about 5 microns, less than about 3 microns, or less than about 1 micron.

A "channel," as used herein, means a feature on or in an article (e.g., a substrate) that at least partially directs the flow of a fluid. In some cases, the channel may be formed, at least in part, by a single component, e.g. an etched substrate or molded unit. The channel can have any cross-sectional shape, for example, circular, oval, triangular, irregular, square or rectangular (having any aspect ratio), or the like, and can be covered or uncovered (i.e., open to the external environment surrounding the channel). In embodiments where the channel is completely covered, at least one portion of the channel can have a cross-section that is completely enclosed, and/or the entire channel may be completely enclosed along its entire length with the exception of its inlet and outlet.

A channel may have any aspect ratio, e.g., an aspect ratio (length to average cross-sectional dimension) of at least about 2:1, more typically at least about 3:1, at least about 5:1, at least about 10:1, etc. As used herein, a "cross-sectional dimension," in reference to a fluidic or microfluidic channel, is measured in a direction generally perpendicular to fluid flow within the channel. A channel generally will include characteristics that facilitate control over fluid transport, e.g., structural characteristics and/or physical or chemical characteristics (hydrophobicity vs. hydrophilicity) and/or other characteristics that can exert a force (e.g., a containing force) on a fluid. The fluid within the channel may partially or completely fill the channel. In some cases the fluid may be held or confined within the channel or a portion of the channel in some fashion, for example, using surface tension (e.g., such that the fluid is held within the channel within a meniscus, such as a concave or convex meniscus). In an article or substrate, some (or all) of the channels may be of a particular size or less, for example, having a largest dimension perpendicular to fluid flow of less than about 5 mm, less than about 2 mm, less than about 1 mm, less than about 500 microns, less than about 200 microns, less than about 100 microns, less than about 60 microns, less than about 50 microns, less than about 40 microns, less than about 30 microns, less than about 25 microns, less than about 10 microns, less than about 3 microns, less than about 1 micron, less than about 300 nm, less than about 100 nm, less than about 30 nm, or less than about 10 nm or less in some cases. In one embodiment, the channel is a capillary.

A variety of materials and methods, according to certain aspects of the invention, can be used to form devices or components containing microfluidic channels, chambers, etc. For example, various devices or components can be formed from solid materials, in which the channels can be formed via micromachining, film deposition processes such as spin coating and chemical vapor deposition, physical vapor deposition, laser fabrication, photolithographic techniques, etching methods including wet chemical or plasma processes, electrodeposition, and the like. See, for example, *Scientific American*, 248:44-55, 1983 (Angell, et al).

In one set of embodiments, various structures or components can be formed of a polymer, for example, an elastomeric polymer such as polydimethylsiloxane ("PDMS"), polytetrafluoroethylene ("PTFE" or Teflon®), or the like. For instance, according to one embodiment, a channel such as a microfluidic channel may be implemented by fabricating the fluidic system separately using PDMS or other soft lithography techniques (details of soft lithography techniques suitable for this embodiment are discussed in the references entitled "Soft Lithography," by Younan Xia and George M. Whitesides, published in the *Annual Review of Material Science*, 1998, Vol. 28, pages 153-184, and "Soft Lithography in Biology and Biochemistry," by George M. Whitesides, Emanuele Ostuni, Shuichi Takayama, Xingyu Jiang and Donald E. Ingber, published in the *Annual Review of Biomedical Engineering*, 2001, Vol. 3, pages 335-373; each of these references is incorporated herein by reference).

Other examples of potentially suitable polymers include, but are not limited to, polyethylene terephthalate (PET), polyacrylate, polymethacrylate, polycarbonate, polystyrene, polyethylene, polypropylene, polyvinylchloride, cyclic olefin copolymer (COC), polytetrafluoroethylene, a fluorinated polymer, a silicone such as polydimethylsiloxane, polyvinylidene chloride, bis-benzocyclobutene ("BCB"), a polyimide, a fluorinated derivative of a polyimide, or the like. Combinations, copolymers, or blends involving polymers including those described above are also envisioned. The device may also be formed from composite materials, for example, a composite of a polymer and a semiconductor material.

In some embodiments, various microfluidic structures or components of the device are fabricated from polymeric and/or flexible and/or elastomeric materials, and can be conveniently formed of a hardenable fluid, facilitating fabrication via molding (e.g. replica molding, injection molding, cast molding, etc.). The hardenable fluid can be essentially any fluid that can be induced to solidify, or that spontaneously solidifies, into a solid capable of containing and/or transporting fluids contemplated for use in and with the fluidic network. In one embodiment, the hardenable fluid comprises a polymeric liquid or a liquid polymeric precursor (i.e. a "prepolymer"). Suitable polymeric liquids can include, for example, thermoplastic polymers, thermoset polymers, waxes, metals, or mixtures or composites thereof heated above their melting point. As another example, a suitable polymeric liquid may include a solution of one or more polymers in a suitable solvent, which solution forms a solid polymeric material upon removal of the solvent, for example, by evaporation. Such polymeric materials, which can be solidified from, for example, a melt state or by solvent evaporation, are well known to those of ordinary skill in the art. A variety of polymeric materials, many of which are elastomeric, are suitable, and are also suitable for forming molds or mold masters, for embodiments where one or both of the mold masters is composed of an elastomeric material. A non-limiting list of examples of such polymers includes polymers of the general classes of silicone polymers, epoxy polymers, and acrylate polymers. Epoxy polymers are characterized by the presence of a three-membered cyclic ether group commonly referred to as an epoxy group, 1,2-epoxide, or oxirane. For example, diglycidyl ethers of bisphenol A can be used, in addition to compounds based on aromatic amine, triazine, and cycloaliphatic backbones. Another example includes the well-known Novolac polymers. Non-limiting examples of silicone elastomers suitable for use according to the invention include those formed from precursors including the chlorosilanes such as methylchlorosilanes, ethylchlorosilanes, phenylchlorosilanes, etc.

Silicone polymers are used in certain embodiments, for example, the silicone elastomer polydimethylsiloxane. Non-limiting examples of PDMS polymers include those sold under the trademark Sylgard by Dow Chemical Co., Midland, MI, and particularly Sylgard 182, Sylgard 184, and Sylgard 186. Silicone polymers including PDMS have several beneficial properties simplifying fabrication of various structures of the invention. For instance, such materials are inexpensive, readily available, and can be solidified from a prepolymeric liquid via curing with heat. For example, PDMSs are typically curable by exposure of the prepolymeric liquid to temperatures of about, for example, about 65° C. to about 75° C. for exposure times of, for example, at least about an hour. Also, silicone polymers, such as PDMS, can be elastomeric and thus may be useful for forming very small features with relatively high aspect ratios, necessary in certain embodiments of the invention. Flexible (e.g., elastomeric) molds or masters can be advantageous in this regard.

One advantage of forming structures such as microfluidic structures or channels from silicone polymers, such as PDMS, is the ability of such polymers to be oxidized, for example by exposure to an oxygen-containing plasma such as an air plasma, so that the oxidized structures contain, at their surface, chemical groups capable of cross-linking to other oxidized silicone polymer surfaces or to the oxidized surfaces of a variety of other polymeric and non-polymeric materials. Thus, structures can be fabricated and then oxidized and essentially irreversibly sealed to other silicone polymer surfaces, or to the surfaces of other substrates reactive with the oxidized silicone polymer surfaces, without the need for separate adhesives or other sealing means. In most cases, sealing can be completed simply by contacting an oxidized silicone surface to another surface without the need to apply auxiliary pressure to form the seal. That is, the pre-oxidized silicone surface acts as a contact adhesive against suitable mating surfaces. Specifically, in addition to being irreversibly sealable to itself, oxidized silicone such as oxidized PDMS can also be sealed irreversibly to a range of oxidized materials other than itself including, for example, glass, silicon, silicon oxide, quartz, silicon nitride, polyethylene, polystyrene, glassy carbon, and epoxy polymers, which have been oxidized in a similar fashion to the PDMS surface (for example, via exposure to an oxygen-containing plasma). Oxidation and sealing methods useful in the context of the present invention, as well as overall molding techniques, are described in the art, for example, in an article entitled "Rapid Prototyping of Microfluidic Systems and Polydimethylsiloxane," Anal. Chem., 70:474-480, 1998 (Duffy et al.), incorporated herein by reference.

The following documents are each incorporated herein by reference in their entireties: U.S. Pat. No. 7,838,302, issued Nov. 23, 2010, entitled "Sub-Diffraction Limit Image Resolution and Other Imaging Techniques," by Zhuang, et al.; U.S. Pat. No. 8,564,792, issued Oct. 22, 2013, entitled "Sub-diffraction Limit Image Resolution in Three Dimensions," by Zhuang, et al.; and Int. Pat. Apl. Pub. No. WO 2013/090360, published Jun. 20, 2013, entitled "High Resolution Dual-Objective Microscopy," by Zhuang, et al.

In addition, incorporated herein by reference in their entireties are U.S. Provisional Patent Application Ser. No. 62/031,062, filed Jul. 30, 2014, entitled "Systems and Methods for Determining Nucleic Acids," by Zhuang, et al.; U.S. Provisional Patent Application Ser. No. 62/050,636, filed Sep. 15, 2014, entitled "Probe Library Construction," by Zhuang, et al.; U.S. Provisional Patent Application Ser. No. 62/142,653, filed Apr. 3, 2015, entitled "Systems and Methods for Determining Nucleic Acids," by Zhuang, et al.; and a PCT application filed on even date herewith, entitled "Probe Library Construction," by Zhuang, et al.

The following examples are intended to illustrate certain embodiments of the present invention, but do not exemplify the full scope of the invention.

Example 1

The example presents a platform to enable the simultaneous detection of the number and spatial organization of thousands of distinct mRNAs within single cells with high efficiency and low error-rate using a novel form of highly multiplexed fluorescence in situ hybridization (FISH). This example accomplishes these measurements by integrating and innovating methods for massively parallel probe synthesis, super-resolution imaging, and self-correcting error-checking codes.

Here, these examples present methods for the simultaneous detection of some or all of the thousands of unique RNAs expressed in a cell. This approach not only promises to revolutionize the throughput of the already effective single-molecule FISH (smFISH) approach, but also allows researchers to benefit from the hypothesis free discovery approach which has made other whole-genome systems approaches to biology so effective. For example, this whole genome approach may allow researchers to discover RNAs whose expression levels and/or subcellular localization patterns change under certain conditions of interest, such as disease states, without knowing, a priori, which mRNA will change in abundance or localization. Simultaneous measurements of hundreds of genes within a single cell also allow for the identification of correlations between genes in expression and localization patterns in some cases.

This can be achieved using methods for highly multiplexed smFISH via the sequential hybridization of orthogonal detection probes and super-resolution imaging, reducing the cost of probe synthesis, and the development of a highly automated system to minimize demands on the user, as discussed herein. This provides an integrated platform to handle the bioinformatics of probe design, the mathematics of error-correcting codes, the complexity of image registration and analysis, and the cumbersome fluid handling through a simple suite of user friendly interfaces. This integration allows easy operation with limited user training and facilitates the rapid collection of data.

This example illustrates: (1) computational design of "codewords" to attach to all RNA targets in the cell that will allow unique identification of each RNA with some degree of experimental error tolerance, (2) translation of these codewords into nucleotide sequences and synthesis of the required single-stranded (ss) oligonucleotide (e.g. ssDNA) probes, (3) sample fixation and hybridization of these probes to the RNA targets in situ, (4) read-out of these codewords via successive rounds of hybridization of distinct fluorescent probes imaged with conventional fluorescence microscopy or super-resolution fluorescence microscopy, and (5) automated decoding of measured codewords combined with computational error correction to uniquely and robustly identify individual mRNAs.

In the first step, a "codeword" is assigned to every RNA that is to be labeled. In a typical design these may be strings of N binary letters or positions. Codewords may be chosen from the same wide range of existing error tolerant or error-correcting encoding schemes developed for digital storage and communication, e.g., using Hamming codes or the like. For example, actin-RNA may be assigned the binary codeword 11001010. Each codeword may be unique and separated from the other codewords by a Hamming distance, h, which measures the number of letters or positions that must be incorrectly read for one codeword to be misinterpreted as a different one. A Hamming distance greater than 1 between all codewords allows for some measurement errors to be detected-since simple errors would produce codewords that are not used to encode RNAs. For a Hamming distance larger than 2, it is also possible to correct some errors, as codewords with one error will be closest in Hamming distance to a single, unique codeword. The total number of different RNAs to be detected from the transcriptome and the amount of error correction desired determines the length of the codewords. Information theory provides several efficient algorithms for assembling error-correcting binary codebooks.

Figure 1B:
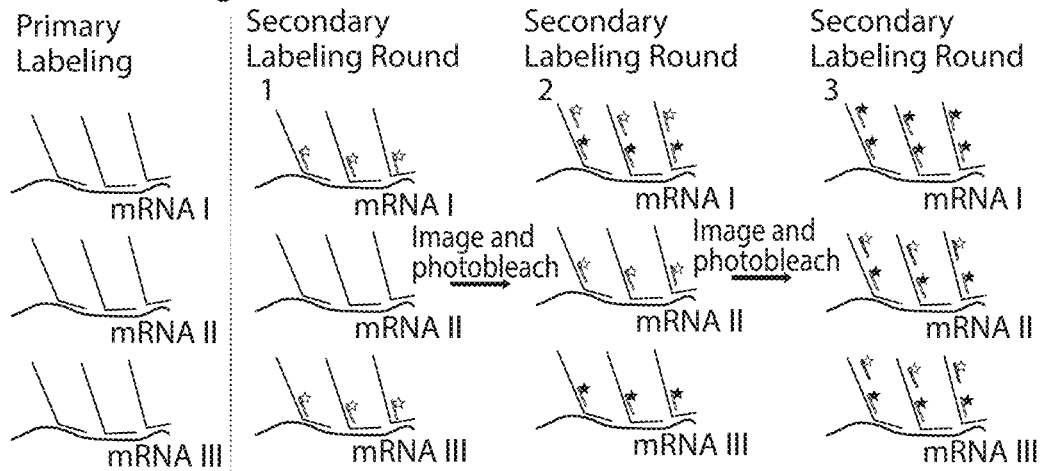
Figure 1C:
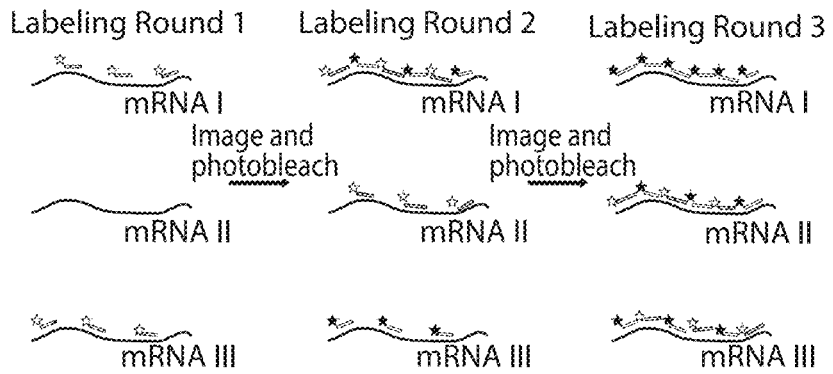

In the second step, this encoding scheme is translated into a set of oligonucleotide (e.g. DNA) probe sequences, which can be called primary probes or encoding probes, each of which not only targets a probe to the RNA of interest but also encodes the unique binary codeword within a set of secondary binding sites (FIGS. 1A-1C). For example, first designed may be primary binding sequences for each targeted mRNA. These sequences are "target sequences" that are comprised of complementary nucleotide sequences to their target RNAs computationally selected to satisfy a stringent set of hybridization conditions, including uniqueness in the target genome. To improve the efficiency of hybridization to individual mRNAs, multiple primary target sequences are designed for each individual RNA. Then each position within the set of codewords is assigned a unique oligonucleotide (e.g. DNA) sequence, which is called a read sequence. These tags are designed as to have no interaction with endogenous mRNA sequences or each other. For instance, for all the value "1"s in a codeword of an individual mRNA, the corresponding read sequence is attached to the primary targeting sequences against that mRNA. In general, each probe will contain a target sequence and one or more read sequences. If the total length of the necessary read sequences and the primary target sequence exceeds synthesis capabilities, then subsets of the read sequences can be appended to distinct target sequences. For example, consider the potential codeword 11001010 for actin. Probe sequences for this RNA could contain the read sequences corresponding to positions 1, 2, 5, and 7 in the codeword attached to a variety of target sequences specific to actin. After all the sequences have been designed, the resulting complex set of unique custom oligonucleotide (e.g. DNA) sequences is manufactured and amplified using methods as described below.

In the third step, the resulting pool of DNA is hybridized, e.g., to fixed, permeabilized cells. In this process, individual probes may be attached to every RNA in the cell by hybridization of their corresponding target sequences with the RNA while the read sequences remain free to bind the appropriate secondary probes as discussed below.

In the fourth step—the read-out step—fluorescently labeled secondary nucleic acid probes (also called readout probes) are successively hybridized to the read sequences attached to the target sequences that binds to the mRNA targets in the above step. When simultaneously imaging a large number of different RNA species in cells, the density of labeled RNAs may exceed that at which each RNA can be resolved via conventional imaging methods. Thus, this may be performed using a super-resolution imaging method, for example STORM (stochastic optical reconstruction microscopy), to resolve the labeled molecules. After each round of hybridization and imaging with the secondary probes, the fluorophores are quenched or otherwise inactivated either via chemical or optical techniques such as oxidation, chemically bleaching, photobleaching, stringent washing or enzymatic digestion, etc. The sample is then stained with the next secondary probe, and the cycle continues until all positions of the codewords have been read out. In the simplest incarnation, there will be one hybridization step for each position within the codeword, e.g. 8 hybridization steps for an 8-letter codeword (FIGS. 1A-1C).

FIGS. 1A-1C show schematic diagrams of this example. FIG. 1A shows that every position of the codewords is assigned a unique oligonucleotide sequence when this position has a value "1." All mRNA codewords are then translated into combinations of read sequences, which are attached to the targeting sequence. FIG. 1B shows various steps of the labeling scheme of this example. In the first step, all mRNAs (I-III) are tagged with multiple oligonucleotide (e.g. ssDNA) probes comprising a primary targeting sequence, which hybridizes to the RNA of interest, and a "tail" (i.e. containing read sequences) carrying the translated codeword, which does not interact with endogenous nucleotide sequences. In the next step, the first secondary probe is added, which can bind all probes whose tails have a read sequence corresponding to the value of "1" in the first position. The dyes on these secondary probes are imaged and bleached, then the next secondary probe is added to bind probes attached to mRNA which have a value of "1" in the second position of their assigned codeword, and so on.

In the final step, the microscopy images from each staining and imaging round are aligned, for example, computationally (e.g. using fiducial beads or other markers tracked during image acquisition), and the clusters of localizations resolved by conventional fluorescence microscopy or super-resolution imaging (e.g. STORM) from the different rounds are identified. These clusters of localizations arise from individual target mRNA molecules, and the hybridization rounds in which a spot was detected in a given cluster correspond to the "1" in the codeword for that mRNA. If there are no missed-detection events or false positive signal in the images, this codeword will perfectly match one of the expected codewords. FIGS. 1A-1C describe an example in which the codeword has three letters, i.e. three positions, and the three target mRNAs have codewords 110, 101, and 011 assigned to them. In real experimental examples, the codeword could contain more digits. For example, the mRNA for actin can be assigned the codeword, 11001010. In that case, detected clusters containing overlapping localization signals in the 1st, 2nd, 5th and 7th hybridization steps (meaning the 1st, 2nd, 5th and 7th secondary probes bound to this site) can be identified as individual actin mRNA molecules, since the pattern of positive bindings matches the codeword of actin (11001010). In addition, if there are missed-detection events or false positive signals in the image data, these aberrations can be corrected by the implemented error-correction scheme. For example, clusters of localizations with a detected codeword that has only one digit discrepancy from 11001010 (such as 11000010 or 11101010) can also be identified as actin mRNA since all other valid codeword in this example differ from the detected pattern in two more positions.

Example 2

This example describes another alternative approach that differs in several of the steps described above. This approach begins with the first step, construction of the codewords to the desired mRNA targets, as described above.

In the second step of this approach, nucleic acid probes are designed that bind uniquely to the mRNA targets of interest, as described above. However, instead of appending unique read sequences to these targeting sequences, unique pools or groups of probes are constructed from these target sequences. Each pool comprises all or a subset of the sequences that target all mRNAs which contain the same value at a given position in their codeword. For example, the first pool would have of all or a subset of the target sequences designed for all mRNAs that contain a 1 in the first position of their codewords, e.g. 110 and 101 but not 011; the second pool would have of all or a subset of the target sequences designed for all mRNAs that contain a 1 in the second position of their codewords, e.g. 110 and 011 but not 101; the third pool would have of all or a subset of the target sequences designed for all mRNAs that contain a 1 in the third position of their codewords, e.g. 011 and 101 but not 110 (FIG. 1C). As another example, consider the potential codeword 11001010 for actin. Probes that target this mRNA would be included in pools 1, 2, 5, and 7 but not in pools 3, 4, 6, and 8. The same target to a given mRNA may or may not be included in pools. For example, a probe that targets the same region of actin may be included in pools 1, 2, 5, and 7 or any subset of these pools. After all of the pools have been designed, each complex set of unique, custom oligonucleotide sequences is manufactured and amplified using methods as described below.

In the third step of this approach, the first pool of probes is hybridized, e.g., to fixed, permeabilized cells. In this process, the fluorophores attached to each of the probes in this pool are bound to each of the targets of that pool. The binding of these probes is then determined by fluorescence microscopy. As described above, these images can be collected either via a range of methods including both conventional fluorescence imaging or super-resolution imaging methods such as STORM. After a round of imaging, the probes from the first pool are inactivated or removed from the sample via the methods described above. This process is then repeated for each successive pool of probes until some or all of the pools have been applied to the sample and imaged such that all positions in the codewords have been read out. In the simplest incarnation, there will be one hybridization and imaging step for each position in the codeword, e.g. 3 rounds of hybridization and imaging for a codeword with 3 positions (FIG. 1C) or 8 rounds of hybridization and imaging for a codeword with 8 positions.

The final step of this approach is identical to that described above.

Example 3

In this example, 14 genes (PGK1, H3F3B, PKM, ENO1, GPI, EEF2, GNAS, HSPA8, GAPDH, CALM1, RHOA, PPIA, UBA52, and VCP) were encoded using a subset of the (8,4) SECDED code (FIGS. 2A-2E). To determine the accuracy of these measurements, the measured abundances of these 14 mRNAs were compared to the abundances measured from bulk RNA-seq of A549 cells (published ENCODE data). Remarkably, it was found that there was excellent agreement between these two measurements, as the transcripts count measured using the sequential hybridization approach correlated with gene expression measured using RNA-seq with a Pearson correlation coefficient r of 0.75 (FIG. 2F). Gene expression from 3 other cells were also measured, and it was found that the gene expression of these 14 genes was highly correlated among the cells with a r of 0.96 (FIG. 2G).

Codebook Design. Each mRNA in the target set was assigned a binary codeword using a Single Error Correction Double Error Detection (SECDED) code. SECDED is an extended Hamming codebook with an additional parity bit. Briefly, Matlab's Communications System toolbox was used to generate SECDED codes of either 8 or 16 letters or positions. In both cases, only those codewords containing four is were used. These words were assigned at random to mRNAs in the target set. [0 1 0 1 1 1 0 0] is an example of the 8-letter codewords used (i.e., these codewords each contained four is and four 0s.) [0 1 0 1 1 1 0 0 0 0 0 0 0 0 0 0] is an example of the 16-letter codewords used (i.e., each codeword contained four is and twelve 0s). Not every codeword was necessarily assigned to an mRNA.

Computational Assembly of ssDNA Primary Probe Sequence. The number of primary nucleic acid probes used for hybridization with mRNA targets ranged from 200 to 2000 unique oligonucleotides, depending on the experiment. For example, to label 14 mRNAs with 28 oligos targeting each gene, 392 unique sequences were used. Large number of oligos with unique sequences were purchased in a pool from LC Sciences or CustomArray. However, array synthesized oligos were in minute quantity that was insufficient for in situ hybridization. The protocol for their amplification are described below.

Each primary probe contained three components: flanking primer sequences to allow enzymatic amplification of probes, targeting sequence for in situ hybridization to mRNAs, and secondary tag sequence containing one or more read sequences for sequential readout of codewords.

The following is an example of a primary probe:

(SEQ ID NO: 1)
GTTGGCGACGAAAGCACTGC<u>GATTGGAACCGTCCCAAGCGTTGCG</u>

CTTAATGGATCATCAATTTTGTCTCACTAC<u>GACGGTCAATCGCGC</u>

<u>TGCATACTTGCGTCGGTCGGA</u>CAAACGAGG

The components are arranged in the following order: forward primer (not underlined), secondary read sequence 1 (underlined), mRNA targeting sequence (not underlined), secondary read sequence 2 (underlined), and reverse primer (not underlined). The secondary read sequences are the reverse complement of the corresponding secondary probes. Since only codewords that contained four '1's were used, the primary probes for each mRNA needed to contain 4 different secondary read sequences in this example. However, in order to reduce the overall length of the primary probes, the pool of targeting sequences for each mRNA target was split at random into two pools. Two secondary read sequences are attached each probe in one of the two pools and the other two secondary read sequences are attached the probes in the other pool. The design criteria for each component are described below.

Primer Design. Specific index primers were generated by a collection of 240,000 published sequences of orthogonal 25-bp long sequences. These sequences were trimmed to 20 bp, selected for a narrow 70 to 80° C. melting temperature, the absence of consecutive repeats of 3 or more base, and the presence of a GC clamp, i.e. one of the two 3' terminal bases must be G or C. To further improve specificity, these sequences were then screened against the human genome using BLAST+ (Camacho et al 2009), and primers with 14 or more contiguous bases of homology were eliminated. In a subsequent screening via BLAST+, primers that shared 11 or more contiguous bases or more than 5 bases at the 3' end of any other primer or the T7 promoter were also removed.

Secondary Probes Design. 30-bp long secondary probe sequences were created by concatenating fragments of the orthogonal primer set described above. These secondaries were then screened for orthogonality with other secondaries (no more than 11 basepairs of homology) and for potential off-target binding sites in the human genome (no more than 14 basepairs of homology). Secondary sequences used in this example are provided in Table 1.

TABLE 1

| Bit | Secondary sequences | Sequence number |
|---|---|---|
| B1 | CGCAACGCTTGGGAC GGTTCCAATCGGATC | SEQ ID NO: 2 |
| B2 | CGAATGCTCTGGCCT CGAACGAACGATAGC | SEQ ID NO: 3 |
| B3 | ACAAATCCGACCAGA TCGGACGATCATGGG | SEQ ID NO: 4 |
| B4 | CAAGTATGCAGCGCG ATTGACCGTCTCGTT | SEQ ID NO: 5 |
| B5 | TGCGTCGTCTGGCTA GCACGGCACGCAAAT | SEQ ID NO: 6 |
| B6 | AAGTCGTACGCCGAT GCGCAGCAATTCACT | SEQ ID NO: 7 |
| B7 | CGAAACATCGGCCAC GGTCCCGTTGAACTT | SEQ ID NO: 8 |
| B8 | ACGAATCCACCGTCC AGCGCGTCAAACAGA | SEQ ID NO: 9 |
| B9 | CGCGAAATCCCCGTA ACGAGCGTCCCTTGC | SEQ ID NO: 10 |
| B10 | GCATGAGTTGCCTGG CGTTGCGACGACTAA | SEQ ID NO: 11 |
| B11 | CCGTCGTCTCCGGTC CACCGTTGCGCTTAC | SEQ ID NO: 12 |
| B12 | GGCCAATGGCCCAGG TCCGTCACGCAATTT | SEQ ID NO: 13 |

TABLE 1-continued

| Bit | Secondary sequences | Sequence number |
|---|---|---|
| B13 | TTGATCGAATCGGAG CGTAGCGGAATCTGC | SEQ ID NO: 14 |
| B14 | CGCGCGGATCCGCTT GTCGGGAACGGATAC | SEQ ID NO: 15 |
| B15 | GCCTCGATTACGACG GATGTAATTCGGCCG | SEQ ID NO: 16 |
| B16 | GCCCGTATTCCCGCT TGCGAGTAGGGCAAT | SEQ ID NO: 17 | mRNA Targeting Sequence Design. To determine the relative abundance of all the isoforms of all genes expressed in these cell lines, transcriptome profiling data from the ENCODE project for total RNA from A549 and IMR90 cells was processed using the publicly available software cufflinks, along with human genome annotations from gencode v18. Gene models corresponding to the most highly expressed isoform were used to build a sequence library in FASTA format recording the dominant isoform of every gene. Genes of interest were selected from this library. These genes were partitioned into 1 kb segments, then the software OligoArray2.1 was used to generate primary probe sequences for the human transcriptome with the following constraints: 30-bp or 40-bp length, depending on the experiment; probe-target melting temperatures greater than 70° C. (variable parameter); no cross hybridization targets with melting temperatures greater than 72° C. (variable parameter); no predicted internal secondary structures with melting temperatures greater than 76° C. (variable parameter); and no single-nucleotide contiguous repeats of 6 or more bases. After OligoArray probe selection, all potential probes that mapped to a different gene were rejected while all potential probes with multiple alignments to the same gene were retained. A BLAST database was assembled from the FASTA library of all expressed genes to screen for probes' uniqueness. For each gene, 14 to 28 targeting sequences produced during the OligoArray processing were selected.

Probe Synthesis—index PCR. The template for specific probe sets were selected from the complex oligopool via limited-cycle PCR. Briefly, 0.5 to 1 ng of the complex oligopool was combined with 0.5 micromolar of each primer. The forward primer matched the priming sequence for the desired subset while the reverse primer was a 5' concatenation of this sequence with a T7 promoter. To avoid the generation of G-quadruplets, which can be difficult to synthesize, the terminal Gs required in the T7 promoter were generated from Gs located at the 5' of the priming region where appropriate. All primers were synthesized by IDT. A 50 microliter reaction volume was amplified either using the KAPA real-time library amplification kit (KAPA Biosystems; KK2701) or via a homemade qPCR mix which included 0.8x EvaGreen (Biotum; 31000-T) and the hot-start Phusion polymerase (New England Biolabs; M0535S). Amplification was followed in real time using Agilent's MX300P or Biorad's CFX Connect. Individual samples were removed immediately before the plateau in amplification to minimize distortion of template abundance due to over-amplification. Individual templates were purified with columns according to the manufacturer's instructions (Zymo DNA Clean and Concentrator; D4003) and eluted in RNase-free deionized water.

Amplification via in-vitro transcription. The template was then amplified via in vitro transcription. Briefly, 0.5 to 1 microgram of template DNA was amplified into 100-200 microgram of RNA in a single 20-30 microliter reaction with a high yield RNA polymerase (New England Biolabs; E2040S). Reactions were supplemented with 1× RNase inhibitor (Promega RNasin; N2611). Amplification was typically run for 4 to 16 hours at 37° C. to maximize the yield. The RNA was not purified after the reaction and was either stored at −80° C. or immediately converted into DNA as described below.

Reverse Transcription. 1 to 2 nmol of fluorescently-labeled ssDNA probe was created from the above in vitro transcription reactions using the reverse transcriptase Maxima H- (Thermo Scientific; EP0751). This enzyme was used because of its higher processivity and temperature resistance, which allowed the conversion of large quantities of RNA into DNA within small volumes at temperatures that disfavor secondary structure formation. The unpurified RNA created above was supplemented with 1.6 mM of each dNTP, 1-2 nmol of fluorescently labeled forward primer, 300 units of Maxima H-, 60 units of RNasin, and a final 1× concentration of the Maxima RT buffer. The final 75 microliter volume was incubated at 50° C. for 60 minutes.

Strand Selection and Purification. The template RNA in the reaction above was then removed from the DNA via alkaline hydrolysis. 75 microliters of 0.25 M EDTA and 0.5 N NaOH were added to each reverse transcription reaction, and the sample was incubated at 95° C. for 10 minutes. The reaction was immediately neutralized by purifying the ssDNA probe with a modified version of the Zymo Oligo Clean and Concentrator protocol. Specifically, the 5-microgram capacity column was replaced with a 25-microgram or 100-microgram capacity DNA column as appropriate. The remainder of the protocol was run according to the manufacturer's instructions. Probe was eluted in 100 microliter RNase-free deionized water and evaporated in a vacuum concentrator. The final pellet was resuspended in 10 microliters of RNase-free water and stored at −20° C. Denaturing poly-acrylamide gel electrophoresis and absorption spectroscopy revealed that this protocol typically produced 90-100% incorporation of the fluorescent primer into full length probe and 75-90% recovery of the total fluorescent probe. Thus, without exceeding a 150-microliter reaction volume, this protocol can be used to create ~2 nmol of fluorescent probe.

Cell culture and fixation. A549 and IMR90 cells (American Type Culture Collection) were cultured with Dulbecco's Modified Eagle Medium and Eagle's Minimum Essential Medium respectively. Cells were incubated at 37° C. with 5% $CO_2$ for 36-48 hours. Cells were fixed in 3% paraformaldehyde (Electron Microscopy Sciences) in PBS for 15 minutes, washed with PBS, and permeabilized in 70% ethanol overnight at 4° C.

Fluorescence In Situ Hybridization (FISH)—primary (encoding) probes. Cells were hydrated in wash buffers (2×SSC, 50% formamide) for 10 minutes, labelled with primary oligos (0.5 nM per sequence) in hybridization buffers (2×SSC, 50% formamide, 1 mg/mL yeast tRNA, and 10% dextran sulfate) overnight at 37° C., washed with wash buffers at 47° C. for 10 minutes twice, and washed with 2×SSC twice. Fluorescent fiducial beads (Molecular Probes, F-8809) were added at a 1:10,000 dilution in 2×SSC before imaging.

Secondary probes. Secondary (readout) probes (10 nM) were hybridized in secondary hybridization buffers (2×SSC, 20% formamide, and 10% dextran sulfate) to their primary targets for 30 minutes at 37° C. Cells remained on the microscope stage during the hybridization. An objective heater was used to maintain the temperature at 37° C. Cells were washed with secondary wash buffers (2×SSC, 20% formamide).

Fluidics and STORM Imaging. Multiple rounds of sequential labeling, washing, imaging, and bleaching were performed on an automated platform consisted of a fluidics setup and a STORM (stochastic optical reconstruction microscopy) microscope. The fluidics setup included a flow chamber (Bioptech FCS2), a peristaltic pump (Rainin Dynamax RP-1), and three computer-controlled 8-way valves (Hamilton MVP and Hamilton HVXM 8-5). This system allowed the automated integration of STORM movie collection and secondary hybridization.

The imaging buffer included, 50 mM Tris (pH 8) 10% (w/v) glucose, 1% PME (2-mercaptoethanol) or 25 mM MEA, with or without 2 mM 1,5-cyclooctadiene, and an oxygen scavenging system (0.5 mg/ml glucose oxidase (Sigma-Aldrich) and 40 microgram/ml catalase (Sigma-Aldrich)). A layer of mineral oil was used to seal the imaging buffer, preventing its acidification over the course of multiple hybridizations.

The STORM setup included an Olympus IX-71 inverted microscope configured for oblique incidence excitation. The samples were continuously illuminated with a 642-nm diode-pumped solid-state laser (VFL-P500-642; MPB communications). A 405-nm solid-state laser (Cube 405-100C; Coherent) was used for activation of dyes. Fluorescence was collected using an Olympus (UPlanSApo 100×, 1.4 NA) objective lens and passed through a custom dichroic, as well as a quad-view beam splitter. All movies were recorded using an EMCCD camera (Andor iAxon 897), imaging at 60 Hz. The 512×256 field of view of the camera was split into separate 256×256 pixel movies prior to saving. The left half of this field of view contained the STORM data and the right half contained images of the fluorescent feducial beads. These latter movies were downsampled to 1 Hz prior to saving. During data acquisition, a home-built focus lock was used to maintain a constant focal plane. STORM movies included 20,000 to 30,000 frames in STORM buffer while the bleach movies included 10,000 frames in wash buffer.

Image Analysis—analysis of single-molecule localizations. Movies of single molecule localizations and fluorescent feducial beads were processed separately using a previously published single-emitter localization software.

Image Registration. The starting position of the beads from each round of hybridization were used to align movies from each round. The 2D autocorrelation between bead images of consecutive hybridizations followed by nearest-neighbor matching was used to match beads between images. The pair of beads with the most similar displacement vector were used to compute a rigid translation-rotation warp to align the beads. This alignment method is robust to samples in which multiple feducials are displaced or come detached and reattach during imaging.

Drift Correction. Drift during image acquisition was corrected using the trajectory of the feducial beads (recorded at 1 Hz). Bead positions were linked in each frame. The trajectory of the two beads that moved in the most correlated fashion was taken as the drift trajectory.

mRNA Cluster Calling. Localizations were first screened to be above a threshold number of photons (generally 2000) and required to be within 32 nm of 5 other localizations (parameters may be tuned). The remaining molecule localizations were binned in a 2D histogram of 10×10 nm bins (bin size is a variable parameter). All connected bins were taken to be part of a cluster (diagonal contacts are classified as connected). Clusters were required to have more than 80 total localizations across all hybridizations (variable parameter) to be called an mRNA cluster. The weighted centroids of these clusters from the 2D histogram were recorded as the mRNA positions.

A given cluster is recorded to be represented in an individual hybridization round if more than 9 localizations (variable parameter) are found within a 48 nm radius (variable parameter) of the centroid for that mRNA in each hybridization round.

Cluster Decoding. For each mRNA cluster, a codeword is readout, including "0"s for all the hybridization rounds in which less than the threshold number of localizations are found near the centroid and "1" s for the rounds where above threshold number of localizations are counted. The SECDED codebook decoded these as either perfect matches to target mRNA codewords, correctable errors which can be unambiguously mapped back to target mRNA, or uncorrectable errors, which differed by two or more letters from the words in the codebook.

Figure 2A:
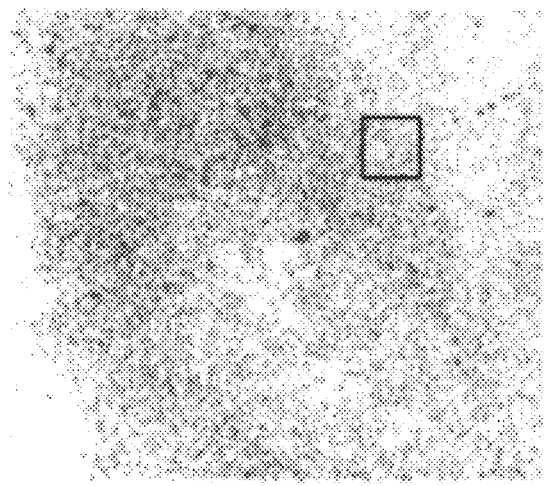
FIGS. 2A-2G illustrates determining of mRNAs in a cell, in some embodiments of the invention.
Figure 2B:
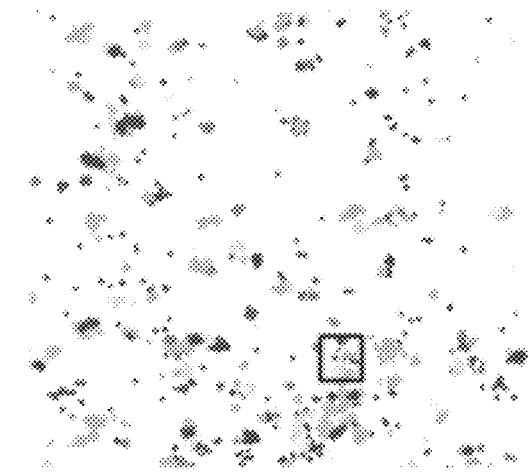
Figure 2C:
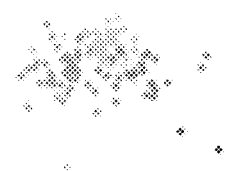
Figure 2D:
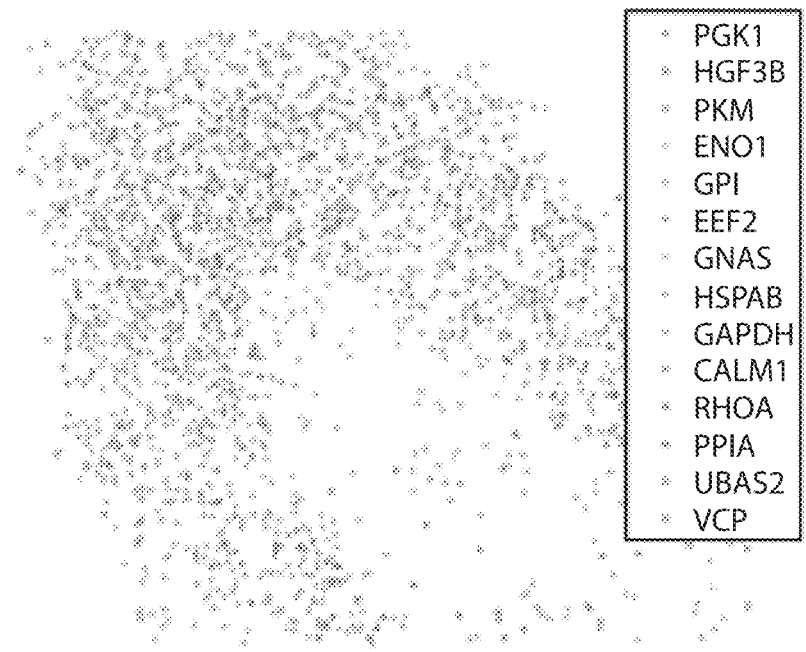
Figure 2E:
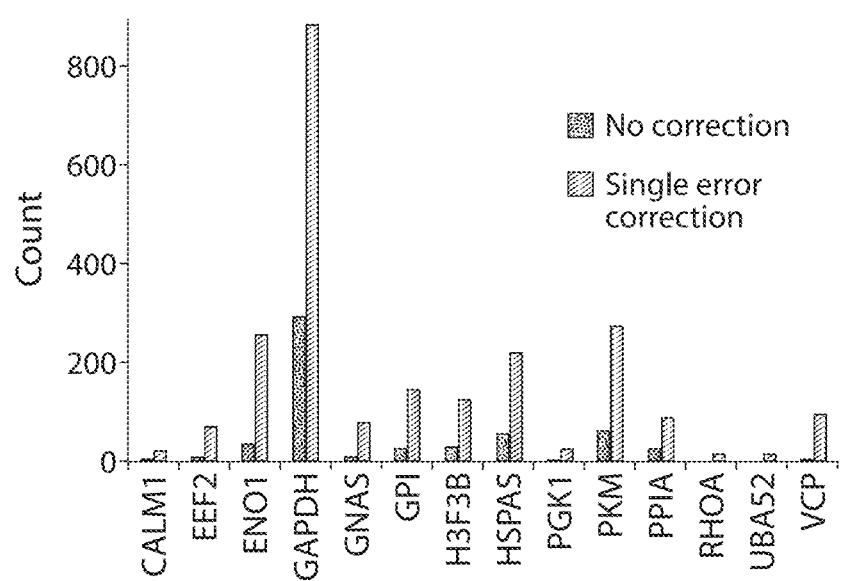
Figure 2F:
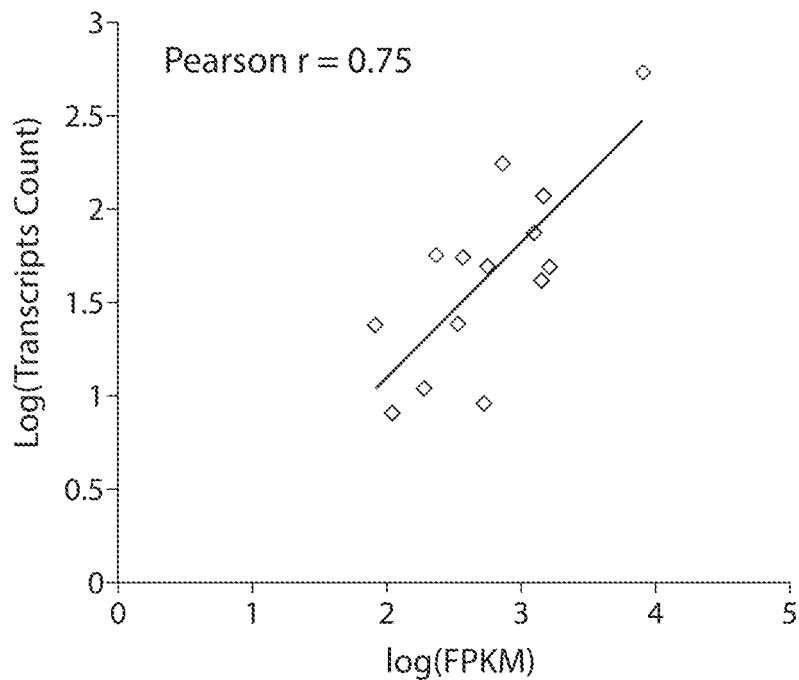
Figure 2G:
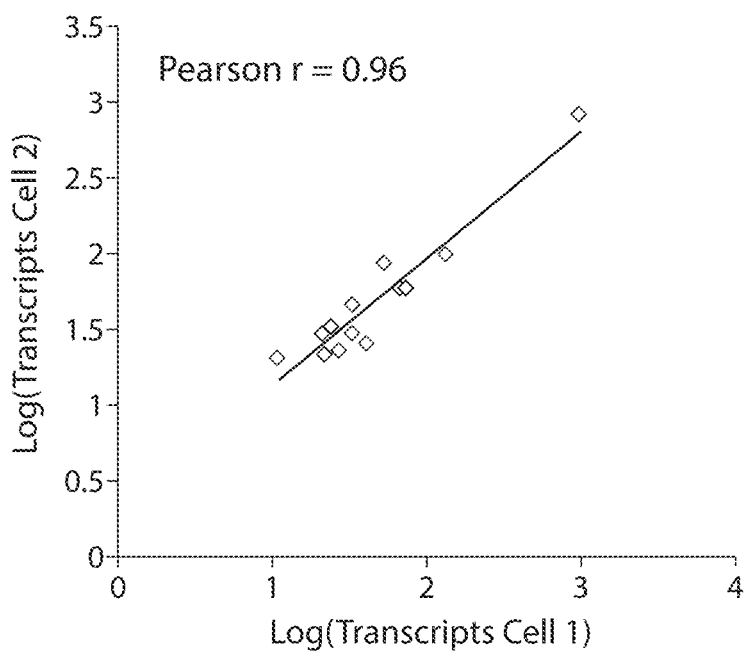

FIG. 2A shows a STORM image of a cell. FIG. 2B shows a zoom in of the boxed region in FIG. 2A. Each dot indicates a localization. Localizations from different rounds of imaging are shown differently. FIG. 2C shows a representative cluster of localizations from the boxed region in FIG. 2B. The cluster shows localization signals from 4 different hybridizations. This cluster is a putative mRNA encoded with codeword [0 1 0 1 1 1 0 0]. FIG. 2D shows a reconstructed cell image of 14 genes after decoding and error correction. Each gene is shown differently. FIG. 2E shows measured gene expression for the 14 genes from the cell. FIG. 2F shows a comparison of transcript count with ensemble RNA-sequencing data. FIG. 2G shows correlation of transcript expression level between two cells detected using the described approach.

Example 4

The following examples are generally directed to multiplexed single-molecule imaging with error-robust encoding allowing for simultaneous measurements of thousands of RNA species in single cells. In general, knowledge of the expression profile and spatial landscape of RNAs in individual cells is essential for understanding the rich repertoire of cellular behaviors. The following examples reports various techniques directed to single-molecule imaging approaches that allow the copy numbers and spatial localizations of thousands of RNA species to be determined in single cells. Some of these techniques are called Multiplexed Error-Robust Fluorescence in Situ Hybridization or "MERFISH."

Using error-robust encoding schemes to combat single-molecule labeling and detection errors, these examples demonstrated the imaging of hundreds to thousands of unique RNA species in hundreds of individual cells. Correlation analysis of the ~$10^4$ to ~$10^6$ pairs of genes allowed constraints on gene regulatory networks, prediction of novel functions for many unannotated genes, and identification of distinct spatial distribution patterns of RNAs that correlate with properties of the encoded proteins.

System-wide analyses of the abundance and spatial organization of RNAs in single cells promise to transform understanding in many areas of cell and developmental biology, such as the mechanisms of gene regulation, the heterogeneous behavior of cells, and the development and maintenance of cell fate. Single-molecule fluorescence in situ hybridization (smFISH) has emerged as a powerful tool for studying the copy number and spatial organization of RNAs in single cells either in isolation or in their native tissue context. Taking advantage of its ability to map the spatial distributions of specific RNAs with high resolution, smFISH has revealed the importance of subcellular RNA localization in diverse processes such as cell migration, development, and polarization. In parallel, the ability of smFISH to precisely measure the copy numbers of specific RNAs without amplification bias has allowed quantitative measurement of the natural fluctuations in gene expression, which has in turn elucidated the regulatory mechanisms that shape such fluctuations and their role in a variety of biological processes.

However, application of the smFISH approach to many systems-level questions remains limited by the number of RNA species that can be simultaneously measured in single cells. State-of-the-art efforts using combinatorial labeling by either color-based barcodes or sequential hybridization have enabled simultaneous measurements of 10-30 different RNA species in individual cells, yet many interesting biological questions would benefit from the measurement of hundreds to thousands of RNAs within a single cell, which are not achievable using such techniques. For example, analysis of how the expression profile of such a large number of RNAs vary from cell to cell and how these variations correlate among different genes could be used to systematically identify co-regulated genes and map regulatory networks; knowledge of the subcellular organizations of numerous RNAs and their correlations could help elucidate molecular mechanisms underlying the establishment and maintenance of many local cellular structures; and RNA profiling of individual cells in native tissues could allow in situ identification of cell type.

The following examples generally discuss certain techniques called MERFISH, which are highly multiplexed smFISH imaging methods that substantially increase the number of RNA species that can be simultaneously imaged in single cells by using combinatorial labeling and sequential imaging with error-robust encoding schemes. These examples demonstrate this multiplexed imaging approach by simultaneously measuring 140 RNA species using an encoding scheme that can both detect and correct errors and 1001 RNA species using an encoding scheme that can detect but not correct errors. It should be understood that these numbers are by way of exemplification only, not limitation. Correlation analyses of the copy number variations and spatial distributions of these genes allowed us to identify groups of genes that are co-regulated and groups of genes that share similar spatial distribution patterns inside the cell.

Figure 5A:
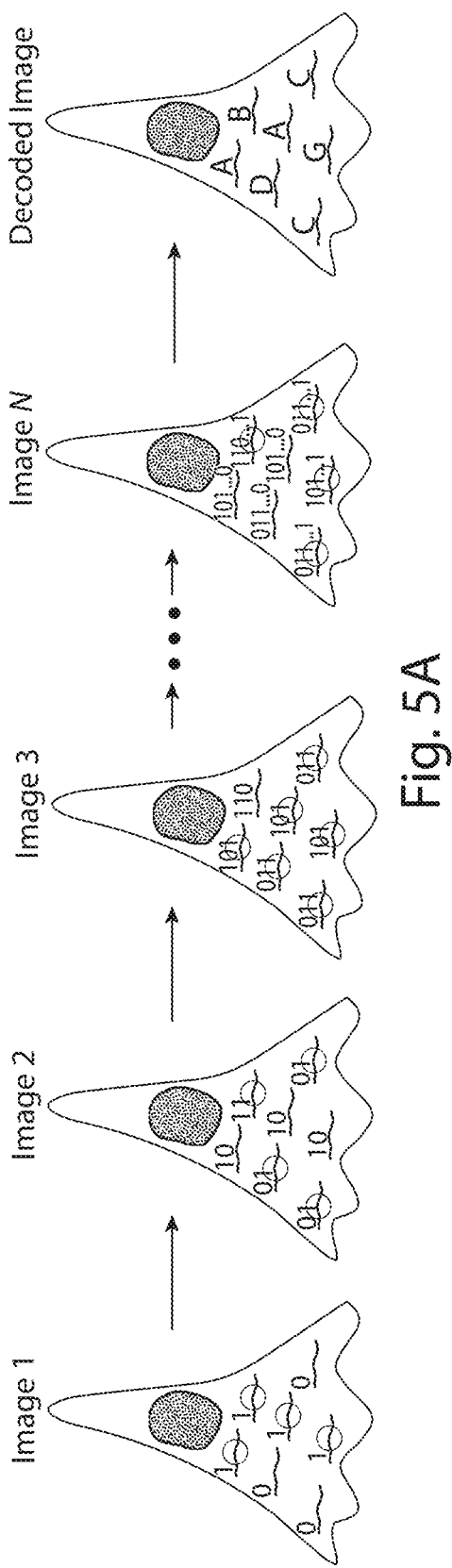
FIGS. 5A-5E illustrate the determination of nucleic acids, in accordance with another embodiment of the invention.
Figure 5B:
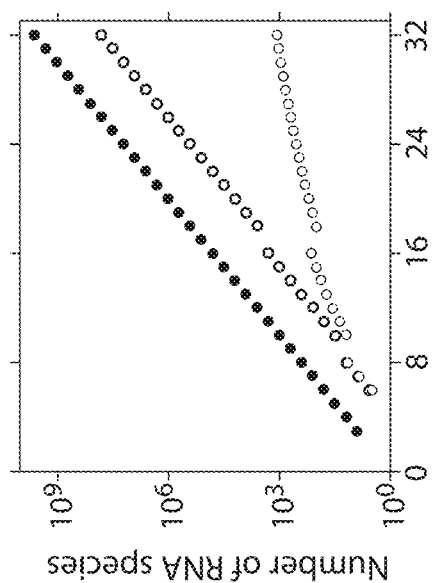
Figure 5D:
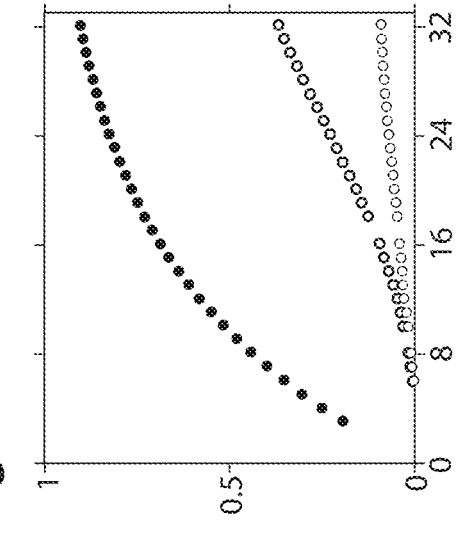
Figure 5C:
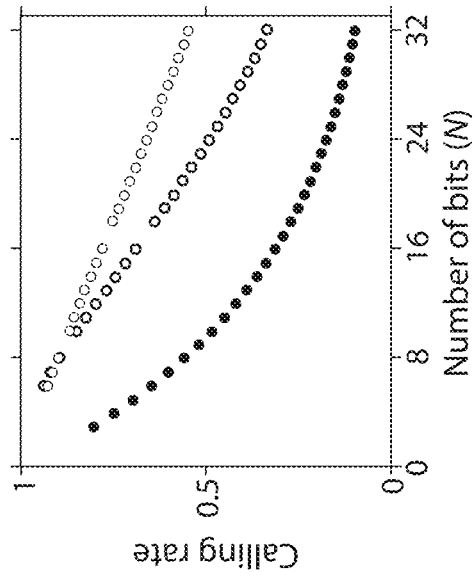
Figure 11:
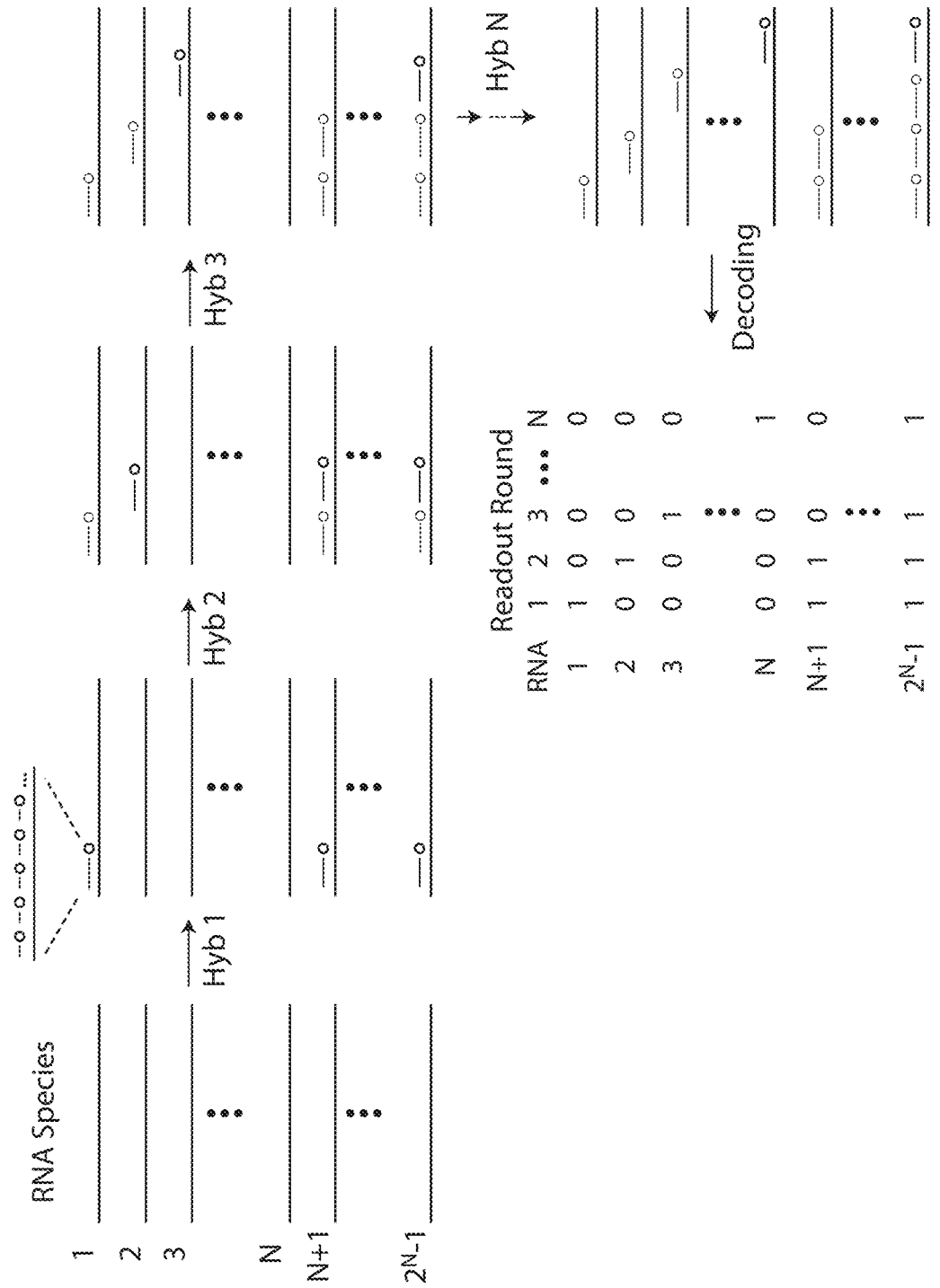
FIG. 11 is a schematic description of combinatorial labeling, in accordance with another embodiment of the invention.

Combinatorial labeling with error-robust encoding schemes. Combinatorial labeling that identifies each RNA species by multiple (N) distinct signals offers a route to rapidly increase the number of RNA species that can be probed simultaneously in individual cells (FIG. 5A). However, this approach to scaling up the throughput of smFISH to the systems scale faces a significant challenge because not only does the number of addressable RNA species increases exponentially with N, but the detection error rates also grow exponentially with N (FIGS. 5B-5D). Imagine a conceptually simple scheme to implement combinatorial labeling, where each RNA species is encoded with a N-bit binary word and the sample is probed with N corresponding rounds of hybridization, each round targeting only the subset of RNAs that should read '1' in the corresponding bit (FIG. 11). N rounds of hybridization would allow $2^N-1$ RNA species to be probed. With just 16 hybridizations, over 64,000 RNA species, which should cover the entire human transcriptome including both messenger RNAs (mRNAs) and non-coding RNAs, could be identified (FIG. 5B; upper symbols). However, as N increases, the fraction of RNAs properly detected (the calling rate) would rapidly decrease and, more troublingly, the fraction of RNAs that are identified as incorrect species (the misidentification rate) would rapidly increase (FIG. 5C, lower symbols; FIG. 5D, upper symbols). With realistic error rates per hybridization (measured below), the majority of RNA molecules would be misidentified after 16 rounds of hybridizations!

To address this challenge, error-robust encoding schemes were designed, in which only a subset of the $2^N-1$ words separated by a certain Hamming distance were used to encode RNAs. In a codebook where the minimum Hamming distance is 4 (HD4 code), at least four bits must be read incorrectly to change one code word into another (FIG. 12A). As a result, every single-bit error produces a word that is uniquely close to a single code word, allowing such errors to be detected and corrected (FIG. 12B). Double-bit errors produce words with an equal Hamming distance of 2 from multiple code words and, thus, can be detected but not corrected (FIG. 12C). Such a code should substantially increase the calling rate and reduce the misidentification rate (FIGS. 5C and 5D, middle symbols). To further account for the fact that it is more likely to miss a hybridization event (an 1→0 error) than to misidentify a background spot as an RNA (an 0→1 error) in smFISH measurements, a modified HD4 (MHD4) code was designed, in which the number of '1' bits were kept both constant and relatively low, only four per word, to reduce error and avoid biased detection. This MHD4 code should further increase the calling rate and reduce the misidentification rate (FIG. 5C, upper symbols; FIG. 5D, lower symbols).

Figure 5E:
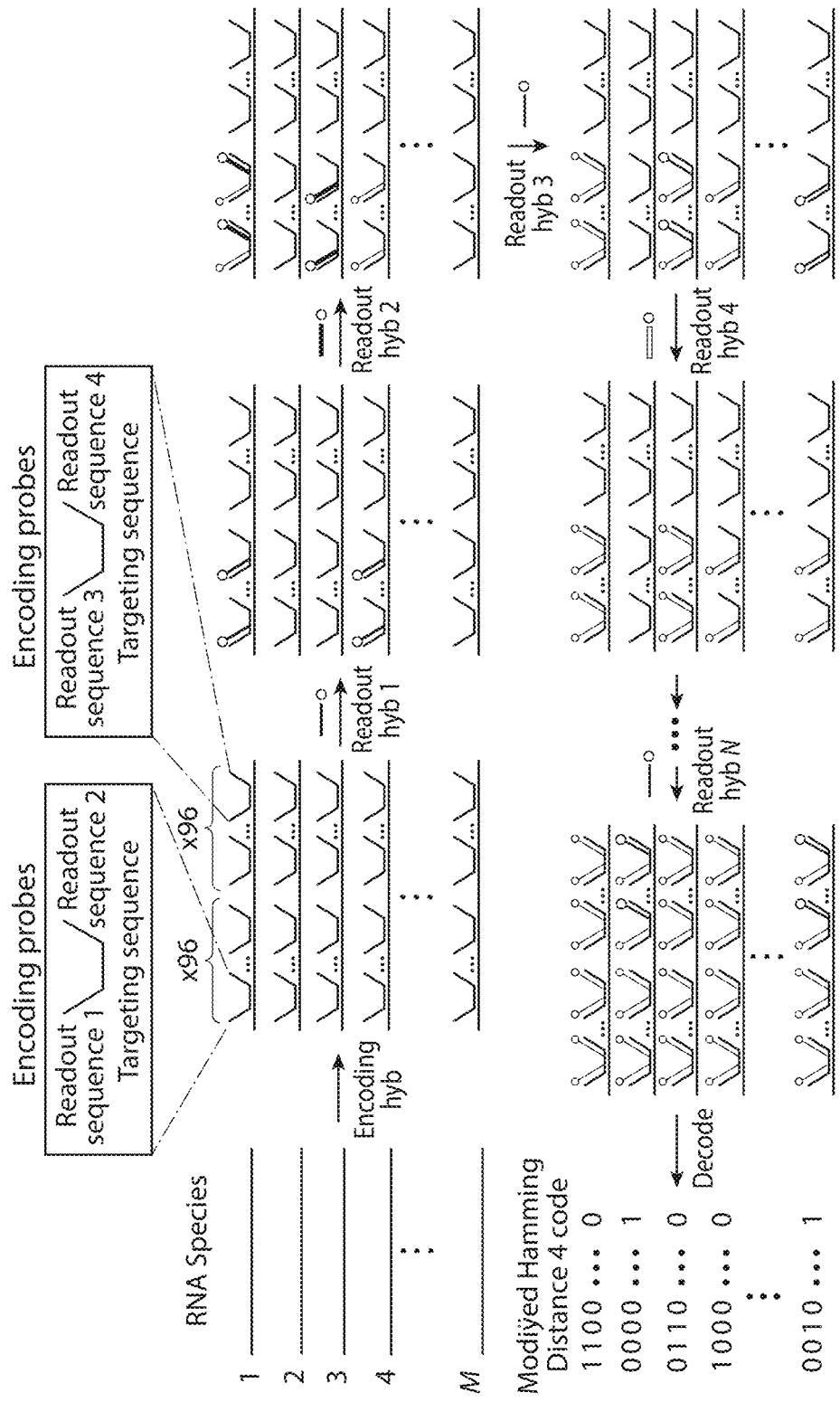
Figure 13:
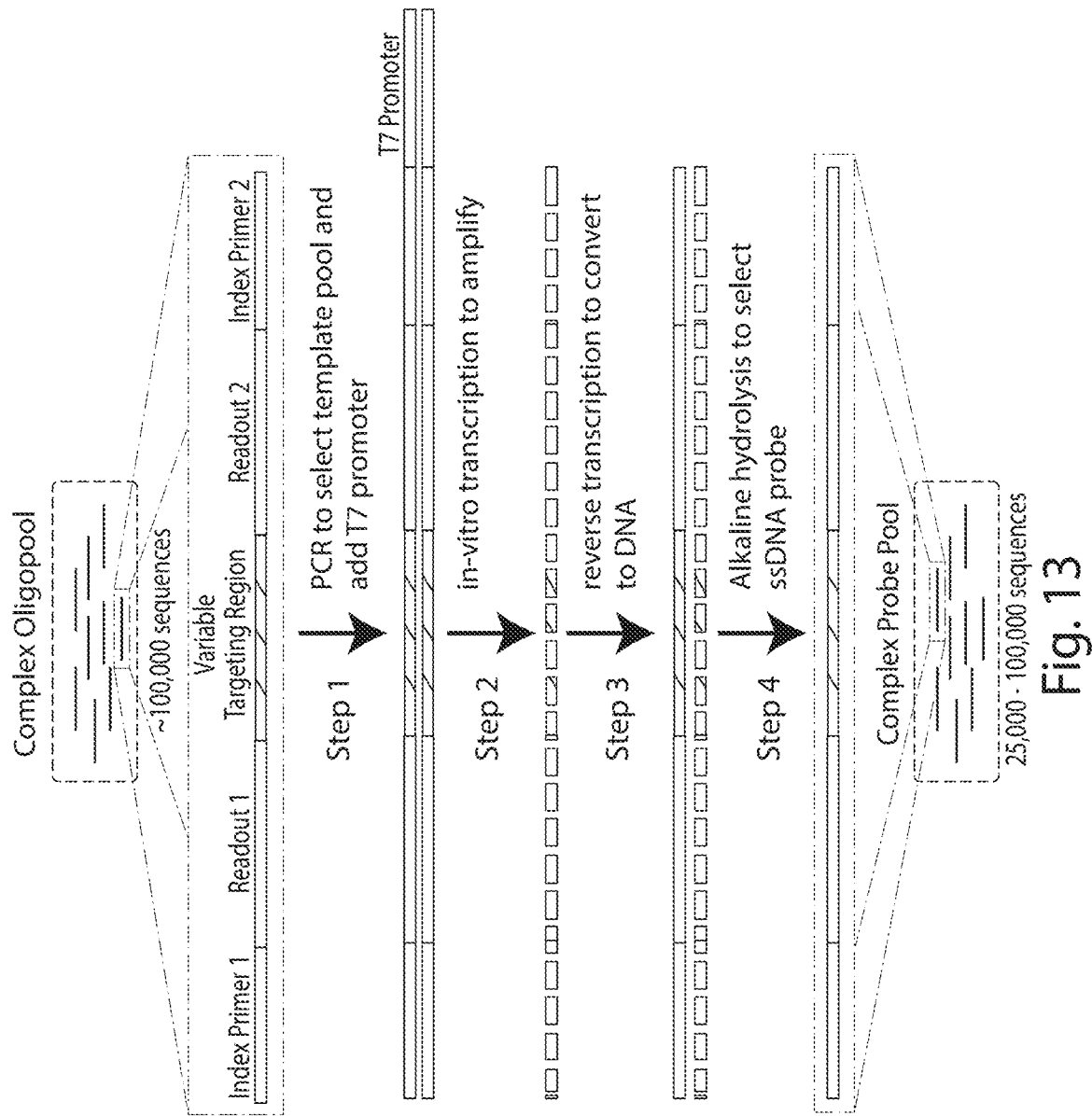
FIG. 13 illustrates the production of a library of probes, in still another embodiment of the invention.

In addition to the error considerations, several practical challenges have also made it difficult to probe a large number of RNA species, such as the high cost of the massive number of fluorescently labeled FISH probes needed and the long time required to complete many rounds of hybridization. To overcome these challenges, in this example, a two-step labeling scheme was designed to encode and readout cellular RNAs (FIG. 5E). First, cellular RNAs were labeled with a set of encoding probes (also called primary probes), each probe comprising a RNA targeting sequence and two flanking readout sequences. Four of the N unique readout sequences were assigned to each RNA species based on the MHD4 code word of the RNA. Second, these N readout sequences were identified with complementary FISH probes, the readout probes (also called secondary probes) via N rounds of hybridization and imaging, each round using a unique readout probe. To increase the signal to background ratio, every cellular RNA was labeled with ~192 encoding probes. Because each encoding probe contained two of the four readout sequences associated with that RNA (FIG. 5E), a maximum of ~96 readout probes can bind to each cellular RNA per hybridization round. To generate the massive number of encoding probes required, they were amplified from array-derived oligonucleotide pools containing tens of thousands of custom sequences using an enzymatic amplification process comprising in vitro transcription followed by reverse transcription (FIG. 13, see below regarding probe synthesis). This two-step labeling approach significantly diminished the total hybridization time for an experiment: it was found that efficient hybridization to the readout sequences took only 15 minutes whereas efficient direct hybridization to cellular RNA required more than 10 hours.

FIGS. 5A-5E describe MERFISH, a highly multiplexed smFISH approach using combinatorial labeling and error-robust encoding. FIG. 5A shows a schematic depiction of the identification of multiple RNA species in N rounds of imaging. Each RNA species is encoded with a N-bit binary word and during each round of imaging, only the subset of RNAs that should read '1' in the corresponding bit emit signal. FIGS. 5B-5D show the number of addressable RNA species (FIG. 5B), the rate at which these RNAs are properly identified (calling rate) (FIG. 5C), and the rate at which RNAs are incorrectly identified as a different RNA species (misidentification rate) (FIG. 5D) plotted as a function of the number of bits (N) in the binary words encoding RNA. In FIGS. 5B and 5D, the upper dots are a simple binary code that includes all $2^N-1$ possible binary words; the middle dots are the HD4 code where the Hamming distance separating words is 4; and the lower dots are the modified HD4 (MHD4) code where the number of '1' bits are kept at four. These are reversed in FIG. 5C.

The calling and misidentification rates are calculated with per bit error rates of 10% for the 1→0 error and 4% for the 0→1 error. FIG. 5E is as schematic diagram of the implementation of a MHD4 code for RNA identification. Each RNA species is first labeled with ~192 encoding probes that convert the RNA into a unique combination of readout sequences (Encoding hyb). These encoding probes each contain a central RNA targeting region flanked by two readout sequences, drawn from a pool of N different sequences, each associated with a specific hybridization round. Encoding probes for a specific RNA species contain a unique combination of four of the N readout sequences, which correspond to the four hybridization rounds where this RNA should read '1'. N subsequent rounds of hybridization with the fluorescent readout probes were used to probe the readout sequences (hyb 1, hyb 2, . . . , hyb N). The bound probes were inactivated by photobleaching between successive rounds of hybridization. For clarity, only one possible pairing of the readout sequences is depicted here for the encoding probes; however, all possible pairs of the four readout sequences are used at the same frequency and distributed randomly along each cellular RNA in the actual experiments.

FIG. 11 shows a schematic description of a combinatorial labeling approach based on a simple binary code. In a conceptually simple labeling approach, $2^N-1$ different RNA species can be uniquely encoded with all N-bit binary words (excluding the word with all '0's). In each hybridization round, FISH probes that are targeted to all RNA species that have a '1' in the corresponding bit are included. To increase the ability to discriminate RNA spots from background, each RNA is addressed with multiple FISH probes per hybridization round. Signal from the bound probes is extinguished before the next round of hybridization. This process continues for all N hybridization rounds (hyb 1, hyb 2, . . . ), and all $2^N-1$ RNA species can be identified by the unique on-off pattern of fluorescence signals in each hybridization round.

FIGS. 12A-12C show schematic descriptions of Hamming distance and its use in the identification and correction of errors. FIG. 12A is a schematic representation of a Hamming distance of 4. FIGS. 12B and 12C are schematics showing the ability of an encoding scheme with Hamming distance 4 to correct single-bit errors (FIG. 12B) or detect but not correct double-bit errors (FIG. 12C). Arrows highlight bits at which the indicated words differ. Two code words are separated by a Hamming distance of 4 if one of the words has to flip four bits from '1' to '0' or '0' to '1' to convert into the other word. Single-bit error correction is possible because if a measured word differs from a legitimate code word by only one bit, it is most likely an error that arises from misreading this code word, since the code words of all the other RNA species will differ from the measured word by at least three bits. In this case, the measured word can be corrected to a code word that differs by only one bit. If a measured word differs from a legitimate code word by two bits, this measured word can still be identified as an error, but correction is no longer possible since more than one legitimate code word differs from this measured word by two bits.

FIG. 13 shows production of the library of encoding probes. An array-synthesized complex oligopool, containing ~100 k sequences, is used as a template for the enzymatic amplification of the encoding probes for different experiments. Each template sequence in the oligopool contains a central target region that can bind to a cellular RNA, two flanking readout sequences, and two flanking index primers. In the first step, the required template molecules for a specific experiment are selected and amplified with an indexed PCR reaction. To allow amplification via in vitro transcription, a T7 promotor is added to the PCR products during this step. In the second step, RNA is amplified from these template molecules via in vitro transcription. In the third step, this RNA is reverse transcribed back into DNA. In the final step, the template RNA is removed via alkaline hydrolysis, leaving only the desired ssDNA probes. This protocol produces ~2 nmol of complex pools of encoding probes containing ~20,000 different sequences for the 140-gene experiments or ~100,000 different sequences for the 1001-gene experiments.

Example 5

Figure 6A:
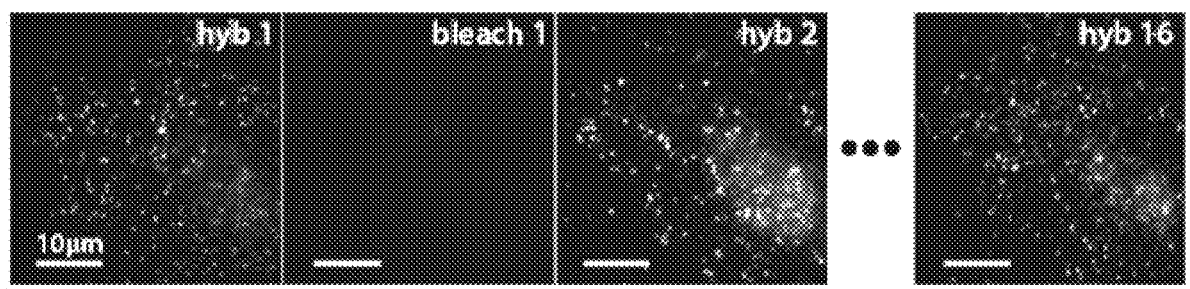
FIGS. 6A-6H illustrate simultaneous determination of multiple nucleic acid species in cells, in certain embodiments of the invention.
Figure 14A:
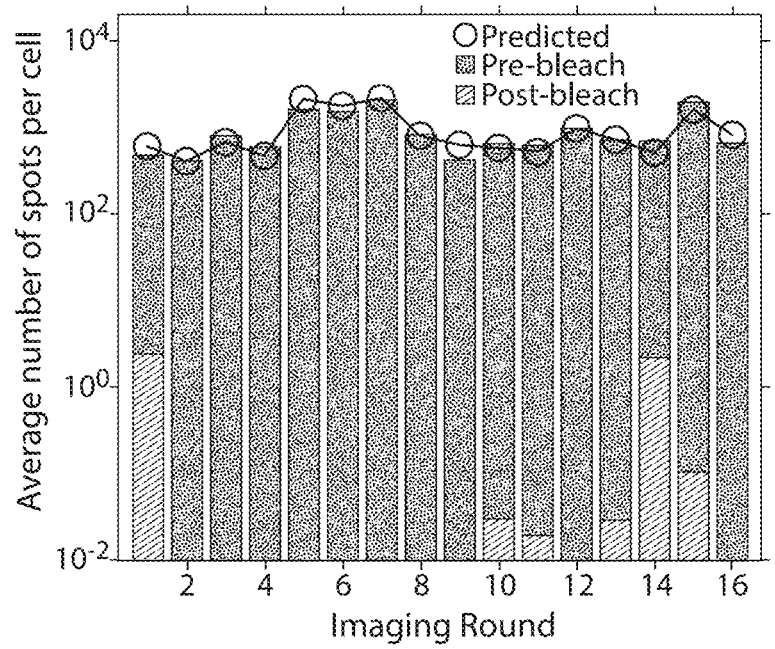
FIGS. 14A-14B illustrate fluorescent spot determinations, in another embodiment of the invention.
Figure 14B:
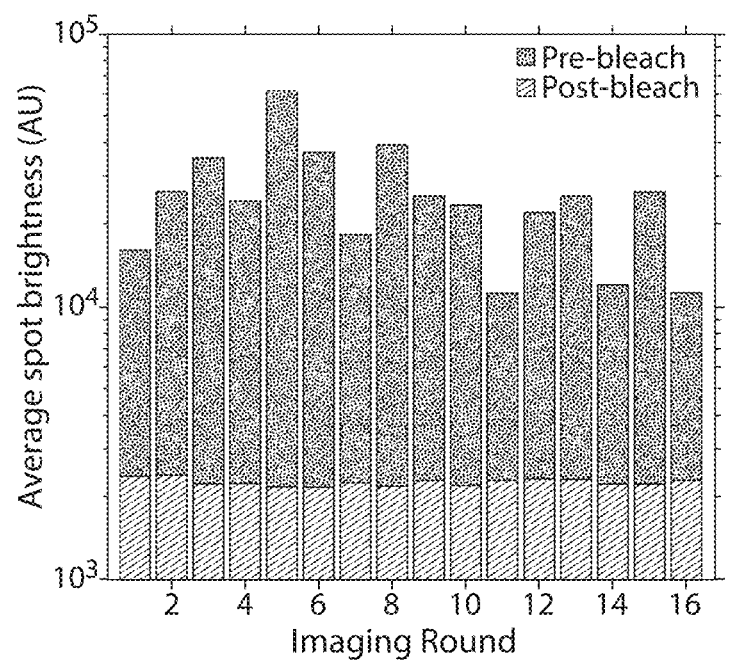

This example illustrates the measurement of 140 genes with MERFISH using a 16-bit MHD4 Code. To test the feasibility of this error-robust, multiplexed imaging approach, this example uses a 140-gene measurement on human fibroblast cells (IMR90) using a 16-bit MHD4 code to encode 130 RNA species while leaving 10 code words as misidentification controls (FIGS. 20A-20H). After each round of hybridization with the fluorescent readout probes, cells were imaged by conventional wide-field imaging with an oblique-incidence illumination geometry. Fluorescent spots corresponding to individual RNAs were clearly detected and were then efficiently extinguished via a brief photobleaching step (FIG. 6A). The sample was stable throughout the 16 rounds of iterative labeling and imaging. The change in the number of fluorescent spots from round to round matched the predicted change based on the relative abundances of RNA species targeted in each round derived from bulk sequencing, and a systematic decreasing trend with increasing number of hybridization rounds was not observed (FIG. 14A). The average brightness of the spots varied from round to round with a standard deviation of 40%, likely due to different binding efficiencies of the readout probes to the different readout sequences on the encoding probes (FIG. 14B). Only a small, systematic decreasing trend in the spot brightness with increasing hybridization rounds was observed, which was on average 4% per round (FIG. 14B).

Figure 6B:
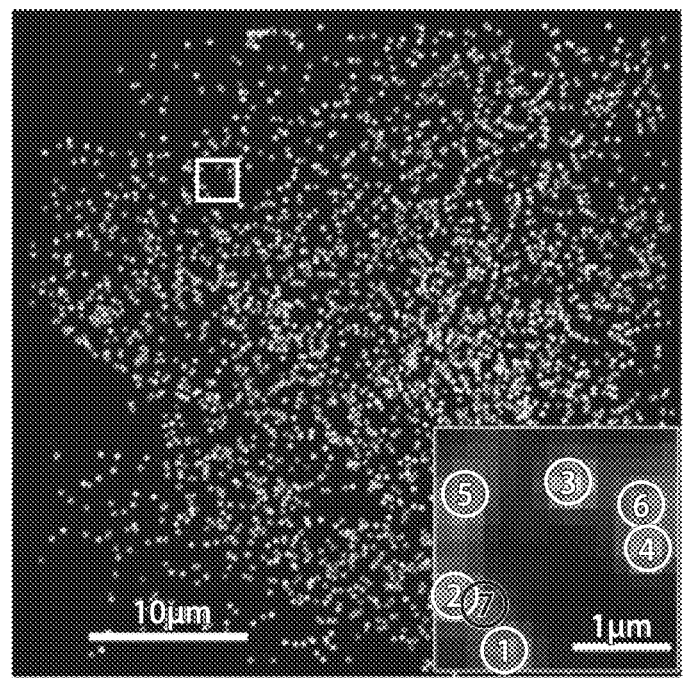
Figure 6C:
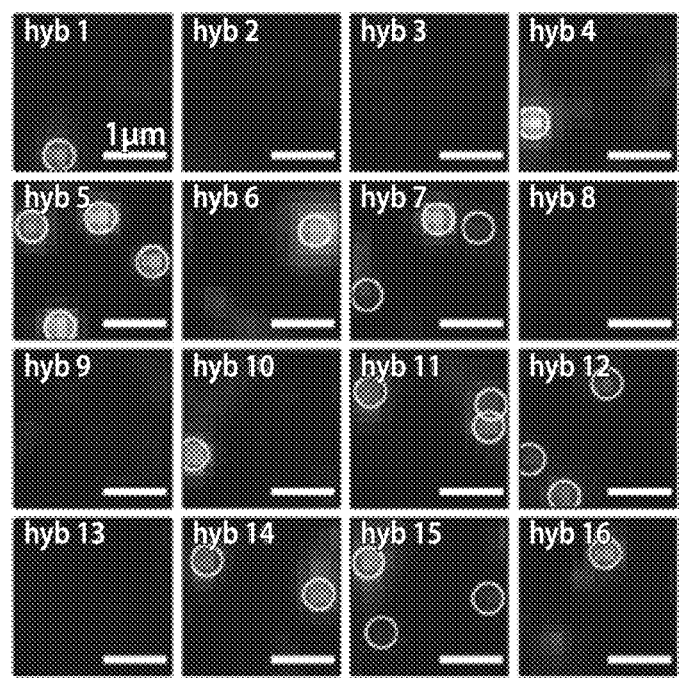
Figures 6D, 6E:
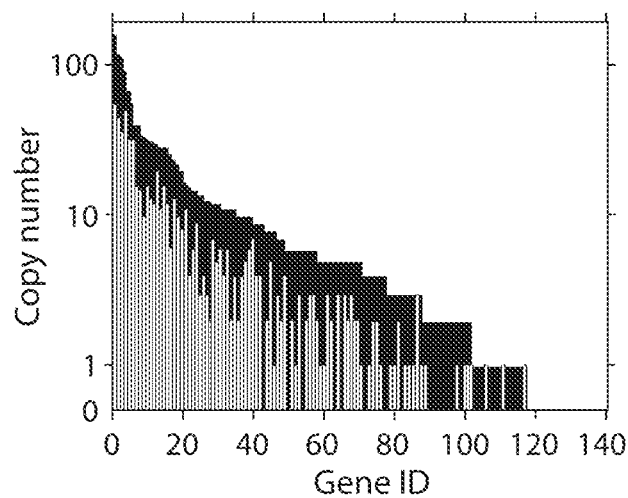
Figure 15A:
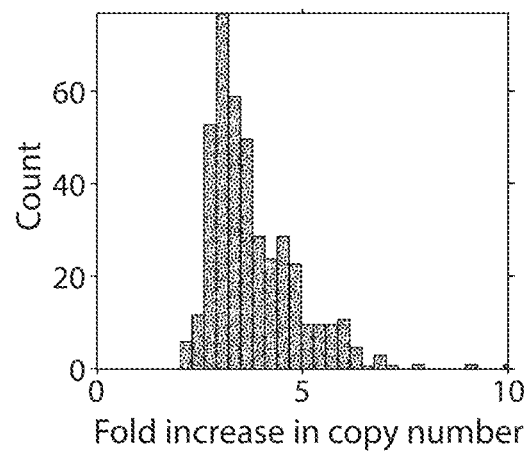
FIGS. 15A-15B illustrate error correction facilitates RNA detection, in yet another embodiment of the invention.
Figure 15B:
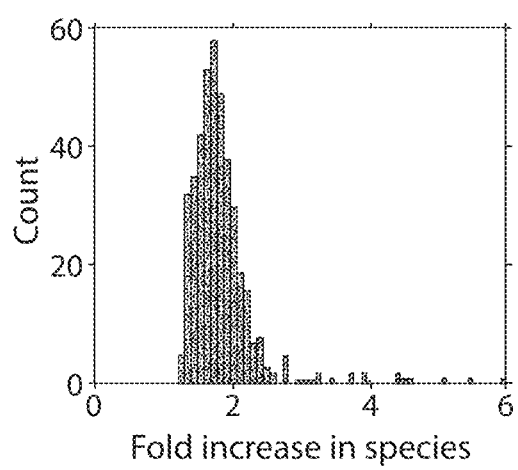

Next, binary words were constructed from the observed fluorescent spots based on their on-off patterns across the 16 hybridization rounds (FIG. 6B-6D). If the word exactly matched one of the 140 MHD4 code words (exact matches) or differed by only one bit (error-correctable matches), it was assigned to the corresponding RNA species (FIG. 6D). Within the single cell depicted in FIGS. 6A and 6B, more than 1500 RNA molecules corresponding to 87% of the 130 encoded RNA species were detected after error correction (FIG. 6E). Similar observations were made in ~400 cells from 7 independent experiments. On average, ~4 times as many RNA molecules and ~2 times as many RNA species were detected per cell after error correction as compared with the values obtained before error correction (FIGS. 15A-15B).

Figure 16A:
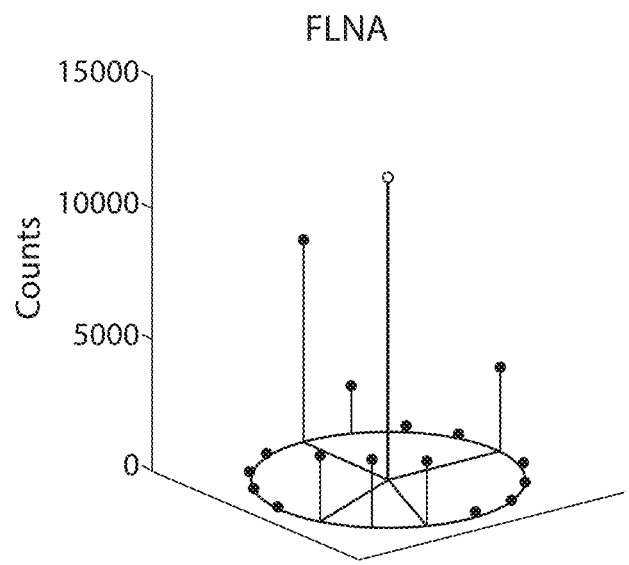
FIGS. 16A-16E show characterization of misidentification rates and calling rates, in one embodiment of the invention.
Figure 16B:
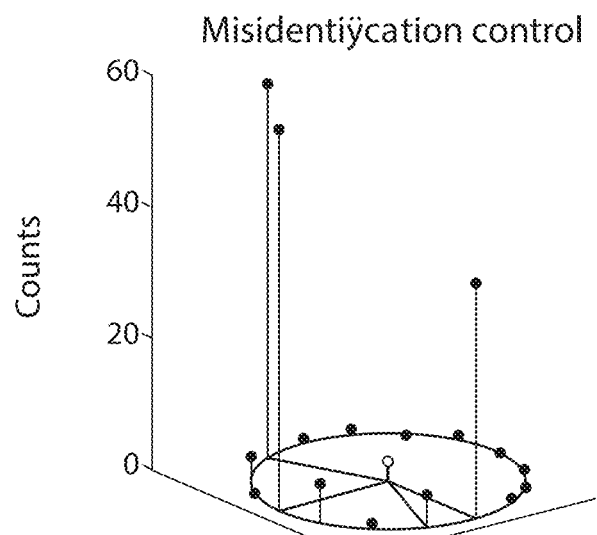

Two types of errors can occur in the copy number measurement of each RNA species: 1) Some molecules of this RNA species are not detected, leading to a drop in calling rate, and 2) some molecules from other RNA species are misidentified as this RNA species. To assess the extent of misidentification, the 10 misidentification control words were utilized, i.e., code words that were not associated with any cellular RNA. Although matches to these control words were observed, they occurred far less frequently than the real RNA-encoding words: 95% of the 130 RNA-encoding words were counted more frequently than the median count for these control words. Moreover, it was typically found that the ratio of the number of exact matches to the number of matches with one-bit errors for a real RNA-encoding word was substantially higher than the same ratios observed for the misidentification controls, as expected (FIGS. 16A and 16B). Using this ratio as a measure of the confidence in RNA identification, it was found that 91% of the 130 RNA species had a confidence ratio greater than the maximum confidence ratio observed for the misidentification controls (FIG. 6F), demonstrating a high accuracy of RNA identification. Subsequent analyses were conducted only on these 91% of genes.

Figure 16C:
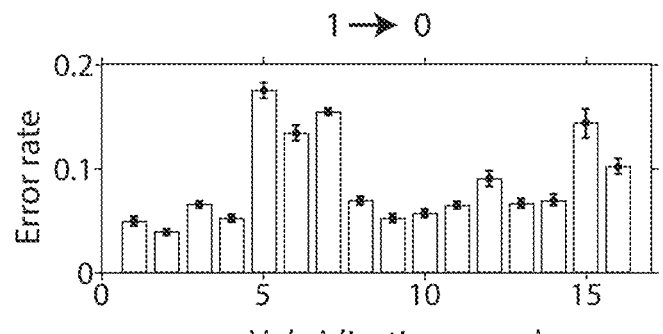
Figure 16D:
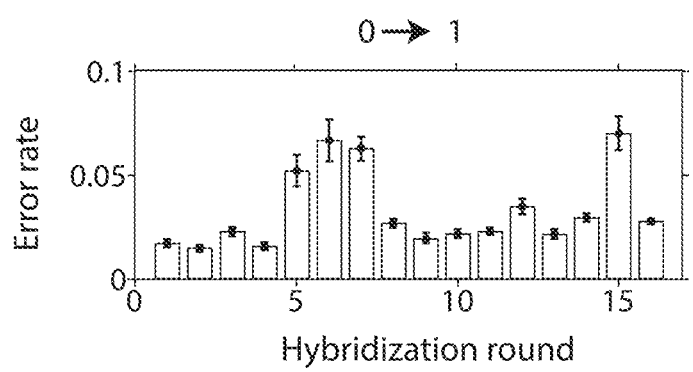
Figure 16E:
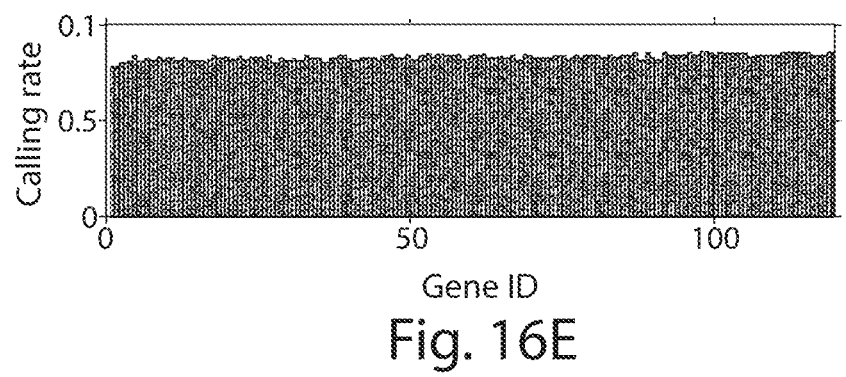

To estimate the calling rate, the error-correction ability of the MHD4 code was utilized to determine the 1→0 error rates (10% on average) and 0→1 error rates (4% on average) for each hybridization round (FIGS. 16C and 16D). Using these error rates, an ~80% calling rate for individual RNA species after error correction was estimated, i.e. ~80% of the fluorescent spots corresponding to a RNA species were decoded correctly (FIG. 16E). It is noted that although the remaining 20% of spots contributed to a loss in detection efficiency, most of them did not cause species misidentification because they were decoded as double-bit error words and discarded.

To test for potential technical bias in these measurements, the same 130 RNAs species were probed with a different MHD4 codebook by shuffling the code words among different RNA species (FIGS. 20A-20H) and changing the encoding probe sequences. Measurements with this alternative code gave similar misidentification and calling rates (FIGS. 17A-17D). The copy numbers of individual RNA species per cell measured with these two codebooks showed excellent agreement with a Pearson correlation coefficient of 0.94 (FIG. 6G), indicating that the choice of encoding scheme did not bias the measured counts.

Figure 18A:
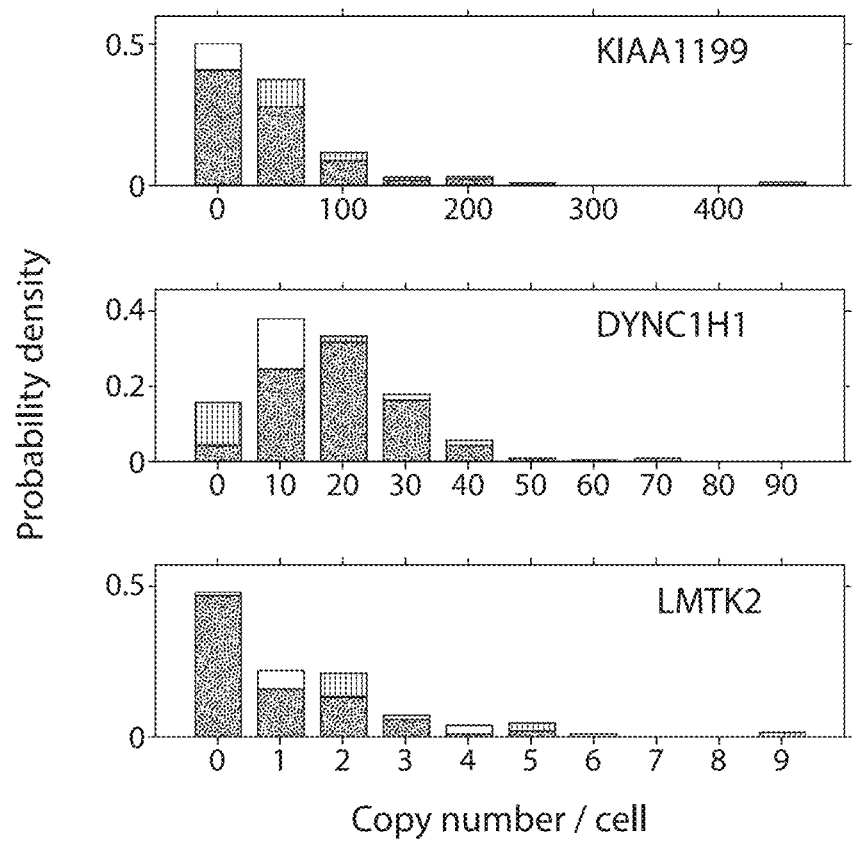
FIGS. 18A-18C show a comparison of experiments, in accordance with one embodiment of the invention.
Figure 18B:
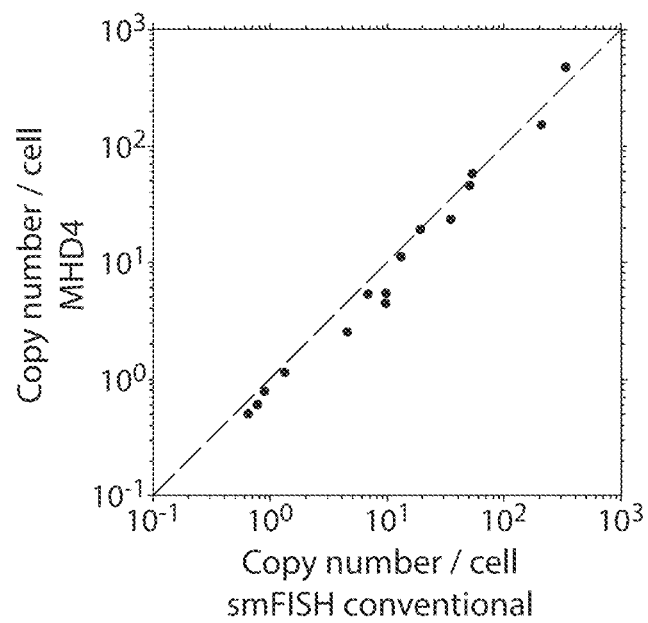

In order to validate the copy numbers derived from the MERFISH experiments, conventional smFISH measurements were performed on 15 of the 130 genes, selected from the full measured abundance range of three orders of magnitude. For each of these genes, both the average copy number and the copy number distribution across many cells agreed quantitatively between the MERFISH and conventional smFISH measurements (FIGS. 18A and 18B). The ratio of the copy numbers determined by these two approaches was 0.82+/−0.06 (mean+/−SEM across the 15 measured RNA species, FIG. 18B), which agreed with the estimated 80% calling rate for the multiplexed imaging approach. The quantitative match between this ratio and the estimated calling rate over the full measured abundance range additionally supports the assessment that the misidentification error was low. Given that the agreement between the MERFISH and conventional smFISH results extended to the genes at the lowest measured abundance (<1 copy per cell, FIG. 18B), it was estimated that the measurement sensitivity was at least 1 copy per cell.

As a final validation, the abundance of each RNA species averaged over hundreds of cells was compared to those obtained from a bulk RNA sequencing measurement that were performed on the same cell line. The imaging results correlated remarkably well with bulk sequencing results with a Pearson correlation coefficient of 0.89 (FIG. 6H).

Figure 6F:
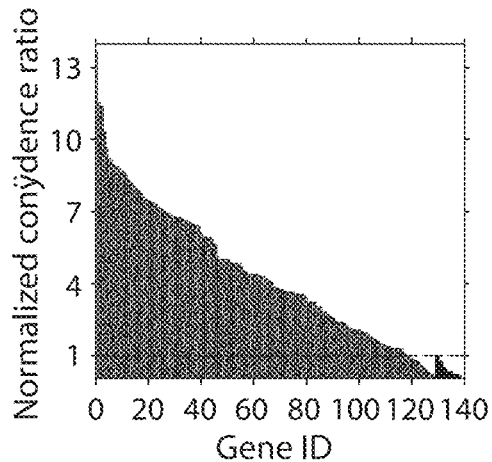
Figure 6G:
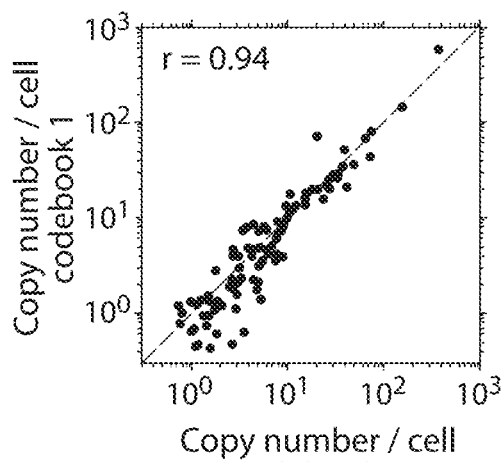
Figure 6H:
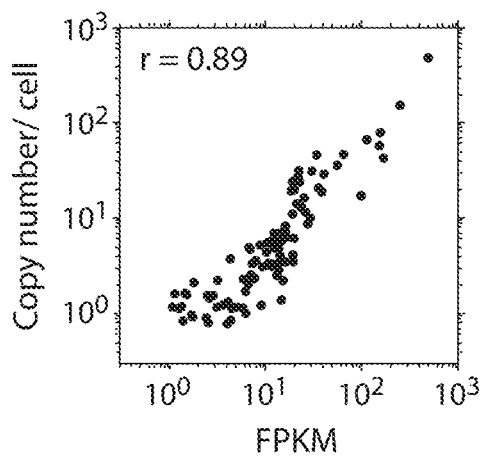

FIGS. 6A-6H show simultaneous measurement of 140 RNA species in single cells using MERFISH with a 16-bit MHD4 code. FIG. 6A shows images of RNA molecules in an IMR90 cell after each hybridization round (hyb 1-hyb 16). The image after photobleaching (bleach 1) demonstrated efficient removal of fluorescent signals between hybridizations. FIG. 6B shows the localizations of all detected single molecules in this cell colored based on their measured binary words. Inset: the composite fluorescent image of the 16 hybridization rounds for the boxed sub-region with numbered circles indicating potential RNA molecules. A circle indicates an unidentifiable molecule, the binary word of which does not match any of the 16-bit MHD4 code words even after error correction. FIG. 6C shows fluorescent images from each round of hybridization for the boxed sub-region in FIG. 6B with circles indicating potential RNA molecules. FIG. 6D shows corresponding words for the spots identified in FIG. 6C. Crosses represent the corrected bits. FIG. 6E shows the RNA copy number for each gene observed without (lower) or with (higher) error correction in this cell. FIG. 6F shows the confidence ratio measured for the 130 RNA species (left) and the 10 misidentification control words (right) normalized to the maximum value observed from the misidentification controls (dashed line). FIG. 6G is a scatter plot of the average copy number of each RNA species per cell measured with two shuffled codebooks of the MHD4 code. The Pearson correlation coefficient is 0.94 with a p-value of $1 \times 10^{-53}$. The dashed line corresponds to the y=x line. FIG. 6H is a scatter plot of the average copy number of each RNA species per cell versus the abundance determined by bulk sequencing in fragments per kilobase per million reads (FPKM). The Pearson correlation coefficient between the logarithmic abundances of the two measurements was 0.89 with a p-value of $3 \times 10^{-39}$.

FIGS. 14A-14B show the number and average brightness of the fluorescent spots detected in the 16 rounds of hybridization before and after photobleaching. FIG. 14A shows the number of fluorescent spots observed per cell before (higher) and after (lower) photobleaching as a function of hybridization round averaged across all measurements with the first 16-bit MHD4 code. Photobleaching reduces the number of fluorescent spots by two or more orders of magnitude. Hybridization rounds without lower bars represent rounds in which no molecules were observed after bleaching. Also depicted is the expected change in the number of fluorescent spots from round to round (circles) predicted based on the relative abundances of the RNA species targeted in each hybridization round derived from bulk RNA sequencing. The average discrepancy between the observed and predicted number of spots for each hybridization is only 15% of the mean number of spots. This discrepancy does not systematically increase with the number of hybridization rounds. FIG. 14B shows the average brightness of the identified fluorescent spots in each hybridization round averaged across all measurements with the first 16-bit MHD4 code both before (upper) and after (lower) photobleaching. Brightness varies by 40% (standard deviation) across different hybridization rounds. The variation pattern is reproducible between experiments with the same code, likely due to differences in the binding efficiency of the readout probes to the different readout sequences. There is a small systematic trend of decrease in the brightness with increasing hybridization rounds, which is on average 4% per round. Photobleaching extinguishes fluorescence to a level similar to that of the autofluorescence of the cell.

FIGS. 15A-15B show error correction substantially increases the numbers of RNA molecules and RNA species detected in individual cells. FIG. 15A shows a histogram of the ratio of the total number of molecules detected per cell with error correction to the number measured without error correction. FIG. 15B is a histogram of the total number of RNA species detected in each cell with error correction to that without error correction. Both ratios are determined for ~200 cells and the histograms are constructed from these ratios.

FIGS. 16A-16E show characterization of the misidentification and calling rates of RNA species for the 140-gene experiments using a specific 16-bit MHD4 code. FIG. 16A shows the number of measured words exactly matching the code word corresponding to FLNA, represented by the bar in the center of the circle, and the number of measured words with one-bit error compared to the code word of FLNA, represented by the 16 bars on the circle. FIG. 16B is the same as FIG. 16A, but for a code word that was not assigned to any RNA, i.e., a misidentification control word. The solid lines connect the exact match to one-bit error words that are generated by 1→0 errors. Based on the observation that the ratio of the number of exact matches to the number of error-correctable matches for a real RNA-encoding word was typically substantially higher than the same ratios observed for the misidentification controls, this ratio was defined as a confidence ratio for RNA identification. The confidence ratio measured for all 130 RNA species (center bar) and 10 misidentification control words not assigned to any RNA (outer bars) using this 16-bit MHD4 code is show in FIG. 6F. FIGS. 16C and 16D show the average error rates for the 1→0 error (FIG. 16C) and 0→1 error (FIG. 16D) for each hybridization round. FIG. 16E shows the calling rate for each RNA species estimated from the 1→0 and 0→1 error rates. Genes are sorted from left to right based on the measured abundance, which spans three orders of magnitude. The calling rates are largely independent of the abundance of the gene.

Figure 17A:
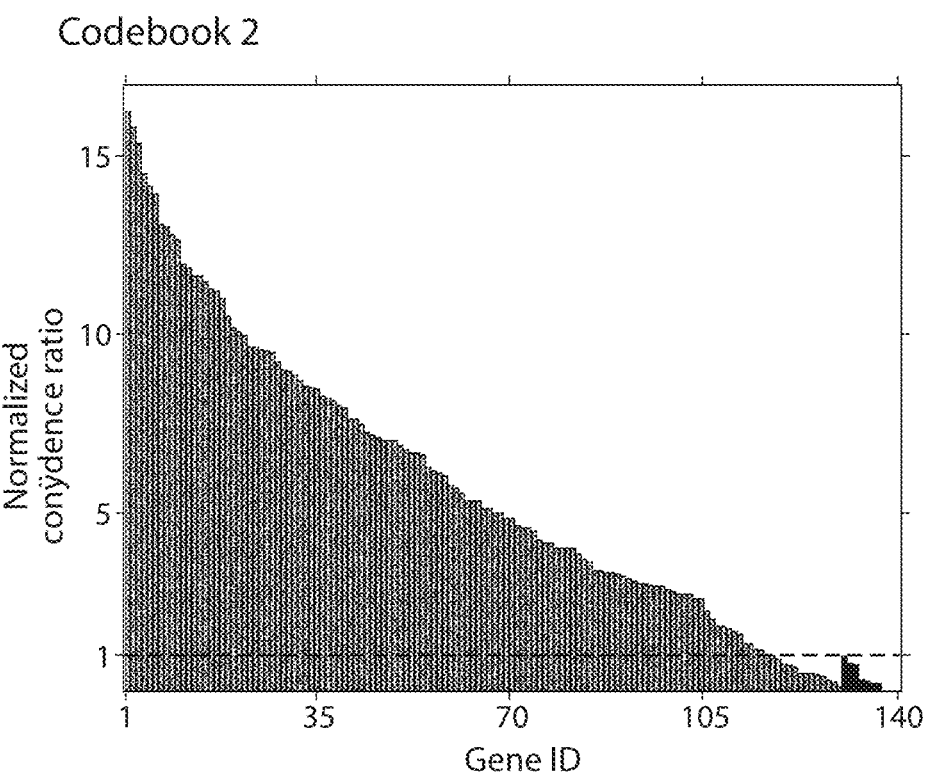
FIGS. 17A-17D show characterization of misidentification rates and calling rates, in another embodiment of the invention.
Figure 17B:
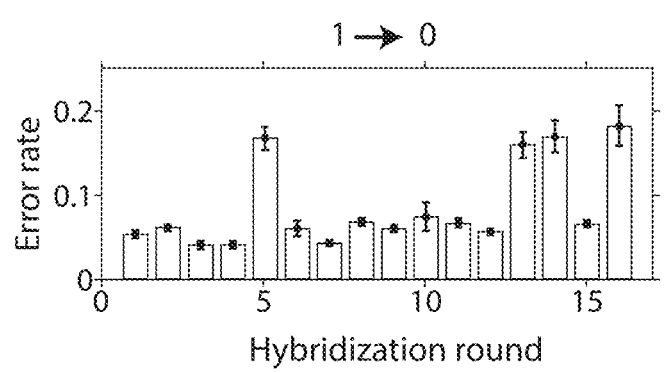
Figure 17C:
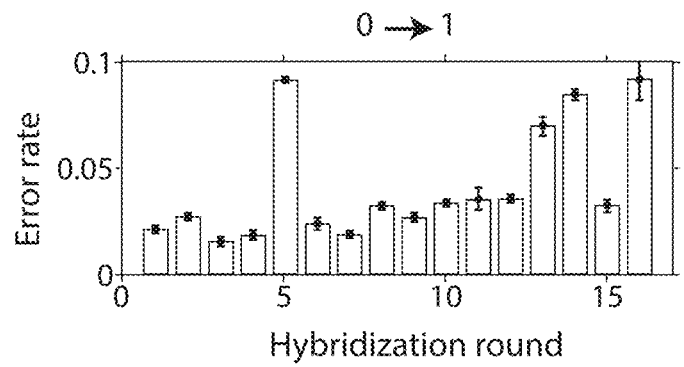
Figure 17D:
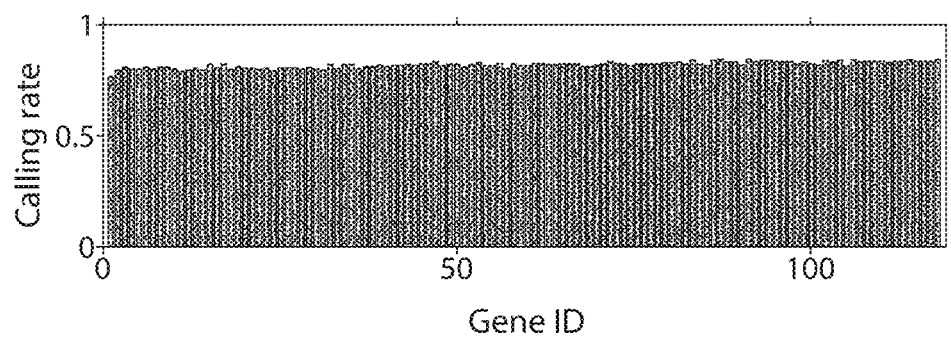

FIGS. 17A-17D show characterization of the misidentification and calling rates for a second 16-bit MHD4 code. In this second encoding scheme, the 140 code words were shuffled among different RNA species and changed the encoding probe sequences. FIG. 17A shows the normalized confidence ratio measured for the 130 RNA species (left) and the 10 misidentification control words not assigned to any RNA (right). The normalized confidence ratio is determined the same way as in FIG. 6F. FIGS. 17B and 17C show the average error rates determined for the 1→0 error (FIG. 17B) and 0→1 error (FIG. 17C) for each hybridization round. FIG. 17D shows the calling rate determined for each RNA species estimated from the 1→0 and 0→1 error rates. Genes are sorted from left to right based on the measured abundance.

Figure 18C:
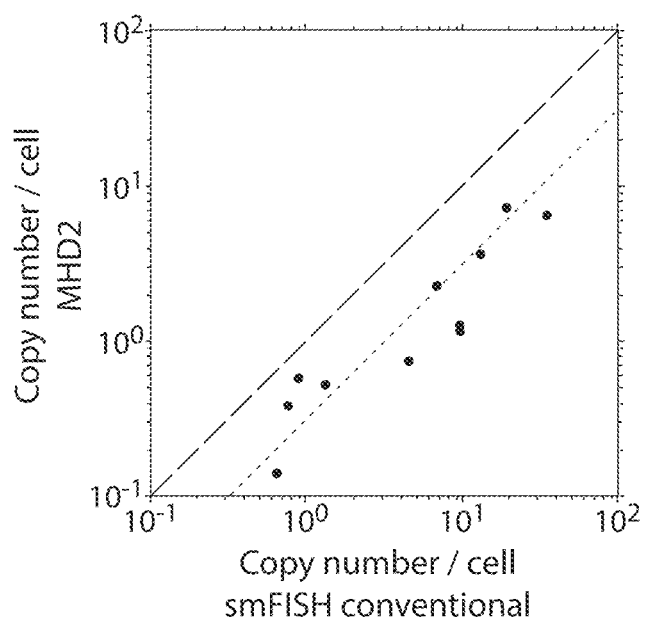

FIGS. 18A-18C show a comparison of the MERFISH measurements with conventional smFISH results for a subset of genes. FIG. 18A shows the distributions of RNA copy numbers in single cells for three example genes KIAA1199, DYNC1H1, and LMTK2 in the high, medium, and low abundance ranges, respectively. Lighter bars: distributions constructed from ~400 cells in the 140-gene measurements using the MHD4 codes. Darker bars: distributions constructed from ~100 cells in the conventional smFISH measurements. FIG. 18B shows a comparison of the average RNA copy numbers per cell measured in the 140-gene experiments using the MHD4 codes to those determined by conventional smFISH for 15 genes. The average ratio of the copy number measured using the MHD4 measurements to that measured using conventional smFISH was 0.82+/−0.06 (mean+/−SEM across 15 genes). The dashed line corresponds to the y=x line.

FIGS. 20A-20H show two different codebooks for the 140-gene experiments. The specific code words of the 16-bit MHD4 code assigned to each RNA species studied in the two shuffles of the 140-gene experiment. The "Genes" columns contain the name of the gene. The "Codewords" columns contain the specific binary word assigned to each gene.

Example 6

Figure 7A:
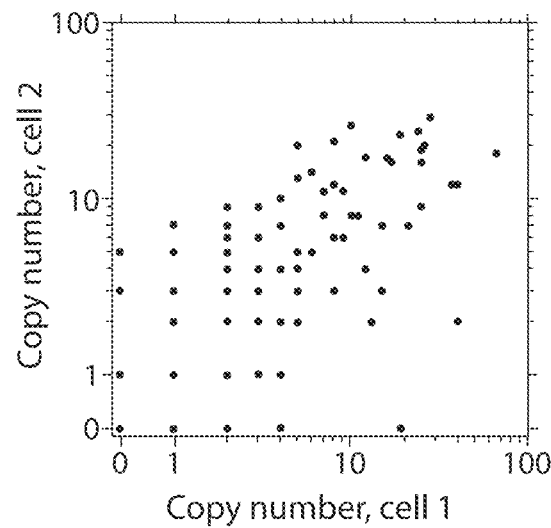
FIGS. 7A-7F show expression noise of genes and co-variation of expression between different genes determined in accordance with some embodiments of the invention.
Figure 7B:
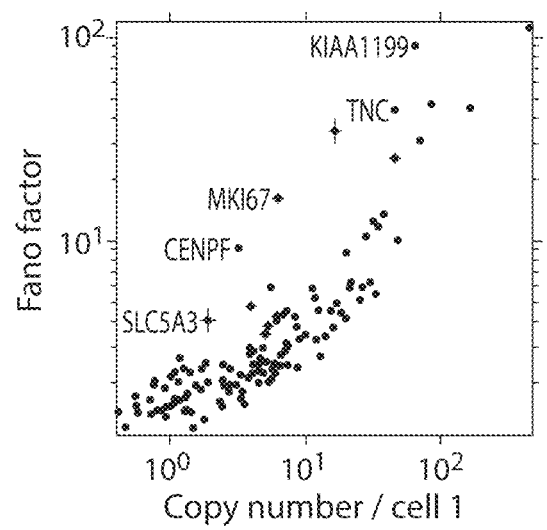

This example is generally directed to high-throughput analysis of cell-to-cell variation in gene expression. The MERFISH approach allows parallelization of measurements of many individual RNA species and co-variation analysis between different RNA species. In this example, the parallelization aspect was first illustrated by examining the cell-to-cell variation in the expression level of each of the measured genes (FIG. 7A). To quantify the measured variation, the Fano factors, defined as the ratio of the variance to the mean RNA copy number, were computed for all measured RNA species. The Fano factors substantially deviated from 1, the value expected for a simple Poisson process, for many genes and exhibited an increasing trend with the mean RNA abundance (FIG. 7B). This trend of increasing Fano factors with mean RNA abundance can be explained by changes in the transcription rate and/or promoter off-switching rates but not by changes in the promoter on-switching rate.

Moreover, several RNA species were identified with substantially larger Fano factors than this average trend. For example, it was found that SLC5A3, CENPF, MKI67, TNC and KIAA1199 displayed Fano factor values substantially higher than those of the other genes expressed at similar abundance levels. The high variability of some of these genes can be explained by their association with the cell cycle. For example, two of these particularly 'noisy' genes MKI67 and CENPF were both annotated as cell-cycle related genes, and based on their bimodal expression (FIG. 7C), it is proposed that their transcription is strongly regulated by the cell cycle. Other high-variability genes did not show the same bimodal expression patterns and are not known to be associated with the cell cycle.

Analysis of co-variations in the expression levels of different genes can reveal which genes are co-regulated and elucidate gene regulatory pathways. At the population level, such analysis often requires the application of external stimuli to drive gene expression variation; hence, correlated expression changes can be observed among genes that share common regulatory elements influenced by the stimuli. At the single-cell level, one can take advantage of the natural stochastic fluctuations in gene expression for such analysis and can thus study multiple regulatory networks without having to stimulate each of them individually. Such co-variation analysis can constrain regulatory networks, suggest new regulatory pathways, and predict function for unannotated genes based on associations with co-varying genes.

Figure 7C:
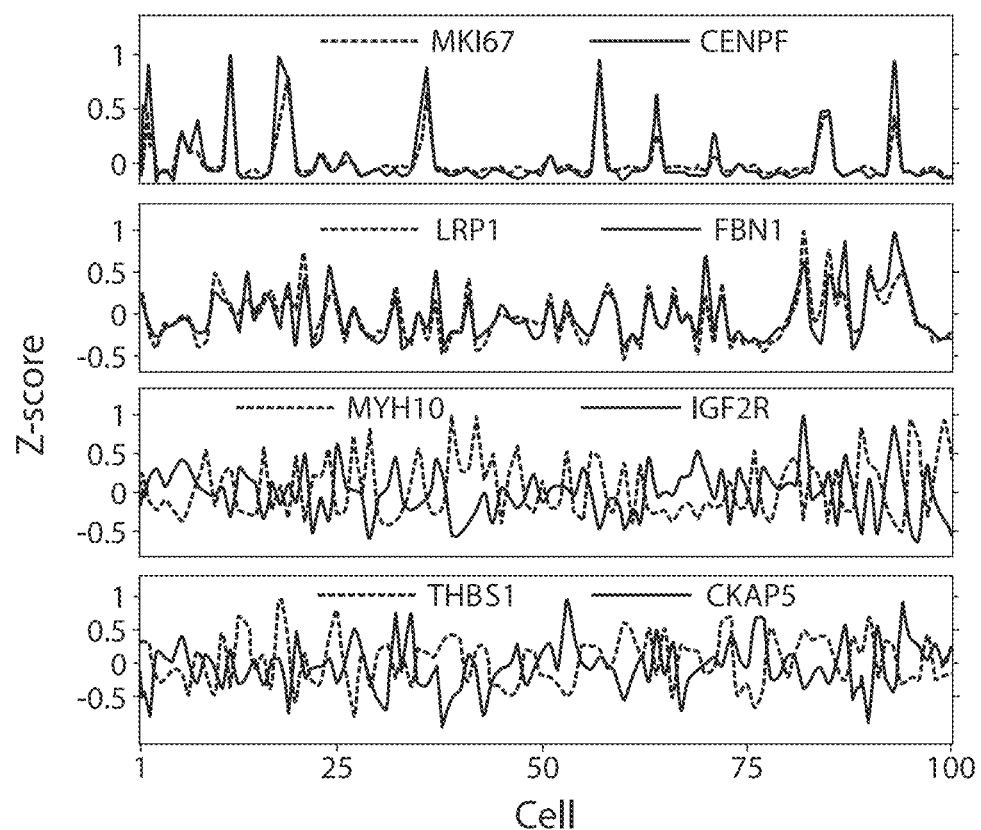
Figure 7D:
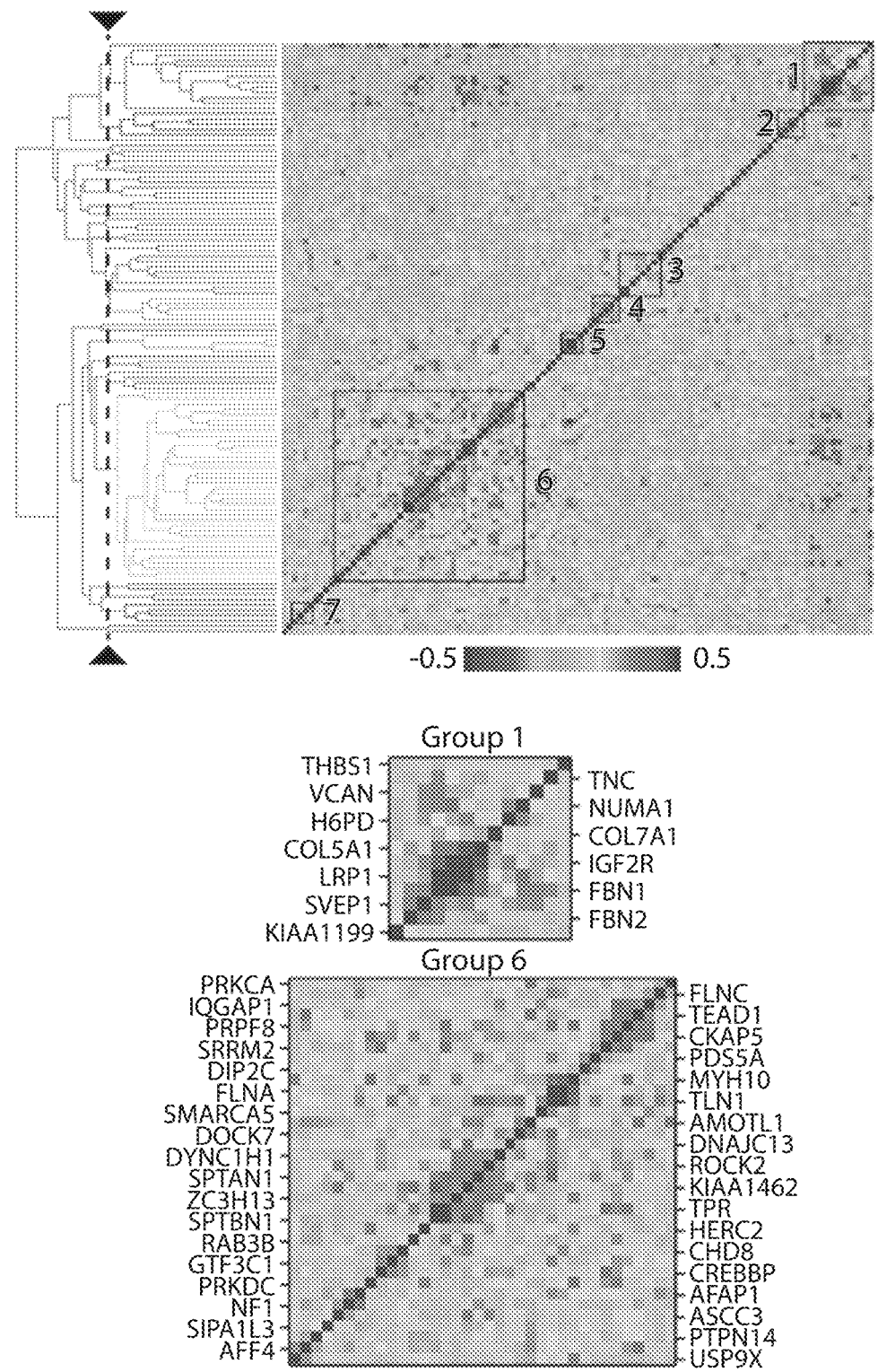

This approach was applied to the 140-gene measurements and the ~10,000 pairwise correlation coefficients describing how the expression levels of each pair of genes co-varied from cell to cell were examined. Many of the highly variable genes showed tightly correlated or anti-correlated variations (FIG. 7C). To better understand the correlations for all gene pairs, a hierarchical clustering approach was adopted to organize these genes based on their correlation coefficients (FIG. 7D). From the cluster tree structure, seven groups of genes with substantially correlated expression patterns were identified (FIG. 7D). Within each of the seven groups, every gene showed significantly stronger average correlation with other members of the group than with genes outside the group. To further validate and understand these groups, gene ontology (GO) terms enriched in each of these seven groups were identified. Notably, the enriched GO terms within each group shared similar functions and were largely unique to each group (FIGS. 7E and 7F), validating the notion that the observed co-variation in expression reflects some commonalities in the regulation of these genes.

Figure 7E:
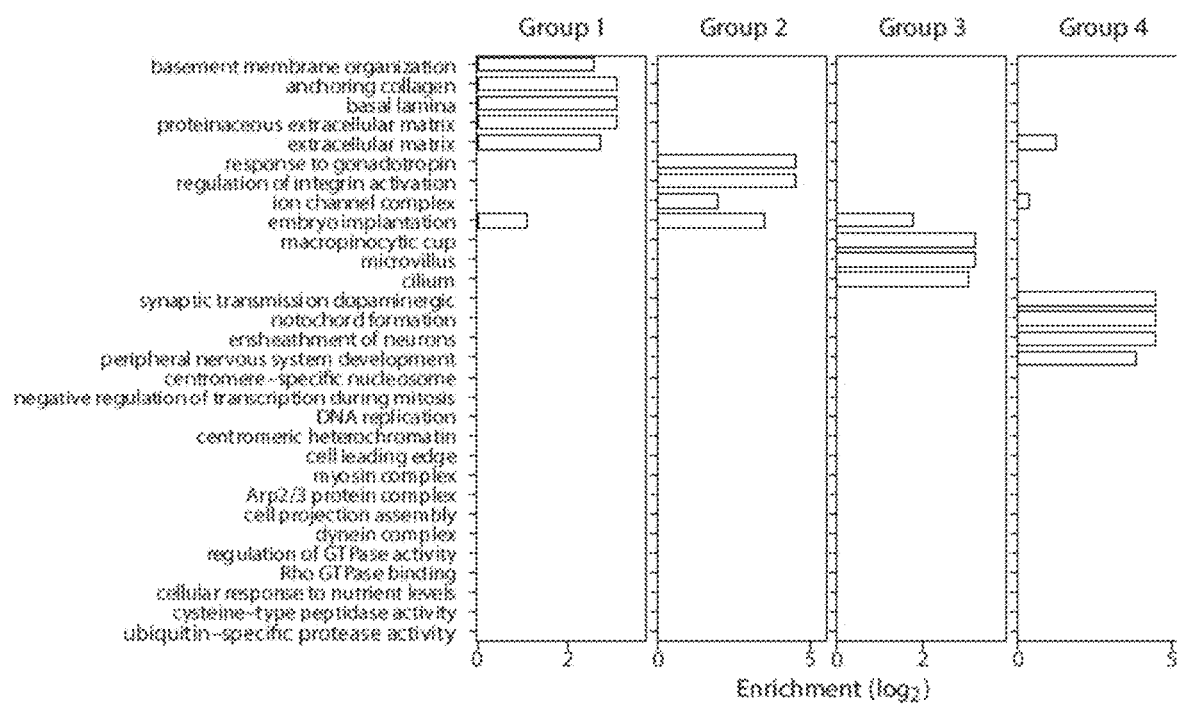
Figure 7F:
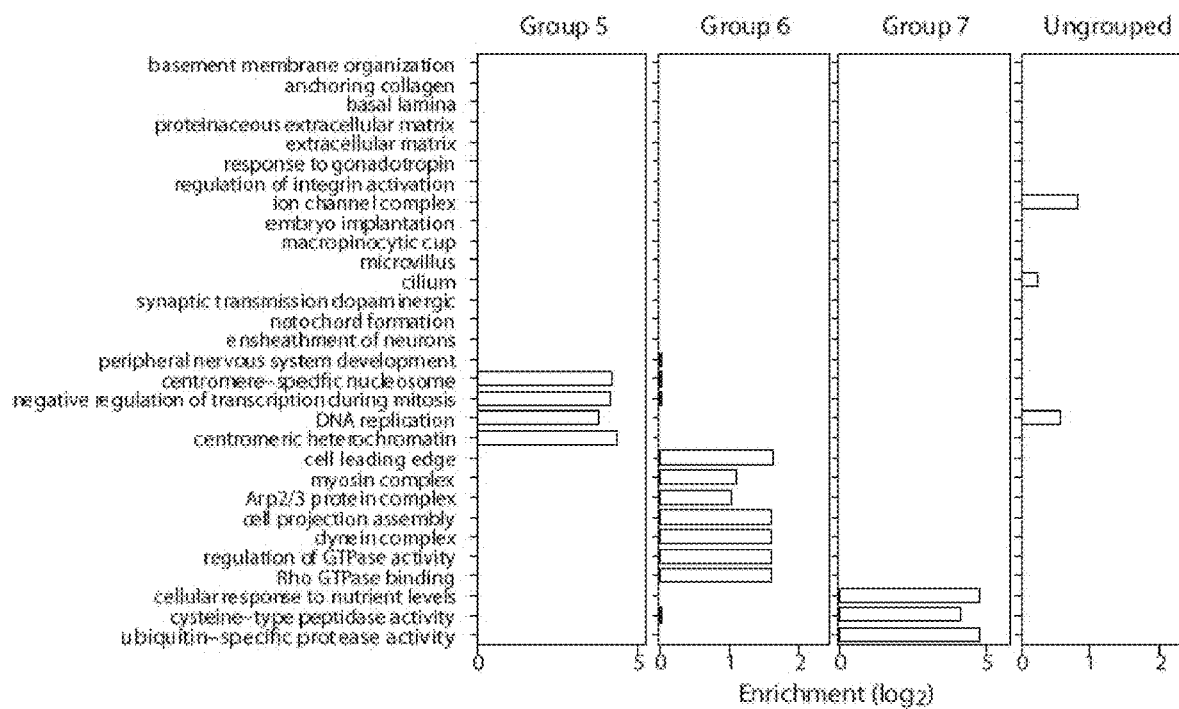

This example describes two of these groups as illustrative examples. The predominant GO terms associated with Group 1 were terms associated with the extracellular matrix (ECM) (FIGS. 7D to 7F). Notable members of this group included ECM components, such as FBN1, FBN2, COL5A, COL7A and TNC, and glycoproteins linking the ECM and cell membranes, such as VCAN and THBS1. The group also included an unannotated gene, KIAA1199, which may predict to play a role in ECM metabolism based on its association with this cluster. Indeed, this gene has recently been identified as an enzyme involved in the regulation of hyaluronan, a major sugar component of the ECM.

Group 6 contained many genes that encode vesicle transport proteins and proteins associated with cell motility (FIGS. 7D to 7F). The vesicle transport genes included microtubule motors and related genes DYNC1H, CKAP1, and factors associated with vesicle formation and trafficking, like DNAJC13 and RAB3B. Again, an unannotated gene, KIAA1462, was found within this cluster. Based on its strong correlation with DYNC1H1 and DNAJC13, it is predicted that this gene may be involved in vesicle transport. The cell motility genes in this group included actin-binding proteins like AFAP1, SPTAN1, SPTBN1, and MYH10, and genes involved in the formation of adhesion complexes, like FLNA and FLNC. Several GTPase-associated factors involved in the regulation of cell motility, attachment and contraction also fell into this group, including DOCK7, ROCK2, IQGAP1, PRKCA, and AMOTL1. The observation that some cell motility genes correlated with vesicle transport genes is consistent with the role of vesicle transport in cell migration. An additional interesting feature of group 6 is that a subset of these genes, in particular those related to cell motility, were anti-correlated with members of the ECM group discussed above (FIG. 7D). This anti-correlation may reflect regulatory interactions that mediate switching of cells between adherent and migratory states.

FIGS. 7A-7F show cell-to-cell variations and pairwise correlations for the RNA species determined from the 140 gene measurements. FIG. 7A shows a comparison of gene expression levels in two individual cells. FIG. 7B shows Fano factors for individual genes. Error bars represent standard error of the mean determined from 7 independent data sets. FIG. 7C shows Z-scores of the expression variations of four example pairs of genes showing correlated (top two) or anti-correlated (bottom two) variation for 100 randomly selected cells. The Z-score is defined as the difference from the mean normalized by the standard deviation. FIG. 7D is a matrix of the pairwise correlation coefficients of the cell-to-cell variation in expression for the measured genes, shown together with the hierarchical clustering tree. The seven groups identified by a specific threshold on the cluster tree (dashed line) are indicated by the black boxes in the matrix and lines on the tree, with grey lines on the tree indicating ungrouped genes. Different threshold choices on the cluster tree could be made to select either smaller subgroups with tighter correlations or larger super-groups containing more weakly coupled subgroups. Two of the seven groups are enlarged on the right. FIG. 7E shows enrichment of 30 selected, statistically significantly enriched GO terms in the seven groups. Enrichment refers to the ratio of the fraction of genes within a group that have the specific GO term to the fraction of all measured genes having that term. Not all of the GO terms presented here are in the top 10 list.

Example 7

Figure 8A:
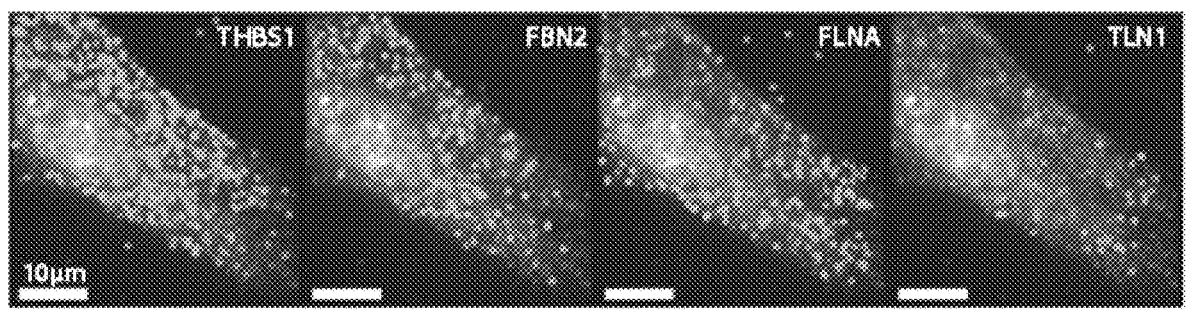
FIGS. 8A-8E illustrate spatial distribution of RNAs in cells determined in accordance with one embodiment of the invention.
Figure 8B:
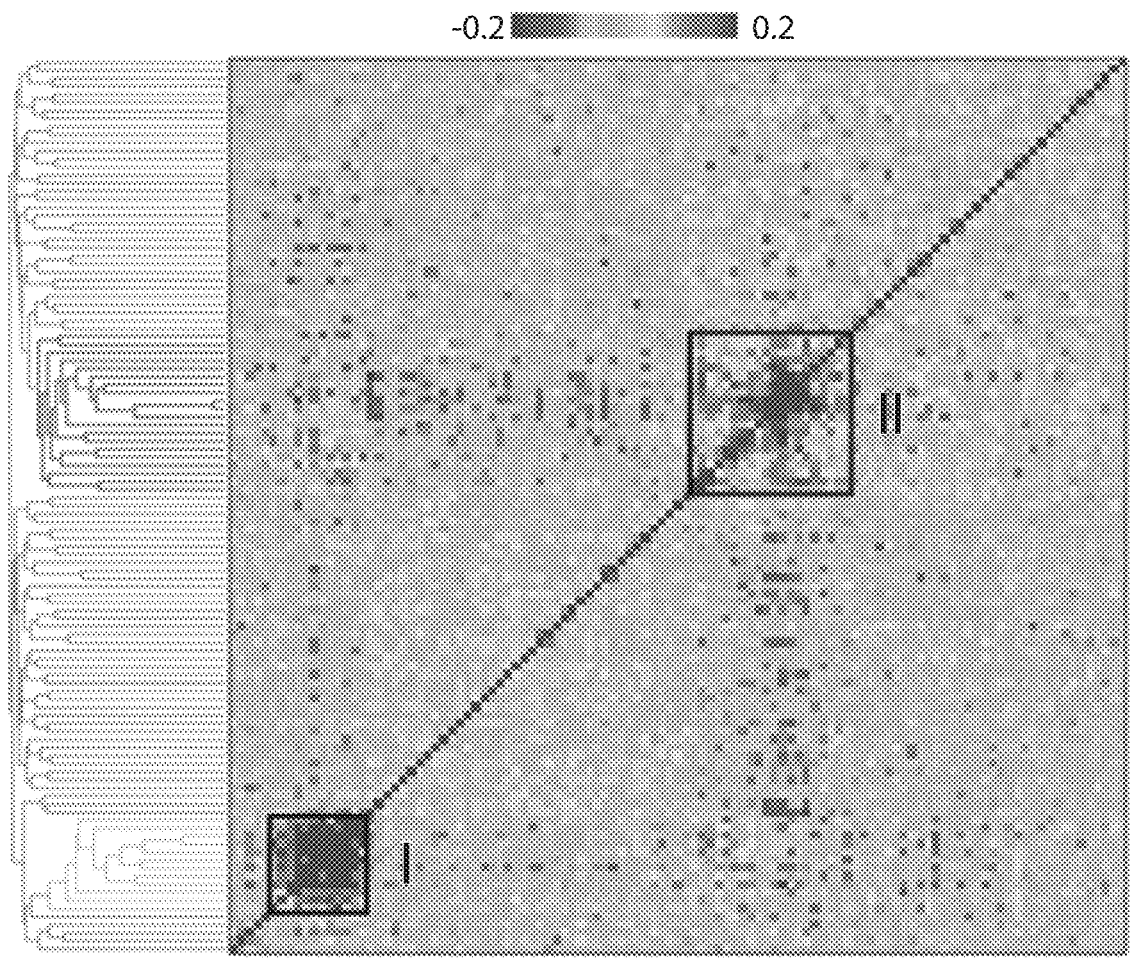
Figure 8C:
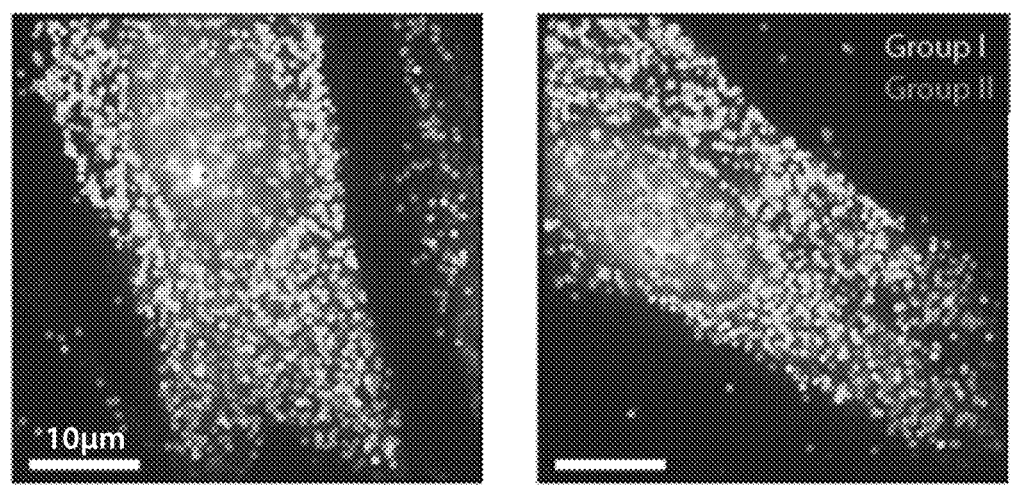

This example illustrates mapping spatial distributions of RNAs. As an imaging based approach, MERFISH also allowed the investigation of the spatial distributions of many RNA species simultaneously. Several patterns emerged from the visual inspection of individual genes, with some RNA transcripts enriched in the perinuclear region, some enriched in the cell periphery, and some scattered throughout the cell (FIG. 8A). To identify genes with similar spatial distributions, the correlation coefficients for the spatial density profiles of all pairs of RNA species were determined, and these RNAs were organized based on the pairwise correlations again using the hierarchical clustering approach. The correlation coefficient matrix showed groups of genes with correlated spatial organizations, and the two most notable groups with the strongest correlations are indicated in FIG. 8B. Group I RNAs appeared enriched in the perinuclear region whereas group II RNAs appeared enriched near the cell peripheral region (FIG. 8C). Quantitative analysis of the distances between each RNA molecule and the cell nucleus or the cell periphery indeed confirmed this visual impression (FIG. 8D).

Group I contained genes encoding extracellular proteins such as FBN1, FBN2 and THSB1, secreted proteins such as PAPPA, and integral membrane proteins such as LRP1 and GPR107. These proteins have no obvious commonalities in function. Rather a GO analysis showed significant enrichment for location terms, such as extracellular region, basement membrane, or perivitelline space (FIG. 8E). To reach these locations, proteins must pass through the secretion pathway, which often requires translation of mRNA at the endoplasmic reticulum (ER). Thus, it is proposed that the spatial pattern that were observed for these mRNAs reflects their co-translational enrichment at the ER. The enrichment of these mRNAs in the perinuclear region (FIGS. 8C and 8D, lighter shading), where the rough ER resides, supports this conclusion.

Group II contained genes encoding the actin-binding proteins, including filamins FLNA and FLNC, talin TLN1, and spectrins SPTAN1 and SPTBN1; the microtubule-binding protein CKAP5; and the motor proteins MYH10 and DYNC1H1. This group was enriched with GO terms such as cortical actin cytoskeleton, actin filament binding, and cell-cell adherens junction (FIG. 8E). Beta-actin mRNA may be enriched near the cell periphery in fibroblasts as are mRNAs that encode members of the actin-binding Arp2/3 complex. The enrichment of group II mRNAs in the peripheral region of the cells (FIGS. 8C and 8D) suggests that the spatial distribution of the Group II genes might be related to the distribution of actin cytoskeleton mRNAs.

Figure 8D:
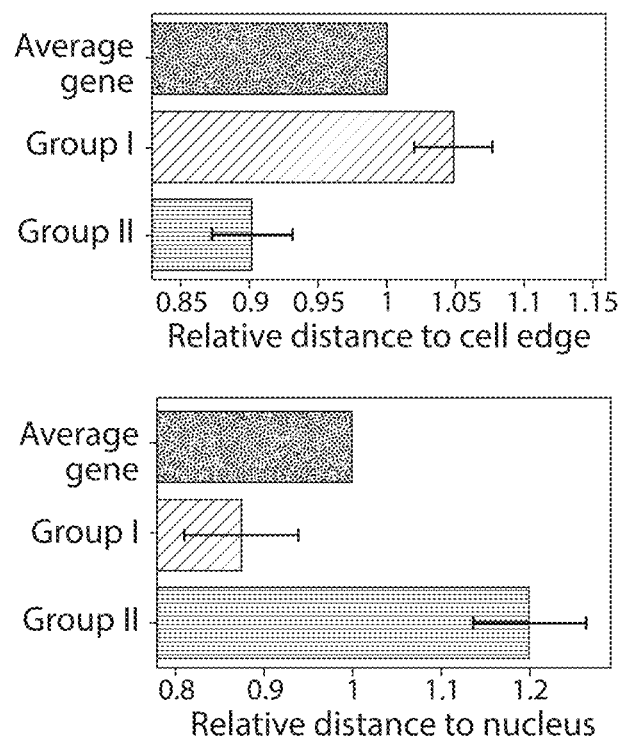
Figure 8E:
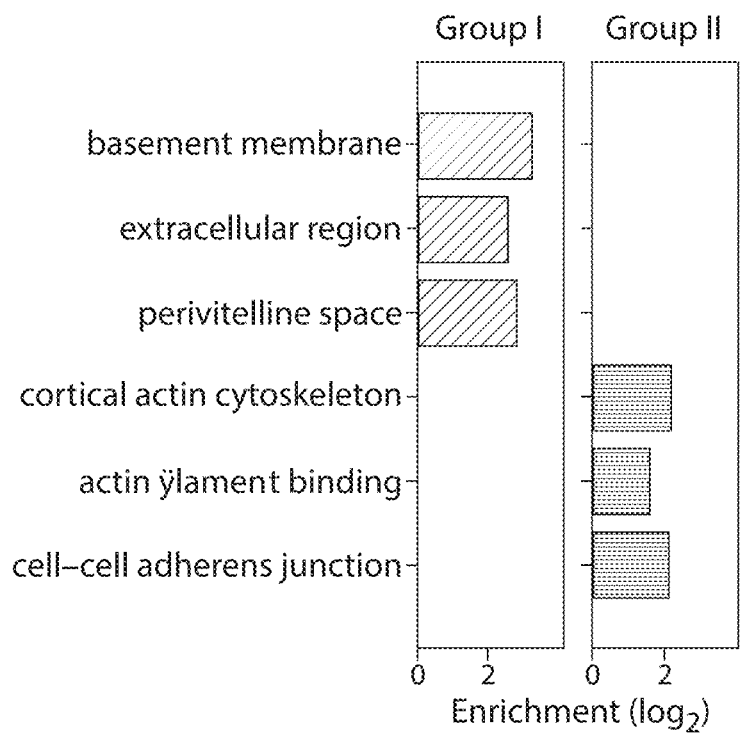

FIGS. 8A-8E show distinct spatial distributions of RNAs observed in the 140-gene measurements. FIG. 8A shows examples of the spatial distributions observed for four different RNA species in a cell. FIG. 8B is a matrix of the pairwise correlation coefficients describing the degree with which the spatial distributions of each gene pair is correlated, shown together with the hierarchical clustering tree. Two strongly correlating groups are indicated by the black boxes on the matrix and shading on the tree. FIG. 8C shows the spatial distributions of all RNAs in the two groups in two example cells. Lighter symbols: group I genes; darker symbols: group II genes. FIG. 8D shows average distances for genes in group I and genes in group II to the cell edge or the nucleus normalized to the average distances for all genes. Error bars represent SEM across 7 data sets. FIG. 8E shows enrichment of GO terms in each of the two groups.

Example 8

This example illustrates measuring 1001 genes with a 14-bit MHD2 code. This example further increases the throughput of MERFISH measurements by simultaneously imaging ~1000 RNA species. This increase could be achieved with the MHD4 code by increasing the number of bits per code word to 32 while maintaining the number of '1' bits per word at four (FIG. 5B). While the stability of the samples across many hybridization rounds (FIG. 14) suggests that such an extension is potentially feasible, an alternative approach is shown here that did not require an increase in the number of hybridizations by relaxing the error correction requirement but keeping the error detection capability. For example, by reducing the Hamming distance from 4 to 2, all 14-bit words could be used that contain four '1' bits to encode 1001 genes and these RNAs were probed with only 14 rounds of hybridization. However, because a single error can produce a word equally close to two different code words, error correction is no longer possible for this modified Hamming-distance-2 (MHD2) code. Hence, it was expected that the calling rate would be lower and the misidentification rate to be higher with this encoding scheme.

To evaluate the performance of this 14-bit MHD2 code, 16 of the 1001 possible code words were set aside as misidentification controls and used the remaining 985 words to encode cellular RNAs. Among these 985 RNAs included 107 RNA species probed in the 140-gene experiments as an additional control. The 1001-gene experiments were performed in IMR90 cells using a similar procedure as described above. To allow all encoding probes to be synthesized from a single 100,000-member oligopool, the number of encoding probes per RNA species was reduced to ~94. Fluorescent spots corresponding to individual RNA molecules were again detected in each round of hybridization with the readout probes and, based on their on-off patterns, these spots were decoded into RNA (FIGS. 9A, 19A and 19B). 430 RNA species were detected in the cell shown in FIG. 9A, and similar results were obtained in ~200 imaged cells in 3 independent experiments.

Figure 19C:
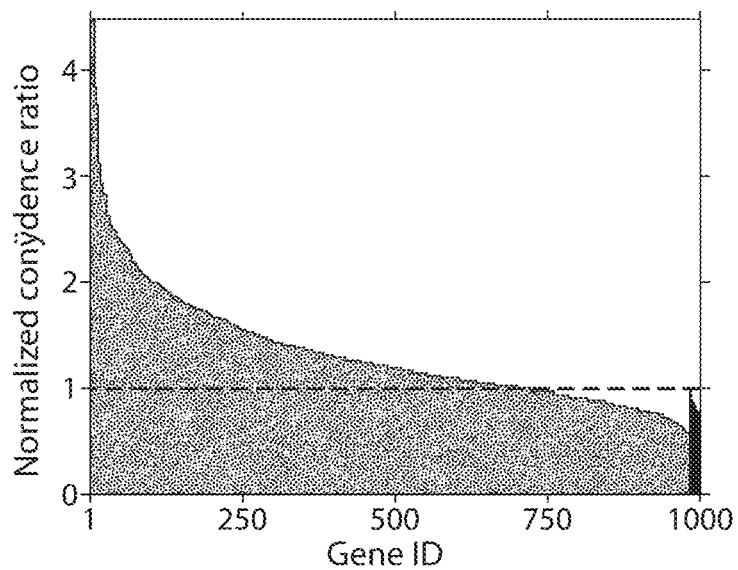

As expected, the misidentification rate of this scheme was higher than that of the MHD4 code. 77% of all real RNA words were detected more frequently than the median count for the misidentification controls instead of the 95% value observed in the MHD4 measurements. Using the same confidence ratio analysis as described above, it was found that 73% (instead of 91% for the MHD4 measurements) of the 985 RNA species were measured with a confidence ratio larger than the maximum value observed for the misidentification controls (FIG. 19C). RNA copy numbers measured from these 73% RNA species showed excellent correlation with the bulk RNA sequencing results (Pearson correlation coefficient r=0.76; FIG. 9B, black). It is worth noting that the remaining 27% of the genes still exhibit good, albeit lower, correlation with the bulk RNA sequencing data (r=0.65; FIG. 9B, red), but the conservative measure of excluding them from further analysis was taken.

Figure 19D:
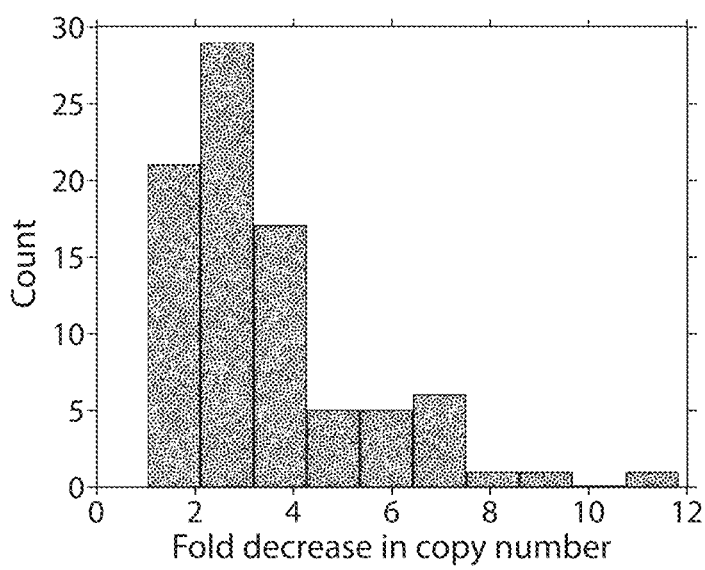

The lack of an error correction capability also decreased the calling rate of each RNA species: When comparing the 107 RNA species common in both the 1001-gene and 140-gene measurements, it was found that the copy numbers per cell of these RNA species were lower in the 1001-gene measurements (FIGS. 9C and 19D). The total count of these RNAs per cell was ~⅓ of that observed in the 140-gene measurements. Thus the lack of error correction in the MHD2 code produced a ~3-fold decrease in the calling rate, which is consistent with the ~4-fold decrease in calling rate observed for the MHD4 code when error correction was not applied. As expected from the quantitative agreement between 140-gene measurements and conventional smFISH results, comparison of the 1001-gene measurements with conventional smFISH results for 10 RNA species also indicated a ~3-fold drop in calling rate (FIG. 18C). Despite the expected reduction in calling rate, the good correlations found between the copy numbers observed in the 1001-gene measurements and those observed in the 140-gene measurements, as well as in conventional smFISH and bulk RNA sequencing measurements, indicates that the relative abundance of these RNAs can be quantified with the MHD2 encoding scheme.

Figure 10A:
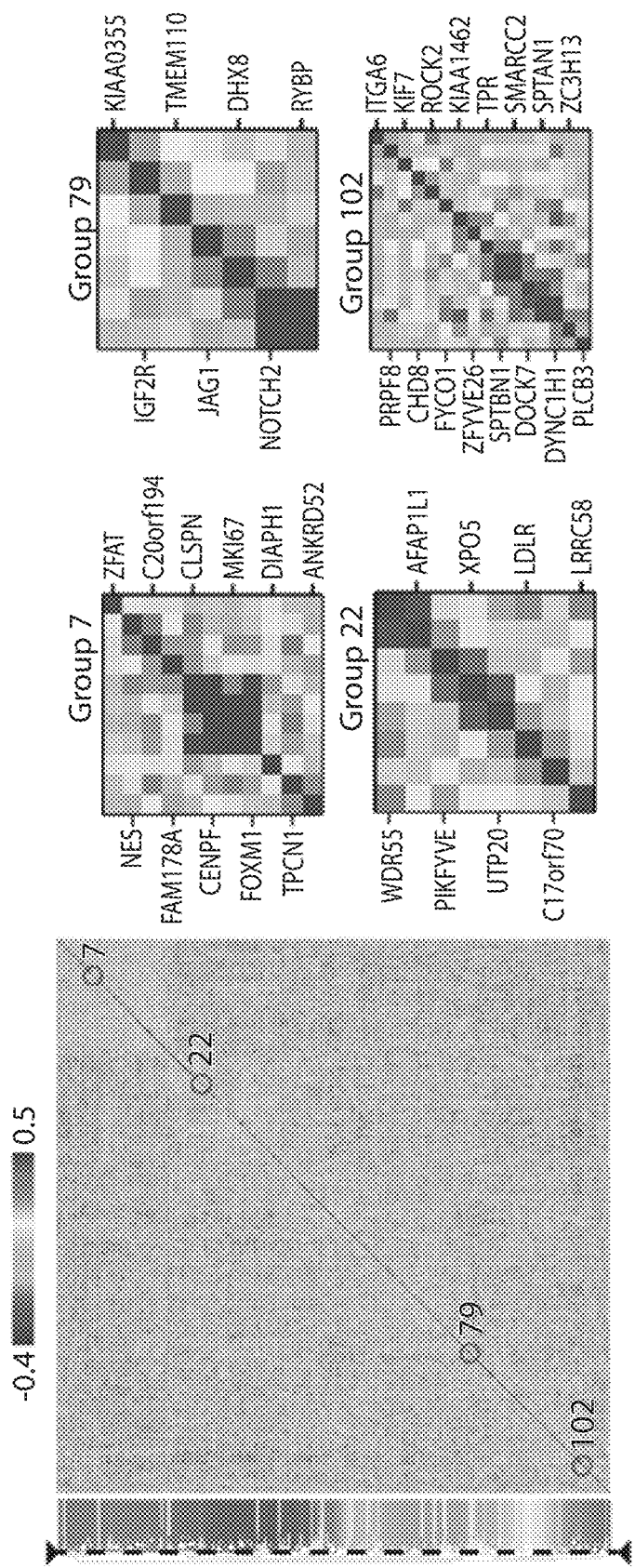
FIGS. 10A-10C show expression between different genes determined in accordance with yet another embodiment of the invention.
Figure 10B:
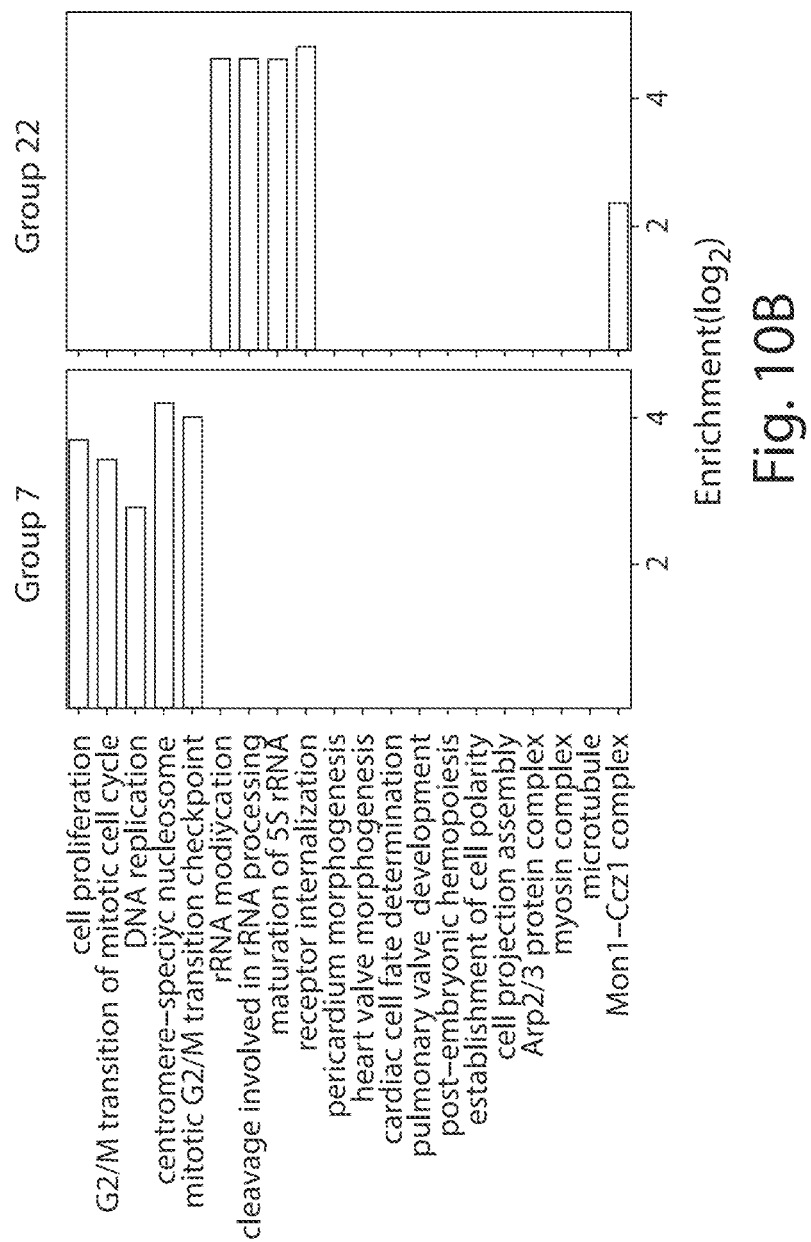
Figure 10C:
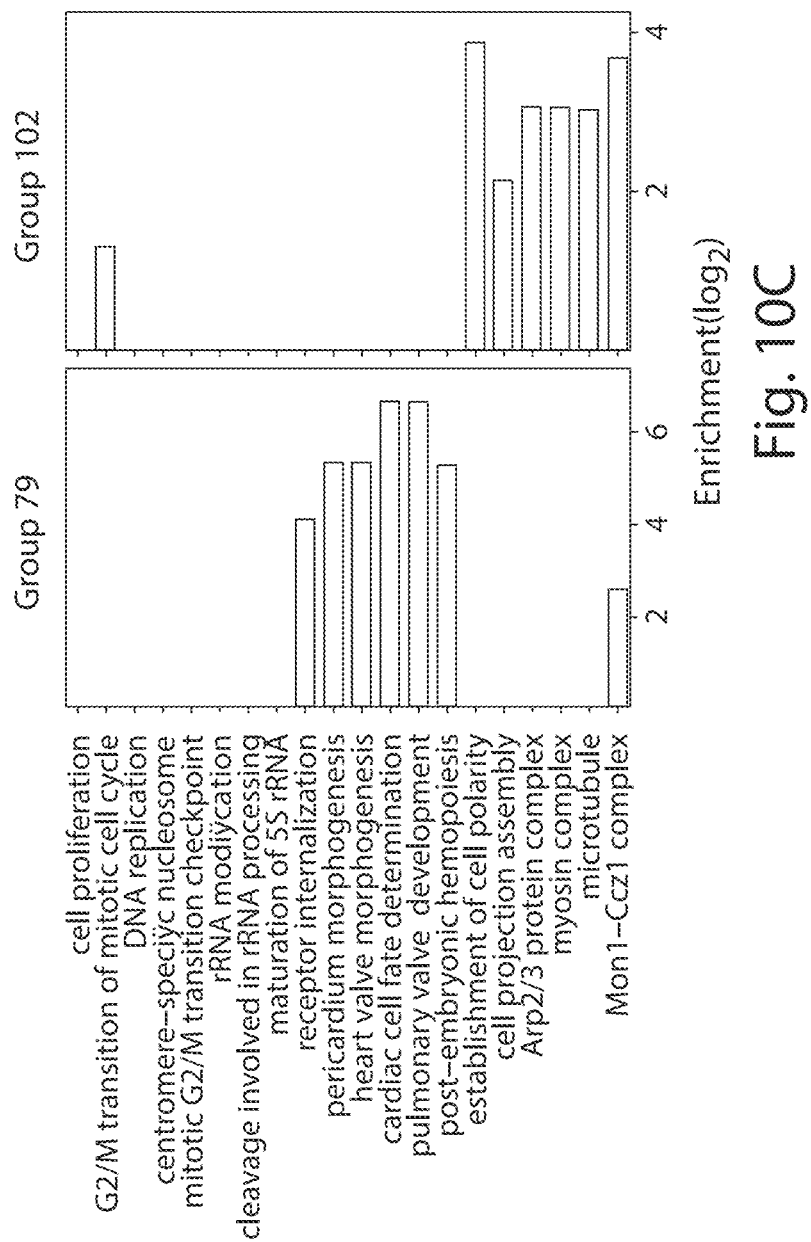

Simultaneously imaging ~1000 genes in individual cells substantially expanded the ability to detect co-regulated genes. FIG. 10A shows the matrix of pairwise correlation coefficients determined from the cell-to-cell variations in the expression levels of these genes. Using the same hierarchical clustering analysis as described above, ~100 groups of genes with correlated expression were identified. Remarkably, nearly all of these ~100 groups showed statistically significant enrichment of functionally related GO terms (FIG. 10B-FIG. 10C). These included some of the groups identified in the 140-gene measurements, such as the group associated with cell replication genes and the group associated with cell motility genes (FIGS. 10A and 10B and 10C, groups 7 and 102), as well as many new groups. The groups identified here included 46 RNA species lacking any previous GO annotations, for which function based on their group association may be hypothesized. For example, KIAA1462 is part of the cell motility group, as also shown in the 140-gene experiments, suggesting a potential role of this gene in cell motility (FIG. 10A, group 102). Likewise, KIAA0355 is part of a new group enriched in genes associated with heart development (FIG. 10A, group 79), and C17orf70 is part of a group associated with ribosomal RNA processing (FIG. 10A, group 22). Using these groupings, cellular functions for 61 transcription factors and other partially annotated proteins of unknown functions may be hypothesized. For example, the transcription factors Z3CH13 and CHD8 are both members of the cell motility group, suggesting their potential role in the transcriptional regulation of cell motility genes.

Figure 9A:
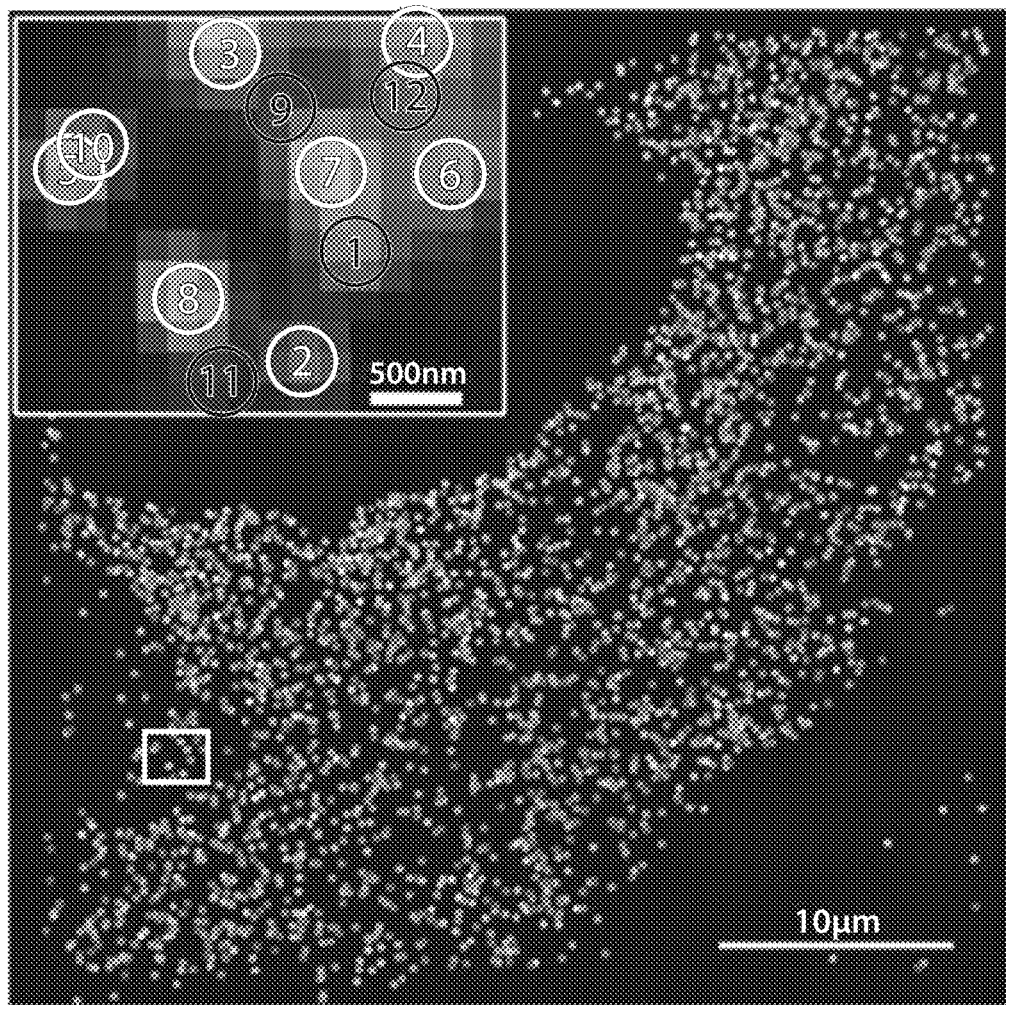
FIGS. 9A-9C illustrate simultaneous determination of multiple nucleic acid species in cells, in another embodiment of the invention.
Figure 9B:
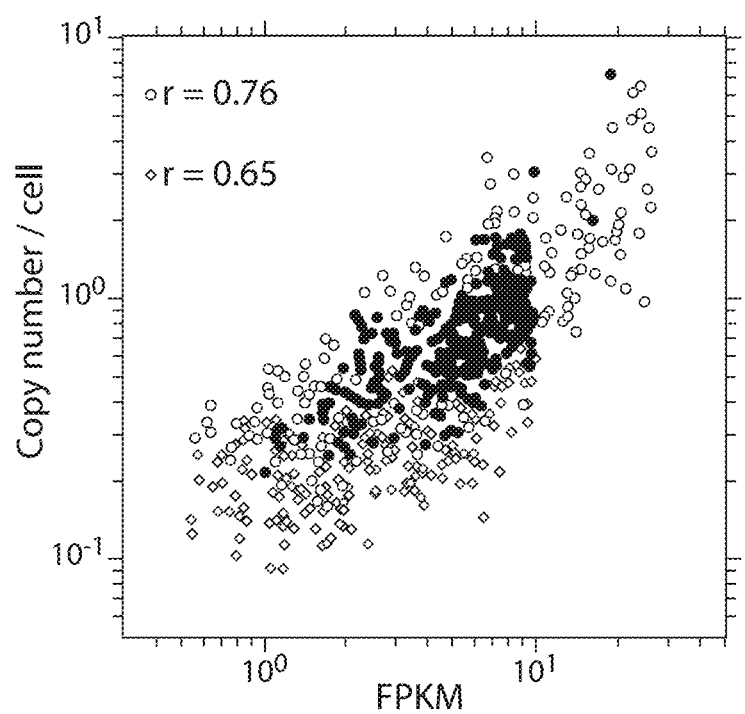
Figure 9C:
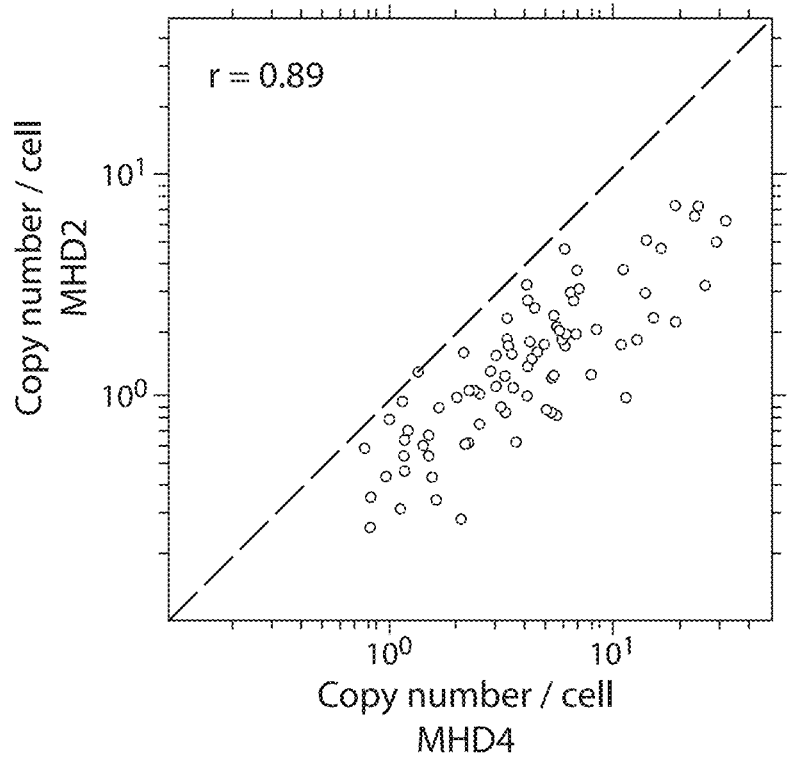

FIGS. 9A-9C show simultaneous measurements of 1001 genes in single cells using MERFISH with a 14-bit MHD2 code. FIG. 9A shows the localizations of all detected single molecules in a cell colored based on their measured binary words. Inset: the composite, false-colored fluorescent image of the 14 hybridization rounds for the boxed sub-region with numbered circles indicating potential RNA molecules. Circles indicate unidentifiable molecules, the binary words of which do not match any of the 14-bit MHD2 code words. Images of individual hybridization round are shown in FIG. 19A. FIG. 9B is a scatter plot of the average copy number per cell measured in the 1001-gene experiments versus the abundance measured via bulk sequencing. The upper symbols are for the 73% of genes detected with confidence ratios higher than the maximum ratio observed for the misidentification controls. The Pearson correlation coefficient is 0.76 with a p-value of $3 \times 10^{-133}$. The lower symbols are for the remaining 27% of genes. The Pearson correlation coefficient is 0.65 with a p-value of $3 \times 10^{-33}$. FIG. 9C is a scatter plot of the average copy number for the 107 genes shared in both the 1001-gene measurement with the MHD2 code and the 140-gene measurement with the MHD4 code. The Pearson correlation coefficient is 0.89 with a p-value of $9 \times 10^{-30}$. The dashed line corresponds to the y=x line.

FIGS. 10A-10C show co-variation analysis of the RNA species measured in the 1001-gene measurements. FIG. 10A is a matrix of all pairwise correlation coefficients of the cell-to-cell variation in expression for the measured genes shown with the hierarchical clustering tree. The ~100 identified groups of correlated genes are indicated by shading on the tree. Zoom in of four of the groups described in the text are shown on the right. FIG. 10B-FIG. 10C is an enrichment of 20 selected, statistically significantly enriched GO terms in the four groups.

FIGS. 19A-19D show decoding and error assessment of the 1001-gene experiments. FIG. 19A shows images of the boxed sub-region of the cell in FIG. 9A for each of 14 hybridization rounds. The final panel is a composite image of these 14 rounds. Circles indicate fluorescent spots that have been identified as potential RNA molecules. Some circles in the composite image indicate unidentifiable molecules, the binary words of which do not match any of the 14-bit MHD2 code words. FIG. 9B shows the corresponding binary word for each of the spots identified in FIG. 9A with the RNA species to which it is decoded. 'unidentified' implies that the measured binary word does not match any of the 1001 code words. FIG. 19C shows the normalized confidence ratios measured for the 985 RNA species (left) and the 16 misidentification control words not targeted to any RNA (right). The normalized confidence ratio is defined as in FIG. 6F. FIG. 19D shows a histogram of the reduction in detected abundance of 107 genes present in both the 1001-gene experiments and the 140-gene experiments. "Fold decrease in copy number" is defined as the average number of RNA molecules per cell for each species measured in the 140-gene experiments divided by the corresponding average number measured in the 1001-gene experiments.

FIG. 18C is a comparison of the average RNA copy numbers per cell measured in the 1001-gene experiments using the MHD2 code to those determined by conventional smFISH for 10 genes. The average ratio of the copy number measured using the MHD2 measurements to that measured using conventional smFISH was 0.30+/−0.05 (mean+/−

Example 9

The above examples illustrate a highly multiplexed detection scheme for systems-level RNA imaging in single cells. Using combinatorial labeling, sequential hybridization and imaging, and two different error-robust encoding schemes, either 140 or 1001 genes in hundreds of individual human fibroblast cells were simultaneously imaged. Of the two encoding schemes presented here, the MHD4 code is capable of both error detection and error correction, and hence can provide a higher calling rate and a lower misidentification rate than the MHD2 code, which instead can only detect but cannot correct errors. MHD2, on the other hand, provides a faster scaling of the degree of multiplexing with the number of bits than MHD4. Other error-robust encoding schemes can also be used for such multiplexed imaging, and experimenters can set the balance between detection accuracy and ease of multiplexing based on the specific requirements of the experiments.

By increasing the number of bits in the code words, it should be possible to further increase the number of detectable RNA species using MERFISH with, for example, a MHD4 or MHD2 code. For example, using the MHD4 code with 32 total bits and four or six '1' bits would increase the number of addressable RNA species to 1,240 or 27,776, respectively. The latter is the approximate scale of the human transcriptome. The predicted misidentification and calling rates are still reasonable for the 32-bit MHD4 code (shown in FIGS. 5C and 5D for the MHD4 code with four '1' bits and similar rates were calculated for the MHD4 code with six '1' bits). If more accurate measurements are desired, an additional increase in the number of bits would allow the use of encoding schemes with a Hamming distance greater than 4, further enhancing the error detection and correction capability. While an increase in the number of bits by adding more hybridization rounds would increase the data collection time and potentially lead to sample degradation, these problems could be mitigated by utilizing multiple colors to readout multiple bits in each round of hybridization.

As the degree of multiplexing is increased, it is important to consider the potential increase in the density of RNAs that need to be resolved in each round of imaging. Based on the imaging and sequencing results, it can be estimated that including the whole transcriptome of the IMR90 cells would lead to a total RNA density of ~200 molecules/micrometer$^3$. Using the current imaging and analysis methods, 2-3 molecules/micrometer$^3$ per hybridization round could be resolved, which would reach a total RNA density of ~20 molecules/micrometer$^3$ after 32 rounds of hybridization. This density should allow all but the top 10% most expressed genes to be imaged simultaneously or a subset of genes with even higher expression levels to be included. By utilizing more advanced image analysis algorithms to better resolve overlapping images of individual molecules, such as compressed sensing, it is possible to extend the resolvable density by ~4-fold and thus allow all but the top 2% most expressed genes to be imaged all together.

These examples have illustrated the utility of the data derived from highly multiplexed RNA imaging by using co-variation and correlation analysis to reveal distinct sub-cellular distribution patterns of RNAs, to constrain gene regulatory networks, and to predict functions for many previously unannotated or partially annotated genes with unknown functions. Given its ability to quantify RNAs across a wide range of abundances without amplification bias while preserving native context, systems and methods such as MERFISH will allow many applications of in situ transcriptomic analyses of individual cells in culture or complex tissues.

Example 10

Following are various materials and methods used in the above examples.

Probe design. Each RNA species in the target set was randomly assigned a binary code word either from all 140 possible code words of the 16-bit MHD4 code or from all 1001 possible code words of the 14-bit MHD2 code.

Array-synthesized oligopools were used as templates to make the encoding probes. The template molecule for each encoding probe contained three components: i) a central targeting sequence for in situ hybridization to the target RNA, ii) two flanking readout sequences designed to hybridize each of two distinct readout probes, and iii) two flanking primer sequences to allow enzymatic amplification of the probes (FIG. 13). The readout sequences were taken from the 16 possible readout sequences, each corresponding to one hybridization round. The readout sequences were assigned to the encoding probes such that for any RNA species each of the 4 readout sequences were distributed uniformly along the length of the target RNA and appeared at the same frequency. Template molecules for the 140-gene library also included a common 20-nucleotide (nt) priming region between the first PCR primer and the first readout sequence. This priming sequence was used for the reverse transcription step described below.

Multiple experiments were embedded in a single array-synthesized oligopool, and PCR was used to selectively amplify only the oligos required for a specific experiment. Primer sequences for this indexed PCR reaction were generated from a set of orthogonal 25-nt sequences. These sequences were trimmed to 20 nt and selected for i) a narrow melting temperature range (70° C. to 80° C.), ii) the absence of consecutive repeats of 3 or more identical nucleotides, and iii) the presence of a GC clamp, i.e. one of the two 3' terminal bases must be G or C. To further improve specificity, these sequences were then screened against the human transcriptome using BLAST+, and primers with 14 or more contiguous bases of homology were eliminated. Finally, BLAST+ was again used to identify and exclude primers that had an 11-nt homology region at the 3' end of any other primer or a 5-nt homology region at the 3' end of the T7 promoter. The forward primer sequences (Primer 1) were determined as described above, whereas the reverse primers each contain a 20-nt sequence as described above plus a 20-nt T7 promoter sequence to facilitate amplification via in vitro transcription (Primer 2). The primer sequences used in the 140-gene and 1001-gene experiments are listed below.

TABLE 2

| Experiment Name | Primer 1 Sequence (Index Primer 1) | Primer 2 Sequence (T7 promoter plus the reverse complement of Index Primer 2) |
|---|---|---|
| 140-gene Codebook 1 | GTTGGTCGGCA CTTGGGTGC (SEQ ID NO: 18) | TAATACGACTCACT ATAGGGAAAGCCGG TTCATCCGGTGG (SEQ ID NO: 21) |

TABLE 2-continued

| Experiment Name | Primer 1 Sequence (Index Primer 1) | Primer 2 Sequence (T7 promoter plus the reverse complement of Index Primer 2) |
|---|---|---|
| 140-gene Codebook 2 | CGATGCGCCAA TTCCGGTTC (SEQ ID NO: 19) | TAATACGACTCACT ATAGGGTGATCATC GCTCGCGGGTTG (SEQ ID NO: 22) |
| 1001-gene | CGCGGGCTATA TGCGAACCG (SEQ ID NO: 20) | TAATACGACTCAC TATAGGGCGTGGAG GGCATACAACGC (SEQ ID NO: 23) |

30-nt-long readout sequences were created by concatenating fragments of the same orthogonal primer set generated above by combining one 20-nt primer with a 10-nt fragment of another. These readout sequences were then screened, using BLAST+, for orthogonality with the index primer sequences and other readout sequences (no more than 11 nt of homology) and for potential off-target binding sites in the human genome (no more than 14 nt of homology). Fluorescently labeled readout probes with sequences complementary to the readout sequences were used to probe these readout sequences, one in each hybridization round. All used readout probes sequences are listed below.

TABLE 3

| Bit | Readout probes | |
|---|---|---|
| 1 | CGCAACGCTTGGGACGG TTCCAATCGGATC/3Cy 5Sp/ | SEQ ID NO: 24 |
| 2 | CGAATGCTCTGGCCTCG AACGAACGATAGC/3Cy 5Sp/ | SEQ ID NO: 25 |
| 3 | ACAAATCCGACCAGATC GGACGATCATGGG/3Cy 5Sp/ | SEQ ID NO: 26 |
| 4 | CAAGTATGCAGCGCGAT TGACCGTCTCGTT/3Cy 5Sp/ | SEQ ID NO: 27 |
| 5 | GCGGGAAGCACGTGGAT TAGGGCATCGACC/3Cy 5Sp/ | SEQ ID NO: 28 |
| 6 | AAGTCGTACGCCGATGC GCAGCAATTCACT/3Cy 5Sp/ | SEQ ID NO: 29 |
| 7 | CGAAACATCGGCCACGG TCCCGTTGAACTT/3Cy 5Sp/ | SEQ ID NO: 30 |
| 8 | ACGAATCCACCGTCCAG CGCGTCAAACAGA/3Cy 5Sp/ | SEQ ID NO: 31 |
| 9 | CGCGAAATCCCCGTAAC GAGCGTCCCTTGC/3Cy 5Sp/ | SEQ ID NO: 32 |
| 10 | GCATGAGTTGCCTGGCG TTGCGACGACTAA/3Cy 5Sp/ | SEQ ID NO: 33 |
| 11 | CCGTCGTCTCCGGTCCA CCGTTGCGCTTAC/3Cy 5Sp/ | SEQ ID NO: 34 |
| 12 | GGCCAATGGCCCAGGTC CGTCACGCAATTT/3Cy 5Sp/ | SEQ ID NO: 35 |
| 13 | TTGATCGAATCGGAGCG TAGCGGAATCTGC/3Cy 5Sp/ | SEQ ID NO: 36 |
| 14 | CGCGCGGATCCGCTTGT CGGGAACGGATAC/3Cy 5Sp/ | SEQ ID NO: 37 |
| 15 | GCCTCGATTACGACGGA TGTAATTCGGCCG/3Cy 5Sp/ | SEQ ID NO: 38 |
| 16 | GCCCGTATTCCCGCTTG CGAGTAGGGCAAT/3Cy 5Sp/ | SEQ ID NO: 39 |

The readout probes used for the 140-gene libraries were probes 1 through 16. The readout probes used for the 1001-gene experiment were probes 1 through 14. /3Cy5Sp/ indicates a 3' Cy5 modification.

To design the central targeting sequences of the encoding probes, the abundance of different transcripts in IMR90 cells using Cufflinks v2.1, total RNA data from the ENCODE project, and human genome annotations from Gencode v18 were complied. Probes were designed from gene models corresponding to the most abundant isoform using OligoArray2.1 with the following constraints: the target sequence region is 30-nt long; the melting temperatures of the hybridized region of the probe and cellular RNA target is greater than 70° C.; there is no cross hybridization targets with melting temperatures greater than 72° C.; there is no predicted internal secondary structures with melting temperatures greater than 76° C.; and there is no contiguous repeats of 6 or more identical nucleotides. Melting temperatures were adjusted to optimize the specificity of these probes and minimize secondary structure while still producing sufficient numbers of probes for the libraries. To decrease computational cost, isoforms were divided into 1-kb regions for probe design. Using BLAST+, all potential probes that mapped to more than one cellular RNA species were rejected. Probes with multiple targets on the same RNA were kept.

For each gene in the 140-gene experiments, 198 putative encoding probe sequences were generated by concatenating the appropriate index primers, readout sequences, and targeting regions as shown in FIG. 13. To address the possibility that concatenation of these sequences introduced new regions of homology to off-target RNAs, BLAST+ was used to screen these putative sequences against all human rRNA and tRNA sequences as well as highly expressed genes (genes with FPKM >10,000). Probes with greater than 14 nt of homology to rRNAs or tRNAs or greater than 17 nt of homology to highly expressed genes were removed. After these cuts, there were ~192 (with a standard deviation of 2) probes per gene for both MHD4 codebooks used in the 140-gene experiments. The same protocol for the 1001-gene experiments was used, as follows: Starting with 96 putative targeting sequences per gene, ~94 (with a standard deviation of 6) of encoding probes per gene were obtained after these additional homology cuts. The number of encoding probes per RNA was decreased for the 1001-gene experiments so that these probes could be synthesized from a single 100,000-member oligopool as opposed to two separate pools. Each encoding probe was designed to contain two of the four readout sequences associated with each code word, hence only half of the bound encoding probes can bind readout probe during any given hybridization round. ~192 or ~94 encoding probes per RNA were used to obtain high signal-to-background ratios for individual RNA molecules. The number of encoding probes per RNA could be substantially reduced but still allow single RNA molecules to be identified. In addition, increasing the number of readout sequences per encoding probe or using optical sectioning methods to reduce the fluorescence background may allow further reduction in the number of the encoding probes per RNA.

Two types of misidentification controls were designed. The first control (blank words) were not represented with encoding probes. The second type of control (no-target words) had encoding probes that were not targeting any cellular RNA. The targeting regions of these probes were composed of random nucleotide sequences subject to the same constraints used to design the RNA targeting sequences described above. Moreover, these random sequences were screened against the human transcriptome to ensure that they contain no significant homology (>14-nt) to any human RNA. The 140-gene measurements contained 5 blank words and 5 no-target words. The 1001-gene measurements contained 11 blank words and 5 no-target words.

Probe synthesis. The encoding probes were synthesized using the following steps, and this synthesis protocol is illustrated in FIG. 13.

Step 1: The template oligopool (CustomArray) was amplified via limited-cycle PCR on a Bio-Rad CFX96 using primer sequences specific to the desired probe set. To facilitate subsequent amplification via in vitro transcription, the reverse primer contained the T7 promoter. All primers were synthesized by IDT. This reaction was column purified (Zymo DNA Clean and Concentrator; D4003).

Step 2: The purified PCR products were then further amplified ~200-fold and converted into RNA via a high yield in vitro transcription according to the manufacturer's instructions (New England Biolabs, E2040S). Each 20 microliter reaction contained ~1 microgram of template DNA from above, 10 mM of each NTP, 1× reaction buffer, 1× RNase inhibitor (Promega RNasin, N2611) and 2 microliters of the T7 polymerase. This reaction was incubated at 37° C. for 4 hours to maximize yield. This reaction was not purified before the following steps.

Step 3: The RNA products from the above in vitro transcription reaction were then converted back into DNA via a reverse transcription reaction. Each 50 microliter reaction contained the unpurified RNA produce from Step 2 supplemented with 1.6 mM of each dNTP, 2 nmol of a reverse transcription primer, 300 units of Maxima H- reverse transcriptase (Thermo Scientific, EP0751), 60 units of RNasin, and a final 1× concentration of the Maxima RT buffer. This reaction was incubated at 50° C. for 45 minutes, and the reverse transcriptase was inactivated at 85° C. for 5 minutes. The templates for the 140-gene libraries contain a common priming region for this reverse transcription step; thus, a single primer was used for this step when creating these probes. Its sequence was CGGGTTTAGCGCCGGAAATG (SEQ ID NO: 40). A common priming region was not included for the 1001-gene library; thus, the reverse transcription was conducted with the forward primer:

CGCGGGCTATATGCGAACCG. (SEQ ID NO: 20)

Step 4: To remove the template RNA, 20 microliters of 0.25 M EDTA and 0.5 N NaOH was added to the above reaction to selectively hydrolyze RNA, and the sample was incubated at 95° C. for 10 minutes. This reaction was then immediately purified by column purification using a 100-microgram-capacity column (Zymo Research, D4030) and the Zymo Oligo Clean and Concentrator protocol. The final probes were eluted in 100 microliters of RNase-free deionized water, evaporated in a vacuum concentrator, and then resuspended in 10 μL of encoding hybridization buffer (see below). Probes were stored at −20° C. Denaturing polyacrylamide gel electrophoresis and absorption spectroscopy were used to confirm the quality of the probes and revealed that this probe synthesis protocol converts 90-100% of the reverse-transcription primer into full length probe and of the probe that is constructed, 70-80% is recovered during the purification step.

Fluorescently labeled readout probes have sequences complementary to the readout sequences described above and a Cy5 dye attached at the 3' end. These probes were obtained from IDT and HPLC purified.

Sample preparation and labeling with encoding probes. Human primary fibroblasts (American Type Culture Collection, IMR90) were used in this work. These cells are relatively large and flat, facilitating wide-field imaging without the need for optical sectioning. Cells were cultured with Eagle's Minimum Essential Medium. Cells were plated on 22-mm, #1.5 coverslips (Bioptechs, 0420-0323-2) at 350,000 cells/coverslip and incubated at 37° C. with 5% C02 for 48-96 hours within petri dishes. Cells were fixed for 20 minutes in 4% paraformaldehyde (Electron Microscopy Sciences, 15714) in 1× phosphate buffered saline (PBS; Ambion, AM9625) at room temperature, reduced for 5 minutes with 0.1% w/v sodium borohydride (Sigma, 480886) in water to reduce background fluorescence, washed three times with ice-cold a 1×PBS, permeabilized for 2 minutes with 0.5% v/v Triton (Sigma, T8787) in 1×PBS at room temperature, and washed three times with ice cold 1×PBS.

Cells were incubated for 5 minutes in encoding wash buffer comprising 2× saline-sodium citrate buffer (SSC) (Ambion, AM9763), 30% v/v formamide (Ambion, AM9342), and 2 mM vanadyl ribonucleoside complex (NEB, S1402S). 10 microliters of 100 micromolar(140-gene experiments) or 200 micromolar (1001-gene experiments) encoding probes in encoding hybridization buffer was added to the cell-containing coverslip and spread uniformly by placing another coverslip on top of the sample. Samples were then incubated in a humid chamber inside a 37° C.-hybridization oven for 18-36 hours. Encoding hybridization buffer is composed of encoding wash buffer supplemented with 1 mg/mL yeast tRNA (Life Technologies, 15401-011) and 10% w/v dextran sulfate (Sigma, D8906-50G).

Cells were then washed with primary encoding wash buffer, incubated at 47° C. for 10 minutes, and this wash was repeated for a total of three times. A 1:1000 dilution of 0.2-micrometer-diameter carboxylate-modified orange fluorescent beads (Life Technologies, F-8809) in 2×SSC was sonicated for 3 minutes and then incubated with the sample for 5 minutes. The beads were used as fiducial markers to align images obtained from multiple successive rounds of hybridization, as described below. The sample was washed once with 2×SSC, and then post-fixed with 4% v/v paraformaldehyde in 2×SSC at room temperature for 30 minutes. The sample was then washed three times with 2×SSC and either imaged immediately or stored for no longer than 12 hours at 4° C. prior to imaging. All solutions were prepared as RNase-free.

MERFISH imaging with multiple successive rounds of hybridization. The sample coverslip was assembled into a Bioptech's FCS2 flow chamber, and the flow through this chamber was controlled via a home-built fluidics system composed of three computer-controlled 8-way valves (Hamilton, MVP and HVXM 8-5) and a computer-controlled peristaltic pump (Rainin, Dynamax RP-1). The sample was imaged on a home-built microscope constructed around an Olympus IX-71 body and a 1.45 NA, 100× oil immersion objective and configured for oblique incidence excitation. The objective was heated to 37° C. with a Bioptechs objective heater. Constant focus was maintained throughout the imaging process with a home-built, auto-focusing system. Illumination was provided at 641 nm, 561 nm, and 405 nm using solid state lasers (MPB communications, VFL-P500-642; Coherent, 561-200CWCDRH; and Coherent, 1069413/AT) for excitation of the Cy5-labeled readout probes, the fiducial beads, and nuclear counterstains, respectively. These lines were combined with a custom dichroic (Chroma, zy405/488/561/647/752RP-UF1) and the emission was filtered with a custom dichroic (Chroma, ZET405/488/561/647-656/752m). Fluorescence was separated with a QuadView (Photometrics) using the dichroics T5601pxr, T6501pxr, 750dcxxr (Chroma) and the emission filters ET525/50m, WT59550m-2f, ET700/75m, HQ7701p (Chroma) and imaged with an EMCCD camera (Andor, iXon-897). The camera was configured so that a pixel corresponds to 167 nm in the sample plane. The entire system was fully automated, so that imaging and fluid handling were performed for the entire experiment without user intervention.

Sequential hybridization, imaging, and bleaching proceeded as follows. 1 mL of 10 nM of the appropriate fluorescently labeled readout probe in readout hybridization buffer (2×SSC; 10% v/v formamide; 10% w/v dextran sulfate, and 2 mM vanadyl ribonucleoside complex) was flown across the sample, flow was stopped, and the sample was incubated for 15 minutes. Then 2 mL of readout wash buffer (2×SSC, 20% v/v formamide; and 2 mM vanadyl ribonucleoside complex) was flown across the sample, flow was stopped, and the sample was incubated for 3 minutes. 2 mL of imaging buffer comprising 2×SSC, 50 mM TrisHCl pH 8, 10% w/v glucose, 2 mM Trolox (Sigma-Aldrich, 238813), 0.5 mg/mL glucose oxidase (Sigma-Aldrich, G2133), and 40 microgram/mL catalase (Sigma-Aldrich, C30) was flown across the sample. Flow was then stopped, and then approximately 75 to 100 regions were exposed to ~25 mW 642-nm and 1 mW of 561-nm light and imaged. Each region was 40 micrometers by 40 micrometers. The laser powers were measured at the microscope backport. Because the imaging buffer is sensitive to oxygen, the ~50 mL of imaging buffer used for a single experiment was made fresh at the beginning of the experiment and then stored under a layer of mineral oil throughout the measurement. Buffer stored in this fashion was stable for more than 24 hours.

After imaging, the fluorescence of the readout probes was extinguished via photobleaching. The sample was washed with 2 mL of photobleaching buffer (2×SSC and 2 mM vanadyl ribonucleoside complex), and each imaged region of the sample was exposed to 200 mW of 641-nm light for 3 s. To confirm the efficacy of this photobleaching treatment, imaging buffer was reintroduced, and the sample was imaged as described above.

The above hybridization, imaging, and photobleaching process was repeated either 16 times for the 140-gene measurements using the MHD4 code or 14 times for the 1001-gene measurements using the MHD2 code. An entire experiment was typically completed in ~20 hours.

Following completion of imaging, 2 mL of a 1:1000 dilution of Hoescht (ENZ-52401) in 2×SSC was flown through the chamber to label the nuclei of the cells. The sample was then washed immediately with 2 mL of 2×SSC followed by 2 mL of imaging buffer. Each region of the sample was then imaged once again with ~1 mW of 405-nm light.

Because cells were imaged using wide-field imaging with oblique-incidence illumination, without optical sectioning and z-scanning, the fraction of individual RNA species that was outside the axial range of the imaging geometry was quantified for 6 different RNA species using conventional smFISH. For this purpose, these cells were optically sectioned by collecting stacks of images at different focal depths through the entire depth of the cells. The images were aligned in consecutive focal planes and then computed for each cell the fraction of RNAs that were detected in the three-dimensional stack but not in the basal focal plane. It was found that only a small fraction, 15%+/−1% (Mean+/−SEM across six different RNA species) of RNA molecules were outside the imaging range of a fixed focal plane without z-scanning. These measurements also confirmed that the excitation geometry illuminated the full depth of the cells. Any optical sectioning technique could be employed in MERFISH to allow the imaging of RNAs in thicker cells or tissues.

Construction of measured words. Fluorescent spots were identified and localized in each image using a multi-Gaussian-fitting algorithm assuming a Gaussian with a uniform width of 167 nm. This algorithm was used to allow partially overlapping spots to be distinguished and individually fit. RNA spots were distinguished from background signal, i.e. signal arising from probes bound non-specifically, by setting the intensity threshold required to fit a spot with this software. Due to variation in the brightness of spots between rounds of hybridization, this threshold was adjusted appropriately for each hybridization round to minimize the combined average of the 1→0 and 0→1 error rates across all hybridization rounds (140-gene measurements) or to maximize the ratio of the number of measured words with four '1' bits to those with three or five '1' bits (1001-gene measurements). The location of the fiducial beads was identified in each frame using a faster single-Gaussian fitting algorithm.

Images of the same sample region in different rounds of hybridization were registered by rotating and translating the image to align the two fiducial beads within the same image that were most similar in location after a coarse initial alignment via image correlation. All images were aligned to a coordinate system established by the images collected in the first round of hybridization. The quality of this alignment was determined from the residual distance between five additional fiducial beads, and alignment error was typically ~20 nm.

Fluorescence spots in different hybridization rounds were connected into a single string, corresponding to a potential RNA molecule, if the distance between spots was smaller than 1 pixel (167 nm). For each string of spots, the on-off sequence of fluorescent signals in all hybridization rounds were used to assign a binary word to the potential RNA molecule, in which '1' was assigned to the hybridization rounds that contained a fluorescent signal above threshold and '0' was assigned to the other hybridization rounds. Measured words were then decoded into RNA species using the 16-bit MHD4 code or the 14-bit MHD2 code discussed above. In the case of the 16-bit MHD4 code, if the measured binary word matched the code word of a specific RNA perfectly or differed from the code word by one single bit, it was assigned to that RNA. In the case of the 14-bit MHD2 code, only if the measured binary word matched the code word of a specific RNA perfectly, was it assigned to that RNA. To determine the copy number per cell, the number of each RNA species was counted in individual cells within each 40 micrometer by 40 micrometer imaging area. It is noted that this number accounts for the majority but not all RNA molecules within a cell because a fraction of the cell could be outside the imaging area or focal depth. Tiling images of adjacent areas and adjacent focal planes could be employed to improve the counting accuracy.

In the 140-gene experiments, some regions of the cell nucleus occasionally contained too much fluorescence signal to properly identify individual RNA spots. In the 1001-gene experiments, the cell nucleus generally contained too much fluorescent signal to allow identification of individual RNA molecules. These bright regions were excluded from all subsequent analysis. This work focuses on mRNAs, which are enriched in the cytoplasm. To estimate the fraction of mRNAs missed by excluding the nucleus region, conventional smFISH was used to quantify the fraction of molecules found inside the nucleus for six different mRNAs species. It was found that only 5%+/−2% (Mean+/−SEM across six RNA species) of these RNA molecules are found in the nucleus. Employment of super-resolution imaging and/or optical sectioning could potentially allow individual molecules in these dense nucleus regions to be identified, which would be particularly useful for probing those noncoding RNAs that are enriched in the nucleus.

smFISH measurements of individual genes. Pools of 48 fluorescently-labeled (Quasar 670) oligonucleotide probes per RNA were purchased from Biosearch Technologies. 30-nt probe sequences were taken directly from a random subset of the targeting regions used for the multiplexed measurements. Cells were fixed and permeabilized as described above. 10 microliters of 250 nM oligonucleotide probes in encoding hybridization buffer (described above) was added to the cell-containing coverslip and spread uniformly by placing another coverslip on top of the sample. Samples were then incubated in a humid chamber inside a 37° C.-hybridization oven for 18 hours. Cells were then washed with encoding wash buffer (described above) at 37° C. for 10 minutes, and this wash was repeated for a total of three times. The sample was then washed three times with 2×SSC and imaged in imaging buffer using the same imaging geometry as described above for MERFISH.

Bulk RNA sequencing. Total RNA was extracted from IMR90 cells cultured as above using the Zymo Quick RNA MiniPrep kit (R1054) according to the manufacturer's instructions. polyA RNA was then selected (NEB; E7490), and a sequencing library was constructed using the NEBNext Ultra RNA library preparation kit (NEB; E7530), amplified with custom oligonucleotides, and 150-bp reads were obtained from on a MiSeq. These sequences were aligned to the human genome (Gencode v18) and isoform abundance was computed with cufflinks.

Calculation of the predicted scaling and error properties of different encoding schemes. Analytic expressions were derived for the dependence of the number of possible code words, the calling rate, and the misidentification rate on N. The calling rate is defined as the fraction of RNA molecules that are properly identified. The misidentification rate is defined as the fraction of RNA molecules that are misidentified as a wrong RNA species. For encoding schemes with an error-detection capability, the calling rate and misidentification rate does not add up to 1 because a fraction of the molecules not called properly can be detected as errors and discarded and, hence, not misidentified as a wrong species. These calculations assume that the probability of misreading bits is constant for all hybridization rounds but differs for the 1→0 and 0→1 errors. Experimentally measured average 1→0 and 0→1 error rates (10% and 4% respectively) were used for the estimates shown in FIGS. 5B-5D. For simplicity, the word corresponding to all '0's was not removed from calculations.

For the simple binary encoding scheme in which all possible N-bit binary words are assigned to unique RNA species, the number of possible code words is $2^N$. The number of words that could be used to encode RNA is actually $2^N-1$ because the code word '00 . . . 0' does not contain detectable fluorescence in any hybridization round, but for simplicity the word corresponding to all '0's was not removed from subsequent calculations. The error introduced by this approximation is negligible. For any given word with m '1's and N−m '0's the probability of measuring that word without error (the fraction of RNAs that is properly called) is:

$$(1-p_1)^m (1-p_0)^{N-m}, \quad (1)$$

where $p_1$ is 1→0 error rate and $p_0$ is 0→1 error rate per bit. Because different words in this simple binary encoding scheme can have different numbers of '1' bits, the calling rate for different words will differ if $p_1 \neq p_0$. The average calling rate, reported in FIG. 5C, was determined from the weighted average of the value of Eq. (1) for all words. This weighted average is: IDC-28 E $$\frac{1}{2^N} \sum_{m=0}^{N} \binom{N}{m} (1-p_1)^m (1-p_0)^{N-m}, \quad (2)$$

where $$\binom{N}{m}$$

is the binomial coefficient and corresponds to the number of words with m '1' bits in this encoding scheme. Since in this encoding scheme every error produces a binary word that encodes a different RNA, the average misidentification rate for this encoding scheme, reported in FIG. 5D, follows directly from (2):

$$1 - \frac{1}{2^N} \sum_{m=0}^{N} \binom{N}{m} (1-p_1)^m (1-p_0)^{N-m}. \quad (3)$$

To calculate the scaling and error properties of the extended Hamming distance 4 (HD4) code, the generator matrix for the desired number of data bits using standard methods was first created. The generator matrix determines the specific words that are present in a given encoding scheme and was used to directly determine the number of encoded words as a function of the number of bits. In this encoding scheme, the calling rate corresponds to the fraction of words measured without error as well as the fraction of words measured with a single-bit error. For code words with m '1' bits, this fraction is determined by the following expression:

$$(1-p_1)^m(1-p_0)^{N-m} + mp_1{}^1(1-p_1)^{m-1}(1-p_0)^{N-m} + (N-m)p_0{}^1(1-p_1)^m(1-p_0)^{N-m-1} \quad (4)$$

where the first term is the probability of not making any errors, the second term corresponds to the total probability of making one 1→0 error at any of the m '1' bits without making any other 0→1 errors, and the final term corresponds to the total probability of making one 0→1 error at any of the N−m '0' bits without making any 1→0 errors. Because the number of '1' bits can differ between words in this encoding scheme, the average calling rate reported in FIG. 5C was computed from a weighted average over Eq. (4) for different values of m. The weight for each term was determined from the number of words that contain m '1' bits as determined from the generator matrix described above.

Because RNA-encoding words are separated by a minimum Hamming distance of 4, at least 4 errors are required to switch one word into another. If error correction is applied, then 3 or 5 errors could also convert one RNA into another. Thus, the misidentification rate from all possible combinations of 3-bit, 4-bit and 5-bit errors was estimated for code words with m '1' bits. Technically, >5-bit errors could also convert one RNA into another, but the probability of making such errors is negligible because of the small per-bit error rate. This expression was approximated with:

$$\sum_{i=0}^{4}\binom{m}{i}\binom{N-m}{4-i}p_1^i p_0^{4-i}(1-p_1)^{m-i}(1-p_0)^{N-m-(4-i)} + \quad (5)$$

$$\sum_{i=0}^{3}\binom{m}{i}\binom{N-m}{3-i}p_1^i p_0^{3-i}(1-p_1)^{m-i}(1-p_0)^{N-m-(3-i)} +$$

$$\sum_{i=0}^{5}\binom{m}{i}\binom{N-m}{5-i}p_1^i p_0^{5-i}(1-p_1)^{m-i}(1-p_0)^{N-m-(5-i)} +$$

The first sum corresponds to all of the ways in which exactly four mistakes can be made. Similarly, the second and third sums correspond to all of the ways in which exactly three or five mistakes can be made. Eq. (5) provides an upper bound for the misidentification rate because not all three, four, or five bit errors produce a word that matches or would be corrected to another legitimate word. Again because the number of '1' bits can differ between words, the average misidentification rate reported in FIG. 5D is calculated as a weighted average of Eq. (5) over the number of words that have m '1' bits.

To generate the MHD4 code where the number of '1' bits for each code word is set to 4, the HD4 codes were first generated as described above, and then all code words that did not contain four '1's were removed. The calling rate of this code, reported in FIG. 5C, was directly calculated from Eq. (4) but with m=4 because all code words in this code have four '1' bits. The misidentification rate of this code, reported in FIG. 5D, was calculated by modifying Eq. (5) with the following considerations: (i) the number of '1' bits, m, was set to 4 and (ii) errors that produce words that do not contain three, four, or five '1' bits were excluded. Thus, the expression in Eq. (5) was simplified to $$\binom{4}{2}\binom{N-4}{2}p_1^2 p_0^2 (1-p_1)^2 (1-p_0)^{N-6} + \quad (6)$$

-continued $$\binom{4}{1}\binom{N-4}{2}p_1^1 p_0^2 (1-p_1)^3 (1-p_0)^{N-6} +$$

$$\binom{4}{2}\binom{N-4}{1}p_1^2 p_0^1 (1-p_1)^2 (1-p_0)^{N-5}$$

$$\binom{4}{2}\binom{N-4}{3}p_1^2 p_0^3 (1-p_1)^2 (1-p_0)^{N-7} +$$

$$\binom{4}{3}\binom{N-4}{2}p_1^3 p_0^2 (1-p_1)^1 (1-p_0)^{N-6}$$

Again, this expression is an upper bound on the actual misidentification rate because not all words with four '1's are valid code words.

Estimates of the 1→0 and 0→1 error rates for each hybridization round. To compute the probability of misreading a bit at a given hybridization round, the error correcting properties of the MHD4 code were used. Briefly, the probabilities of 1→0 or 0→1 errors were derived in the following way. Let the probability of making an error at the ith bit, i.e. ith hybridization round, be $p_i$ and the actual number of RNA molecules of the given species be A, then the number of exact matches for this RNA will be $$W_E = A \prod_{i=1}^{16}(1-p_i)$$

and the number of one-bit error corrected matches for this RNA corresponding to errors at the ith bit will be $$W_i = A \frac{p_i}{(1-p_i)} \prod_{j=1}^{16}(1-p_j).$$

The $p_i$ can be directly derived from the ratio:

$$W_i/W_E = \frac{p_i}{(1-p_i)}.$$

This ratio assumes that the one-bit error-corrected counts were only generated from single-bit errors from the correct word and that multi-error contamination from other RNA words is negligible. Given that the error rate per hybridization round is small and that it takes at least three errors to convert one RNA-encoding word into a word that would be misidentified as another RNA, the above approximation should be a good one.

To compute the average 1→0 or 0→1 error probabilities for each of the 16 hybridization rounds, the above approach was used to calculate the per-bit error rates for each bit of every gene, and these errors were sorted based on whether they correspond to a 1→0 or a 0→1 error, and the average of these errors for each bit weighted by the number of counts observed for the corresponding gene was taken.

Estimates of the calling rate for individual RNA species from actual imaging data. With the estimates of the 1→0 or 0→1 error probabilities for each round of hybridization as determined above, it is possible to estimate the calling rate for each RNA based on the specific word used to encoded it. Specifically, the fraction of an RNA species that is called correctly is determined by $$\prod_{i=1}^{N}(1-p_i) + \sum_{j=1}^{N}\frac{p_j}{(1-p_j)}\prod_{i=1}^{N}(1-p_i), \quad (7)$$

where the first term represent the probability of observing an exact match of the code word and the second term represent the probability of observing an error-corrected match (i.e. with one-bit error). The values of the per-bit error rate $p_i$ for each RNA species are determined by the specific code word for that RNA and the measured 1→0 or 0→1 error rates for each round of hybridization. If the code word of the RNA contains a '1' in the ith bit, then $p_i$ is determined from the 1→0 error rate for the ith hybridization round; if the word contains a '0' in the ith bit, $p_i$ is determined from the 0→1 error rate for the ith hybridization round.

Hierarchical clustering analysis of the co-variation in RNA abundance. Hierarchical clustering of the co-variation in gene expression for both the 140-gene and 1001-gene experiments was conducted as follows. First, the distance between every pair of genes was determined as 1 minus the Pearson correlation coefficient of the cell-to-cell variation of the measured copy numbers of these two RNA species, both normalized by the total RNA counted in the cell. Thus, highly correlated genes are 'closer' to one another and highly anti-correlated genes are 'further' apart. An agglomerative hierarchical cluster tree was then constructed from these distances using the Unweighted Pair Group Method with Arithmetic mean (UPGMA). Specifically, starting with individual genes, hierarchical clusters were constructed by identifying the two clusters (or individual genes) that are closest to one another according to the arithmetic mean of the distances between all inter-cluster gene pairs. The pairs of clusters (or individual genes) with the smallest distance are then grouped together and the process is repeated. The matrix of pairwise correlations was then sorted based on the order of the genes within these trees.

Groups of genes with substantial co-variations were identified by selecting a threshold on the hierarchical cluster tree (indicated by the dashed lines in FIGS. 7D and 10A) that produced approximately 10 groups of genes each of which contains at least 4 members for the 140-gene experiments or approximately 100 groups each of which contains at least 3 members for the 1001-gene experiments. It is noted that one can change the threshold in order to identify either more tightly coupled smaller groups or larger groups with relatively loose coupling.

A probability value for the confidence that a gene belongs to a specific group was determined by computing the difference between the average correlation coefficient between that gene and all other members of that group and the average correlation coefficient between that gene and all other measured genes outside that group. The significance (p-value) of this difference was determined with the student's t-test.

Because hierarchical clustering is inherently a one-dimensional analysis, i.e. any given genes can only be a member of a single group, this analysis does not allow all correlated gene groups to be identified. Higher dimension analysis, such as principal component analysis or k-means clustering, could be used to identify more co-varying gene clusters.

Analysis of RNA spatial distributions. To identify genes that have similar spatial distributions, each of the measured cells was subdivided into 2×2 regions and calculated the fraction of each RNA species present in each of these bins. To control for the fact that some regions of the cell naturally contain more RNA than others, the enrichment was calculated for each gene, i.e., the ratio of the observed fraction in a given region for a given RNA species to the average fraction observed for all genes in that same region. For each pair of RNA species, the Pearson correlation coefficient of the region-to-region variation in enrichment of these two RNA species for each cell was determined and the correlation coefficients were averaged over ~400 cells imaged in 7 independent data sets. RNA species were then clustered based on these average correlation coefficients using the same hierarchical clustering algorithm described above. Because of the large number of cells used for the analysis, it was found that the coarse spatial binning (2×2 regions per cell) was sufficient to capture the spatial correlation between genes and finer binning did not produce more significantly correlated groups.

To measure the distances of genes from the nuclei and from the cell edge, brightness thresholds on the cell images were first used to segment the nuclei and the cell edges identified. The distance from every RNA molecule to the nearest part of the nucleus and nearest part of the cell edge was then determined. For each data set, the average distance for each RNA species averaged over all the cells measured was then computed. These distances were averaged for the group I genes, group II genes or all genes. Only those RNA species with at least 10 counts per cell were used in this analysis to minimize statistical error on the distance values.

Gene ontology (GO) analysis. Groups of genes were selected from the hierarchical trees as discussed above. A collection of GO terms was determined for all measured RNA species as well as the RNA species associated with each group from the most recent human GO annotations using both the annotated GO terms and terms immediately upstream or downstream of the found annotations. The enrichment of these annotations was calculated from the ratio of the fraction of genes within each group that have this term to the fraction of all measured genes that have this term and the p-value for this enrichment was calculated via the hypergeometric function. Only statistically significantly enriched GO terms with a p-value less than 0.05 were considered.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

When the word "about" is used herein in reference to a number, it should be understood that still another embodiment of the invention includes that number not modified by the presence of the word "about."

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The invention claimed is:

1. A method for imaging RNA spatial organization in a sample comprising:
   a. contacting the sample comprising a plurality of distinct RNA species in situ with a plurality of primary nucleic acid probe pools each of the nucleic acid probes comprising a target sequence and one or more read sequences, wherein each pool of nucleic acid probes hybridize to a distinct RNA species and each pool of probes encode a N-bit codeword with a Hamming weight of at least 2 that was assigned to each distinct RNA species, wherein each assigned N-bit codeword is a valid codeword with a Hamming distance equal to or greater than 2 between valid codewords and wherein each of the read sequences correspond to a bit value of 1 for the codewords assigned to the distinct RNA species;
   b. contacting the bound primary nucleic acid probes with a plurality of readout probes comprising a fluorescent label, wherein the readout probes hybridize to the read sequences of the primary nucleic probes;
   c. imaging the readout probes bound to the primary nucleic acid probes; and,
   d. repeating steps b) and c) in one or more sequential hybridization and imaging rounds until all N positions in the N-bit codeword have been imaged providing an imaged codeword corresponding to each distinct RNA species in a spatial organization.

2. The method of claim 1, wherein the assigned N-bit codewords have a Hamming distance equal to or greater than 4 between each of the valid codewords.

3. The method of claim 1, wherein the N-bit codeword has a Hamming weight of 4.

4. The method of claim 1, wherein the imaged codeword is matched to a valid codeword assigned to a distinct RNA species.

5. The method of claim 1 wherein the Hamming distance is 4 or greater and the imaged codewords are matched to valid codewords or discarded.

6. The method of claim 1, wherein the N-bit codeword has a Hamming weight of 4 and the Hamming distance is 4 or greater and the imaged codewords are matched to valid codewords or discarded.

7. The method of claim 1, wherein the RNA species is a RNA transcript.

8. The method of claim 1, comprising determining the spatial organization of the transcriptome from a single cell.

9. The method of claim 1, wherein each primary nucleic acid probe pool comprises at least 10 different primary nucleic acid probes.

10. The method of claim 1, wherein each primary nucleic acid probe pool comprises at least four distinct read sequences.

11. The method of claim 1, wherein each primary nucleic acid probe pool comprises four distinct read sequences.

12. The method of claim 1, wherein each primary nucleic acid probe pool comprises at least eight distinct read sequences.

13. The method of claim 1, wherein the primary nucleic acid probes comprise a target sequence, with an average length of between 10 and 200 nucleotides, that hybridize the distinct RNA species.

14. The method of claim 1, wherein each primary nucleic acid probe pool comprises at least 10 different target sequences.

15. The method of claim 1, wherein after each hybridization and imaging round the fluorescent read out probe is quenched to inactivate.

16. The method of claim 1, wherein after each hybridization and imaging round the fluorescent read out probe is inactivated by chemically or enzymatically cleaving the fluorescent label from the read out probe.

17. The method of claim 1, wherein the N-bit binary code comprises at least a 16-bit code.

18. The method of claim 1, wherein the plurality of fluorescent readout probes comprise at least two distinct fluorescent labels.

19. The method of claim 1, wherein the plurality of fluorescent readout probes comprise at least three distinct fluorescent labels.

20. The method of claim 1, wherein the spatial organization of the distinct RNA species is imaged in 2 dimensions.

21. The method of claim 1, wherein the spatial organization of the distinct RNA species is imaged in 3 dimensions.

22. The method of claim 1, further comprising determining abundance for the distinct RNA species.

* * * * *

SEQUENCE LISTING

```
Sequence total quantity: 40
SEQ ID NO: 1           moltype = DNA  length = 120
FEATURE                Location/Qualifiers
misc_feature           1..120
                       note = Synthetic Polynucleotide
source                 1..120
                       mol_type = other DNA
                       organism = synthetic construct
SEQUENCE: 1
gttggcgacg aaagcactgc gattggaacc gtcccaagcg ttgcgcttaa tggatcatca   60
attttgtctc actacgacgg tcaatcgcgc tgcatacttg cgtcggtcgg acaaacgagg  120

SEQ ID NO: 2           moltype = DNA  length = 30
FEATURE                Location/Qualifiers
misc_feature           1..30
                       note = Synthetic Polynucleotide
source                 1..30
                       mol_type = other DNA
                       organism = synthetic construct
SEQUENCE: 2
cgcaacgctt gggacggttc caatcggatc                                    30

SEQ ID NO: 3           moltype = DNA  length = 30
FEATURE                Location/Qualifiers
misc_feature           1..30
```

```
                        note = Synthetic Polynucleotide
source                  1..30
                        mol_type = other DNA
                        organism = synthetic construct
SEQUENCE: 3
cgaatgctct ggcctcgaac gaacgatagc                                              30

SEQ ID NO: 4            moltype = DNA  length = 30
FEATURE                 Location/Qualifiers
misc_feature            1..30
                        note = Synthetic Polynucleotide
source                  1..30
                        mol_type = other DNA
                        organism = synthetic construct
SEQUENCE: 4
acaaatccga ccagatcgga cgatcatggg                                              30

SEQ ID NO: 5            moltype = DNA  length = 30
FEATURE                 Location/Qualifiers
misc_feature            1..30
                        note = Synthetic Polynucleotide
source                  1..30
                        mol_type = other DNA
                        organism = synthetic construct
SEQUENCE: 5
caagtatgca gcgcgattga ccgtctcgtt                                              30

SEQ ID NO: 6            moltype = DNA  length = 30
FEATURE                 Location/Qualifiers
misc_feature            1..30
                        note = Synthetic Polynucleotide
source                  1..30
                        mol_type = other DNA
                        organism = synthetic construct
SEQUENCE: 6
tgcgtcgtct ggctagcacg gcacgcaaat                                              30

SEQ ID NO: 7            moltype = DNA  length = 30
FEATURE                 Location/Qualifiers
misc_feature            1..30
                        note = Synthetic Polynucleotide
source                  1..30
                        mol_type = other DNA
                        organism = synthetic construct
SEQUENCE: 7
aagtcgtacg ccgatgcgca gcaattcact                                              30

SEQ ID NO: 8            moltype = DNA  length = 30
FEATURE                 Location/Qualifiers
misc_feature            1..30
                        note = Synthetic Polynucleotide
source                  1..30
                        mol_type = other DNA
                        organism = synthetic construct
SEQUENCE: 8
cgaaacatcg gccacggtcc cgttgaactt                                              30

SEQ ID NO: 9            moltype = DNA  length = 30
FEATURE                 Location/Qualifiers
misc_feature            1..30
                        note = Synthetic Polynucleotide
source                  1..30
                        mol_type = other DNA
                        organism = synthetic construct
SEQUENCE: 9
acgaatccac cgtccagcgc gtcaaacaga                                              30

SEQ ID NO: 10           moltype = DNA  length = 30
FEATURE                 Location/Qualifiers
misc_feature            1..30
                        note = Synthetic Polynucleotide
source                  1..30
                        mol_type = other DNA
                        organism = synthetic construct
SEQUENCE: 10
cgcgaaatcc ccgtaacgag cgtcccttgc                                              30

SEQ ID NO: 11           moltype = DNA  length = 30
FEATURE                 Location/Qualifiers
```

```
misc_feature            1..30
                        note = Synthetic Polynucleotide
source                  1..30
                        mol_type = other DNA
                        organism = synthetic construct
SEQUENCE: 11
gcatgagttg cctggcgttg cgacgactaa                                            30

SEQ ID NO: 12           moltype = DNA  length = 30
FEATURE                 Location/Qualifiers
misc_feature            1..30
                        note = Synthetic Polynucleotide
source                  1..30
                        mol_type = other DNA
                        organism = synthetic construct
SEQUENCE: 12
ccgtcgtctc cggtccaccg ttgcgcttac                                            30

SEQ ID NO: 13           moltype = DNA  length = 30
FEATURE                 Location/Qualifiers
misc_feature            1..30
                        note = Synthetic Polynucleotide
source                  1..30
                        mol_type = other DNA
                        organism = synthetic construct
SEQUENCE: 13
ggccaatggc ccaggtccgt cacgcaattt                                            30

SEQ ID NO: 14           moltype = DNA  length = 30
FEATURE                 Location/Qualifiers
misc_feature            1..30
                        note = Synthetic Polynucleotide
source                  1..30
                        mol_type = other DNA
                        organism = synthetic construct
SEQUENCE: 14
ttgatcgaat cggagcgtag cggaatctgc                                            30

SEQ ID NO: 15           moltype = DNA  length = 30
FEATURE                 Location/Qualifiers
misc_feature            1..30
                        note = Synthetic Polynucleotide
source                  1..30
                        mol_type = other DNA
                        organism = synthetic construct
SEQUENCE: 15
cgcgcggatc cgcttgtcgg gaacggatac                                            30

SEQ ID NO: 16           moltype = DNA  length = 30
FEATURE                 Location/Qualifiers
misc_feature            1..30
                        note = Synthetic Polynucleotide
source                  1..30
                        mol_type = other DNA
                        organism = synthetic construct
SEQUENCE: 16
gcctcgatta cgacggatgt aattcggccg                                            30

SEQ ID NO: 17           moltype = DNA  length = 30
FEATURE                 Location/Qualifiers
misc_feature            1..30
                        note = Synthetic Polynucleotide
source                  1..30
                        mol_type = other DNA
                        organism = synthetic construct
SEQUENCE: 17
gcccgtattc ccgcttgcga gtagggcaat                                            30

SEQ ID NO: 18           moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 18
gttggtcggc acttgggtgc                                                       20

SEQ ID NO: 19           moltype = DNA  length = 20
```

```
FEATURE            Location/Qualifiers
misc_feature       1..20
                   note = Synthetic Polynucleotide
source             1..20
                   mol_type = other DNA
                   organism = synthetic construct
SEQUENCE: 19
cgatgcgcca attccggttc                                                    20

SEQ ID NO: 20      moltype = DNA   length = 20
FEATURE            Location/Qualifiers
misc_feature       1..20
                   note = Synthetic Polynucleotide
source             1..20
                   mol_type = other DNA
                   organism = synthetic construct
SEQUENCE: 20
cgcgggctat atgcgaaccg                                                    20

SEQ ID NO: 21      moltype = DNA   length = 40
FEATURE            Location/Qualifiers
misc_feature       1..40
                   note = Synthetic Polynucleotide
source             1..40
                   mol_type = other DNA
                   organism = synthetic construct
SEQUENCE: 21
taatacgact cactataggg aaagccggtt catccggtgg                              40

SEQ ID NO: 22      moltype = DNA   length = 40
FEATURE            Location/Qualifiers
misc_feature       1..40
                   note = Synthetic Polynucleotide
source             1..40
                   mol_type = other DNA
                   organism = synthetic construct
SEQUENCE: 22
taatacgact cactataggg tgatcatcgc tcgcgggttg                              40

SEQ ID NO: 23      moltype = DNA   length = 39
FEATURE            Location/Qualifiers
misc_feature       1..39
                   note = Synthetic Polynucleotide
source             1..39
                   mol_type = other DNA
                   organism = synthetic construct
SEQUENCE: 23
taatacgact cactataggg cgtggagggc atacaacgc                               39

SEQ ID NO: 24      moltype = DNA   length = 30
FEATURE            Location/Qualifiers
misc_feature       1..30
                   note = Synthetic Polynucleotide
source             1..30
                   mol_type = other DNA
                   organism = synthetic construct
SEQUENCE: 24
cgcaacgctt gggacggttc caatcggatc                                         30

SEQ ID NO: 25      moltype = DNA   length = 30
FEATURE            Location/Qualifiers
misc_feature       1..30
                   note = Synthetic Polynucleotide
source             1..30
                   mol_type = other DNA
                   organism = synthetic construct
SEQUENCE: 25
cgaatgctct ggcctcgaac gaacgatagc                                         30

SEQ ID NO: 26      moltype = DNA   length = 30
FEATURE            Location/Qualifiers
misc_feature       1..30
                   note = Synthetic Polynucleotide
source             1..30
                   mol_type = other DNA
                   organism = synthetic construct
SEQUENCE: 26
acaaatccga ccagatcgga cgatcatggg                                         30
```

```
SEQ ID NO: 27            moltype = DNA   length = 30
FEATURE                  Location/Qualifiers
misc_feature             1..30
                         note = Synthetic Polynucleotide
source                   1..30
                         mol_type = other DNA
                         organism = synthetic construct
SEQUENCE: 27
caagtatgca gcgcgattga ccgtctcgtt                                        30

SEQ ID NO: 28            moltype = DNA   length = 30
FEATURE                  Location/Qualifiers
misc_feature             1..30
                         note = Synthetic Polynucleotide
source                   1..30
                         mol_type = other DNA
                         organism = synthetic construct
SEQUENCE: 28
gcgggaagca cgtggattag ggcatcgacc                                        30

SEQ ID NO: 29            moltype = DNA   length = 30
FEATURE                  Location/Qualifiers
misc_feature             1..30
                         note = Synthetic Polynucleotide
source                   1..30
                         mol_type = other DNA
                         organism = synthetic construct
SEQUENCE: 29
aagtcgtacg ccgatgcgca gcaattcact                                        30

SEQ ID NO: 30            moltype = DNA   length = 30
FEATURE                  Location/Qualifiers
misc_feature             1..30
                         note = Synthetic Polynucleotide
source                   1..30
                         mol_type = other DNA
                         organism = synthetic construct
SEQUENCE: 30
cgaaacatcg gccacggtcc cgttgaactt                                        30

SEQ ID NO: 31            moltype = DNA   length = 30
FEATURE                  Location/Qualifiers
misc_feature             1..30
                         note = Synthetic Polynucleotide
source                   1..30
                         mol_type = other DNA
                         organism = synthetic construct
SEQUENCE: 31
acgaatccac cgtccagcgc gtcaaacaga                                        30

SEQ ID NO: 32            moltype = DNA   length = 30
FEATURE                  Location/Qualifiers
misc_feature             1..30
                         note = Synthetic Polynucleotide
source                   1..30
                         mol_type = other DNA
                         organism = synthetic construct
SEQUENCE: 32
cgcgaaatcc ccgtaacgag cgtcccttgc                                        30

SEQ ID NO: 33            moltype = DNA   length = 30
FEATURE                  Location/Qualifiers
misc_feature             1..30
                         note = Synthetic Polynucleotide
source                   1..30
                         mol_type = other DNA
                         organism = synthetic construct
SEQUENCE: 33
gcatgagttg cctggcgttg cgacgactaa                                        30

SEQ ID NO: 34            moltype = DNA   length = 30
FEATURE                  Location/Qualifiers
misc_feature             1..30
                         note = Synthetic Polynucleotide
source                   1..30
                         mol_type = other DNA
                         organism = synthetic construct
SEQUENCE: 34
ccgtcgtctc cggtccaccg ttgcgcttac                                        30
```

```
SEQ ID NO: 35            moltype = DNA  length = 30
FEATURE                  Location/Qualifiers
misc_feature             1..30
                         note = Synthetic Polynucleotide
source                   1..30
                         mol_type = other DNA
                         organism = synthetic construct
SEQUENCE: 35
ggccaatggc ccaggtccgt cacgcaattt                                        30

SEQ ID NO: 36            moltype = DNA  length = 30
FEATURE                  Location/Qualifiers
misc_feature             1..30
                         note = Synthetic Polynucleotide
source                   1..30
                         mol_type = other DNA
                         organism = synthetic construct
SEQUENCE: 36
ttgatcgaat cggagcgtag cggaatctgc                                        30

SEQ ID NO: 37            moltype = DNA  length = 30
FEATURE                  Location/Qualifiers
misc_feature             1..30
                         note = Synthetic Polynucleotide
source                   1..30
                         mol_type = other DNA
                         organism = synthetic construct
SEQUENCE: 37
cgcgcggatc cgcttgtcgg gaacggatac                                        30

SEQ ID NO: 38            moltype = DNA  length = 30
FEATURE                  Location/Qualifiers
misc_feature             1..30
                         note = Synthetic Polynucleotide
source                   1..30
                         mol_type = other DNA
                         organism = synthetic construct
SEQUENCE: 38
gcctcgatta cgacggatgt aattcggccg                                        30

SEQ ID NO: 39            moltype = DNA  length = 30
FEATURE                  Location/Qualifiers
misc_feature             1..30
                         note = Synthetic Polynucleotide
source                   1..30
                         mol_type = other DNA
                         organism = synthetic construct
SEQUENCE: 39
gcccgtattc ccgcttgcga gtagggcaat                                        30

SEQ ID NO: 40            moltype = DNA  length = 20
FEATURE                  Location/Qualifiers
misc_feature             1..20
                         note = Synthetic Polynucleotide
source                   1..20
                         mol_type = other DNA
                         organism = synthetic construct
SEQUENCE: 40
cgggtttagc gccggaaatg                                                   20
```